US012788260B2

(12) United States Patent
Rogers et al.

(10) Patent No.: US 12,788,260 B2
(45) Date of Patent: Nov. 10, 2026

(54) WIRELESS MEDICAL SENSORS AND METHODS

(71) Applicants: NORTHWESTERN UNIVERSITY, Evanston, IL (US); REHABILITATION INSTITUTE OF CHICAGO, Chicago, IL (US)

(72) Inventors: John A. Rogers, Wilmette, IL (US); Shuai Xu, Evanston, IL (US); Kun Hyuck Lee, Evanston, IL (US); Xiaoyue Ni, Evanston, IL (US); Angela Roberts, Evanston, IL (US); Bonnie Martin-Harris, Evanston, IL (US); Leora Cherney, Morton Grove, IL (US); Arun Jayaraman, River Forest, IL (US); Edna Babbitt, Chicago, IL (US); Megan O'Brien, Chicago, IL (US)

(73) Assignees: Northwestern University, Evanston, IL (US); Rehabilitation Institute of Chicago, Chicago, IL (US)

( * ) Notice: Subject to any disclaimer, the term of this patent is extended or adjusted under 35 U.S.C. 154(b) by 773 days.

(21) Appl. No.: 16/970,023

(22) PCT Filed: Feb. 15, 2019

(86) PCT No.: PCT/US2019/018318
§ 371 (c)(1),
(2) Date: Aug. 14, 2020

(87) PCT Pub. No.: WO2019/161277
PCT Pub. Date: Aug. 22, 2019

(65) Prior Publication Data

US 2021/0113099 A1 Apr. 22, 2021

Related U.S. Application Data

(60) Provisional application No. 62/753,203, filed on Oct. 31, 2018, provisional application No. 62/631,692,
(Continued)

(51) Int. Cl.
*A61B 5/0205* (2006.01)
*A61B 5/00* (2006.01)
(Continued)

(52) U.S. Cl.
CPC .......... *A61B 5/02055* (2013.01); *A61B 5/002* (2013.01); *A61B 5/1118* (2013.01);
(Continued)

(58) Field of Classification Search
CPC ... A61B 5/6898; A61B 5/6823; A61B 5/6822; A61B 5/682; A61B 5/6815;
(Continued)

(56) References Cited

U.S. PATENT DOCUMENTS

2006/0037615 A1* 2/2006 Wilkinson ............ A61B 5/085 128/204.23
2006/0264730 A1 11/2006 Stivoric et al.
(Continued)

FOREIGN PATENT DOCUMENTS

JP 2008502386 A 1/2008
JP 2011504063 A 1/2011
(Continued)

OTHER PUBLICATIONS

EPO, "Supplementary European Search Report for EP Application No. 19754303.6", Munich, Germany, Sep. 24, 2021.
(Continued)

*Primary Examiner* — Amanda L Steinberg
(74) *Attorney, Agent, or Firm* — Nolte Lackenbach Siegel; N. Alexander Nolte

(57) ABSTRACT

Provided herein are medical sensors and related methods for measuring a real-time personal metric. The medical device
(Continued)

may comprise an electronic device having a sensor comprising an accelerometer and a bidirectional wireless communication system electronically connected to the electronic device for sending an output signal from the sensor to an external device and receiving commands from an external controller to the electronic device.

60 Claims, 66 Drawing Sheets

Related U.S. Application Data filed on Feb. 17, 2018, provisional application No. 62/710,324, filed on Feb. 16, 2018.

(51) Int. Cl.

| | |
|---|---|
| ***A61B 5/024*** | (2006.01) |
| ***A61B 5/08*** | (2006.01) |
| ***A61B 5/11*** | (2006.01) |
| ***A61B 5/1455*** | (2006.01) |
| ***G10L 25/66*** | (2013.01) |
| ***G16H 40/67*** | (2018.01) |
| ***H02J 50/10*** | (2016.01) |
| ***H04R 1/08*** | (2006.01) |

(52) U.S. Cl.

CPC ........ *A61B 5/14551* (2013.01); *A61B 5/4082* (2013.01); *A61B 5/4205* (2013.01); *A61B 5/4803* (2013.01); *A61B 5/4815* (2013.01); *A61B 5/6815* (2013.01); *A61B 5/682* (2013.01); *A61B 5/6822* (2013.01); *A61B 5/6823* (2013.01); *A61B 5/6898* (2013.01); *A61B 5/7267* (2013.01); *A61B 5/7405* (2013.01); *A61B 5/742* (2013.01); *A61B 5/7455* (2013.01); *G10L 25/66* (2013.01); *G16H 40/67* (2018.01); *H04R 1/08* (2013.01); *A61B 5/024* (2013.01); *A61B 5/0816* (2013.01); *A61B 5/0823* (2013.01); *A61B 2503/045* (2013.01); *A61B 2560/0214* (2013.01); *A61B 2562/0204* (2013.01); *A61B 2562/0219* (2013.01); *A61B 2562/0223* (2013.01); *A61B 2562/0247* (2013.01); *A61B 2562/164* (2013.01); *H02J 50/10* (2016.02)

(58) Field of Classification Search

CPC ...... A61B 2562/164; A61B 2562/0247; A61B 2562/0223; A61B 2562/0219; A61B 2562/0204

See application file for complete search history.

(56) References Cited

U.S. PATENT DOCUMENTS

| | | | | |
|---|---|---|---|---|
| 2008/0077192 | A1* | 3/2008 | Harry | A61N 1/0476 42/84 |
| 2011/0092882 | A1 | 4/2011 | Firlik et al. | |
| 2013/0041235 | A1* | 2/2013 | Rogers | A61N 1/05 600/386 |
| 2013/0245499 | A1 | 9/2013 | Crary et al. | |
| 2013/0310661 | A1* | 11/2013 | Jedwab | A61B 5/4205 600/587 |
| 2014/0121557 | A1* | 5/2014 | Gannon | G01K 1/024 600/549 |
| 2014/0240932 | A1* | 8/2014 | Hsu | H05K 1/036 361/749 |
| 2015/0250420 | A1* | 9/2015 | Longinotti-Buitoni | A61B 5/1135 600/534 |
| 2015/0351690 | A1* | 12/2015 | Toth | A61B 5/291 600/391 |
| 2015/0373831 | A1* | 12/2015 | Rogers | H01L 23/22 29/829 |
| 2016/0073953 | A1 | 3/2016 | Sazonov | |
| 2017/0035345 | A1* | 2/2017 | Gribb | A61B 5/08 |
| 2017/0086672 | A1 | 3/2017 | Tran | |
| 2017/0135417 | A1* | 5/2017 | Lucrecio | A43B 3/34 |
| 2017/0135636 | A1 | 5/2017 | Park et al. | |
| 2017/0273862 | A1* | 9/2017 | Ludlow | A61H 23/00 |
| 2017/0361096 | A1* | 12/2017 | Wingeier | A61B 5/4836 |
| 2019/0150771 | A1* | 5/2019 | Jeong | A61B 7/04 |
| 2019/0365263 | A1* | 12/2019 | Raj | A61B 5/0024 |

FOREIGN PATENT DOCUMENTS

| | | | |
|---|---|---|---|
| JP | 2013039160 | A | 2/2013 |
| JP | 2018023748 | A | 2/2018 |
| KR | 20140029332 | A | 3/2014 |
| KR | 20150066560 | A | 6/2015 |
| WO | 2016127050 | A1 | 8/2016 |
| WO | 2018013656 | A1 | 1/2018 |

OTHER PUBLICATIONS

Liu et al., Epidermal mechano-acoustic sensing electronics for cardiovascular diagnostics and human-machine interfaces, Sci. Adv., 2016.

Gao et al., A system for activity recognition using multi-sensor fusion, IEEE Eng Med Biol Soc, 2011.

USPTO (ISR/US), "International Search Report for PCT/US2019/018318", US, May 1, 2019.

JPO, "First Office Action for JP Application No. 2020-543820", Japan, Nov. 14, 2022.

KIPO, "Office Action for KR Application No. 10-2020-7025489", Korea, Oct. 30, 2023.

* cited by examiner

Wireless Mechano-Acoustic Sensor
Insensitive to the Ambient Environment

- Respiratory signal collected from accelerometer
- Respiratory sound collected from accelerometer

• Respiratory signal collected from accelerometer
• Respiratory sound collected from accelerometer Itch: Experimental Setup

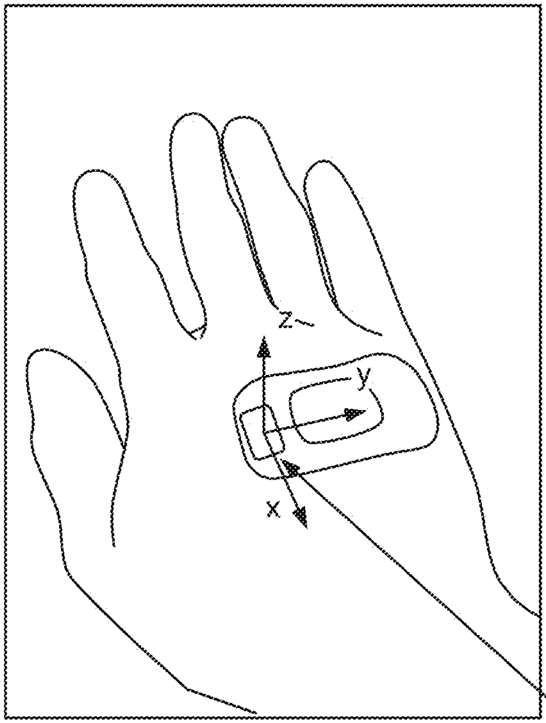

Device on top of hand

Variables
- Scratching antecubital fossa with only index and middle finger, wrist, or elbow
- Scratching in different intensity
- Scratching in different motion path

| Moving Joint | Relative Intensity | Motion |
|---|---|---|
| Finger | Gentle Scratch | Up and Down |
| Wrist | Hard Scratch | Side to Side |
| Elbow | | |

*Rest of the joints are isolated

Location of the Accelerometer (single axis measurement)

FIG. 28

FIG. 33A
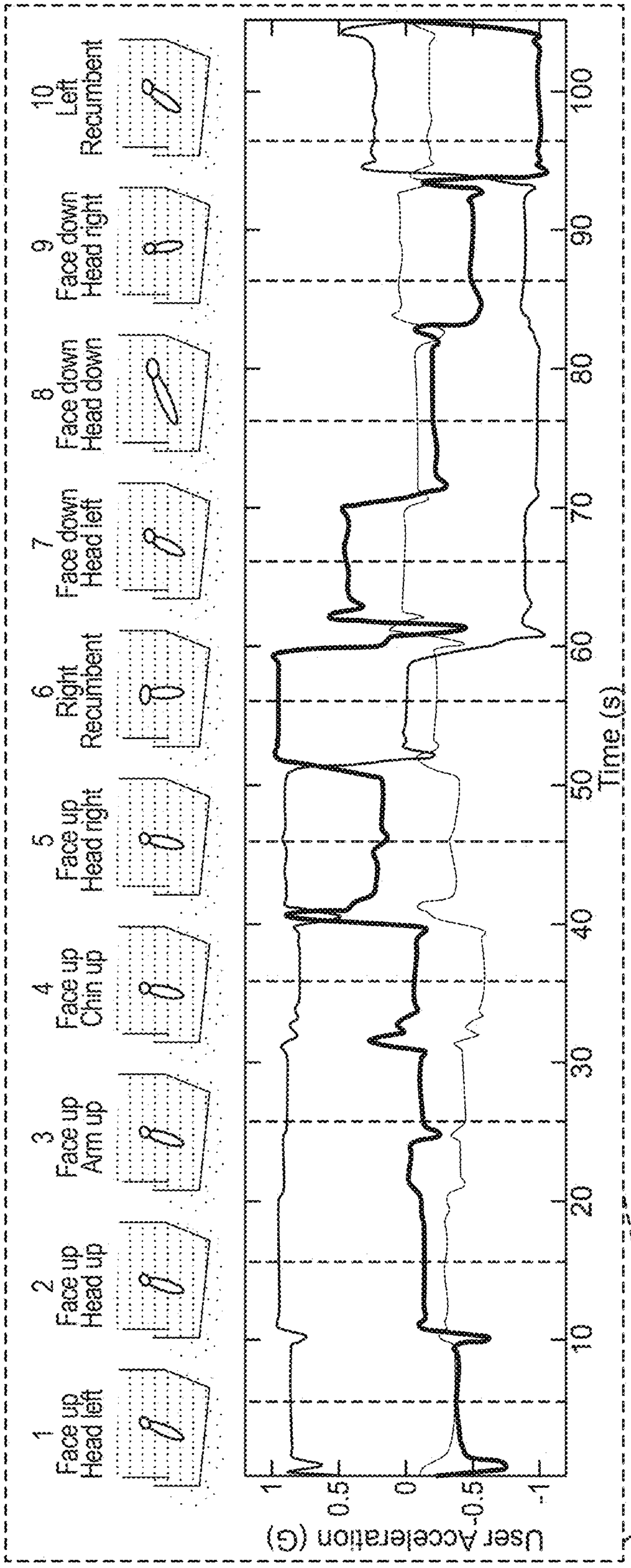
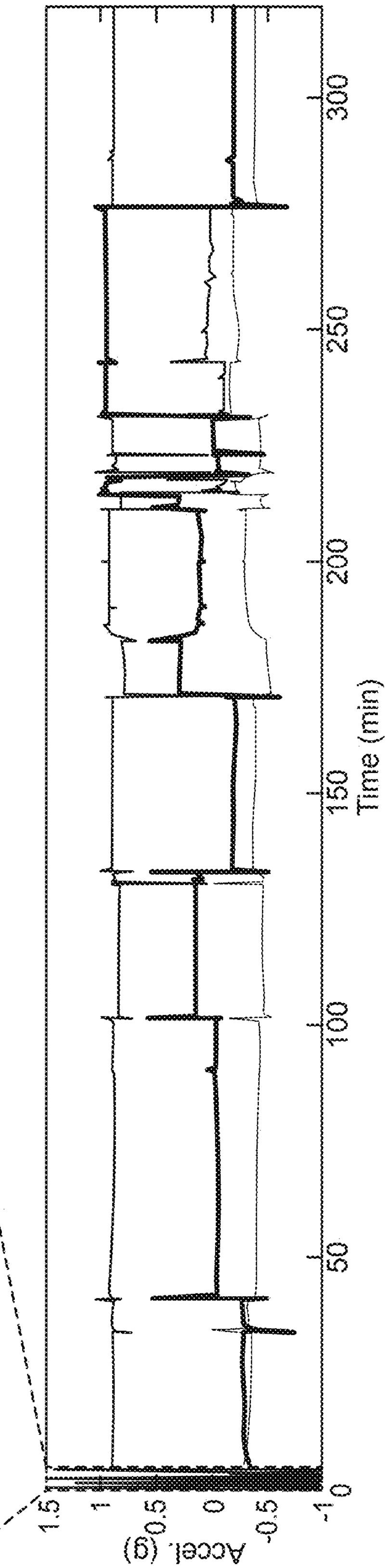
FIG. 33B

| | | |
|---|---|---|
| Accelerometer Time Domain | mean_acc | Mean acceleration magnitude |
| | std_acc | Standard deviation of acceleration magnitude |
| | skew_acc | Skewness of acceleration magnitude |
| | kurt_acc | Kurtosis of acceleration magnitude |
| | sen_acc | Sample entropy of acceleration magnitude |
| Accelerometer Frequency Domain | fmean_acc | Mean frequency magnitude in range 0-30Hz |
| | fstd_acc | Standard deviation of frequency magnitude in range 0-30Hz |
| | fskew_acc | Skewness of frequency magnitude in range 0-30Hz |
| | fkurt_acc | Kurtosis of frequency magnitude in range 0-30Hz |
| | freq_acc | Peak frequency in range 0.5-30Hz |
| Gyroscope Time Domain | mean_gyr | Mean acceleration magnitude |
| | std_gyr | Standard deviation of acceleration magnitude |
| | skew_gyr | Skewness of acceleration magnitude |
| | kurt_gyr | Kurtosis of acceleration magnitude |
| | sen_gyr | Sample entropy of acceleration magnitude |
| Gyroscope Frequency Domain | fmean_gyr | Mean frequency magnitude in range 0-30Hz |
| | fstd_gyr | Standard deviation of frequency magnitude in range 0-30Hz |
| | fskew_gyr | Skewness of frequency magnitude in range 0-30Hz |
| | fkurt_gyr | Kurtosis of frequency magnitude in range 0-30Hz |
| | freq_gyr | Peak frequency in range 0.5-30Hz |

FIG. 38

WIRELESS MEDICAL SENSORS AND METHODS

CROSS-REFERENCE TO RELATED APPLICATIONS

This application claims the benefit of and priority to U.S. Provisional Patent Application Nos. 62/710,324 filed Feb. 16, 2018, 62/631,692 filed Feb. 17, 2018, and 62/753,203 filed Oct. 31, 2018, each of which is specifically incorporated by reference to the extent not inconsistent herewith.

BACKGROUND OF INVENTION

Provided herein are medical sensors, including mechano-acoustic sensing electronics, coupled with on-board microphone and feedback stimuli, including but not limited to vibration motor, speaker, or LED indicator. Systems and methods are provided for mechano-acoustic electrophysiological sensing electronics derived from the body using a 3-axis high frequency accelerometer. The devices are referred herein as soft, flexible, and wearable with advanced power conservation functions and wireless communication capabilities, including being compatible with Bluetooth® enabled systems. Within the system, there is signal processing, signal analysis, and machine learning functionalities that provide a platform for multi-modal sensing for a wide range of physiological and environmental signals that include, but are not limited to: speech, talk time, respiration rate, heart rate, lung volumes, swallowing function, physical activity, sleep quality, movement, eating behaviors. The systems and methods are compatible with use of additional sensors, including one or more of an onboard microphone, pulse oximeter, ECG, and EMG (amongst others).

Mechano-acoustic signals are known to contain essential information for clinical diagnosis and healthcare applications. Specifically, mechanical waves that propagate through the tissues and fluids of the body as a result of natural physiological activity reveal characteristic signatures of individual events, such as the closure of heart valves, the contraction of skeletal muscles, the vibration of the vocal folds, the cycle of respiration, the movement and sound of scratching, and movement in the gastrointestinal tract.

Frequencies of these signals can range from a fraction of 1 Hz (for example, respiratory rate) to 2000 Hz (for example, speech), often with low amplitudes beyond hearing threshold. Physiological auscultation typically occurs with analog or digital stethoscopes, in individual procedures conducted during clinical examinations.

An alternative approach relies on accelerometers in conventional rigid electronic packages, typically strapped physically to the body to provide the necessary mechanical coupling. Research demonstrations include recording of phonocardiography (PCG; sound from the heart), seismocardiography (SCG; vibrations of the chest induced by the beating of the heart), ballistocardiography (BCG; recoil motions associated with reactions to cardiovascular pressure), and sounds associated with respiration.

In the context of cardiovascular health, these measurements yield important insights that complement those inferred from electrocardiography (ECG). For example, structural defects in heart valves manifest as mechano-acoustic responses and do not appear directly in ECG traces.

Previously reported digital measurement methods are useful for laboratory and clinical studies but suffer the following disadvantages: (i) their form factors (rigid designs and large size, for example, 150 mm×70 mm×25 mm) limit the choices in mounting locations and prohibit their practical utility as wearable; (ii) their bulk construction involves physical masses that suppress, through inertial effects, subtle motions associated with important physiological events; (iii) their mass densities and moduli are dissimilar from those of the skin, thereby leading to acoustic impedance mismatches with the skin; and (iv) they offer only a single mode of operation, without the ability, for example, to simultaneously capture ECG and PCG/SCG/BCG signals; (iv) their way of communication to the user interface and data transmission are done via wires tethered to the device and the user interface machine; (v) their power management is through wired connection. The devices and methods provided herein address these limitations in the art.

SUMMARY OF THE INVENTION

Provided herein are methods and devices that provide a telemedicine-type platform, wherein a medical sensor on or implanted in a user provides useful information that can be acted on by a caregiver, such as a medical professional, friend or family member. Not only are the devices and methods useful in diagnostic or therapeutic applications, but can be used for training and rehabilitation. This is reflected in the devices and systems having two-way communication so that information may be sent externally for action to a caregiver and commands received by the medical sensor, including to indicate to a user to take appropriate action, including swallowing, inhalation, exhalation and the like.

The devices and systems can provide real-time output, such as information useful for novel clinical metrics, novel clinical markers, and beneficial endpoints, thereby improving a user's overall health and well-being. The devices and systems are particularly amenable to utilizing off-site cloud storage and analytics that conveniently, reliably and readily can lead to clinician or caregiver action.

The special configuration of hardware, software, bidirectional information flow and remote storage and analysis represents a fundamentally improved platform for medical well-being in a relatively unobtrusive and mobile manner untethered to conventional clinical settings (confined to hospitals or controlled environments, for example). In particular, the software, which may be embedded in a chip or processor, either on-board or remote from the devices described herein, and provide much improved sensor performance and clinically-actionable information. Machine learning algorithms are particularly useful for further improving device performance Specifically included herein, are the appended claims and any other portions of the specification and drawings.

In an aspect, provided is a medical sensor comprising: a) an electronic device having a sensor comprising an accelerometer; and b) a bidirectional wireless communication system electronically connected to the electronic device for sending an output signal from the sensor to an external device and receiving commands from an external controller to the electronic device.

The medical sensor may be wearable, tissue mounted or implantable or in mechanical communication or direct mechanical communication with tissue of a subject. The medical sensor may comprise a wireless power system for powering the electronic device. The medical sensor may comprise a processor to provide a real-time metric. The processor may be on-board with the electronic device or is positioned in an external device that is located at a distance from the medical sensor and in wireless communication with the wireless communication system. The processor may be part of a portable smart device.

The medical sensor may continuously monitor and generate a real-time metric, for example, a social metric or a clinical metric. For example, the clinical metric may be selected from the group consisting of a swallowing parameter, a respiration parameter, an aspiration parameter, a coughing parameter, a sneezing parameter, a temperature, a heart rate, a sleep parameter, pulse oximetry, a snoring parameter, body movement, scratching parameter, bowel movement parameter, a neonate subject diagnostic parameter; a cerebral palsy diagnostic parameter, and any combination thereof. For example, the social metric may be selected from the group consisting of: talking time, number of words, phonatory parameter, linguistic discourse parameter, conversation parameter, sleep quality, eating behavior, physical activity parameter, and any combination thereof.

The medical sensor may comprise a processor configured to analyze the output signal. The processor may utilize machine learning to customize the analysis to each individual user of the medical sensor. The machine learning may comprise one or more supervised learning algorithms and/or unsupervised learning algorithms customizable to the user. The machine learning may improve a sensor performance parameter used for diagnostic sensing or a therapeutic application and/or a personalized user performance parameter.

The processors described herein may be configured to filter and analyze a measured output from the electronic device to improve a sensor performance parameter. The medical sensor may comprise a wireless power system for wirelessly powering the electronic device. The accelerometer may be a 3-axis high frequency accelerometer.

The electronic devices described herein may comprise a stretchable electrical interconnect, a microprocessor, an accelerometer, a stimulator, a resistor and a capacitor in electronic communication to provide sensing of vibration or motion by the accelerometer and a stimulus to a user with the stimulator. The sensor may sense multiple or single physiological signals from a subject; wherein a threshold is used to provide a trigger for a corrective, stimulatory, biofeedback, or reinforcing signal back to the subject.

The electronic devices described herein may comprise a network comprising a plurality of sensors, for example, one sensor may be for sensing said physiological signals from said subject and one sensor may be for providing a feedback signal to said subject.

The threshold may be personalized for said subject. The stimulator may comprise one or more of a vibratory motor, an electrode, a light emitter, a thermal actuator or an audio notification.

The medical sensors described herein may further comprise a flexible encapsulating layer that surrounds the flexible substrate and electronic device. The encapsulating layer may comprise comprises a bottom encapsulating layer and a top encapsulating layer, and a strain isolation layer, wherein the strain isolation layer is supported by the bottom encapsulating layer, and the flexible substrate is supported by the strain isolation layer. There may be an air pocket between the electronic device and the top encapsulating layer. The medical sensor may be configured such that an air pocket does not exist between the electronic device and a bottom layer of the device proximate to or in contact with a tissue surface of a subject.

The medical sensor may have a device mass less than 1 g, less than 500 mg, less than 400 mg, or optionally less than 200 mg and a device thickness less than 10 cm, less than 6 mm, less than 5 mm, or optionally, less than 3 mm.

The medical sensors described herein may be configured for a therapeutic swallow application; a social interaction meter; a stroke rehabilitation device; or respiratory therapeutic device. The medical sensors may be configured to be worn by a user and for use in a therapeutic swallow application, wherein the output signal is for one or more swallow parameters selected from the group consisting of swallow frequency, swallow count, swallow energy. The medical sensor may further comprise a stimulator that provides a haptic signal to a user to engage in a safe swallow. The safe swallow may be determined by sensing onset of inspiration and expiration of a user respiratory cycle. One or more machine learning algorithms may be used in a feedback loop for optimization of the haptic signal timing.

The medical sensors described herein may be configured to be worn by a user and for use as a social interaction meter, wherein the output signal is for one or more social parameters selected from the group consisting of: talking time, number of words (fluency rate), phonatory parameter, linguistic discourse parameter or conversation parameter. The medical sensor may be configured for mounting to a suprasternal notch of the user. The medical sensor may be for use with one more additional user well-being parameters selected from the group consisting of sleep quality, eating behavior and physical activity, wherein the medical sensor social parameters and well-being parameters are combined to provide a social interaction metric.

The medical sensor may comprise a stimulator that provides a haptic signal to a user to engage in a social interaction event. The medical sensor may be configured to be worn by a user and for use in a stroke rehabilitation device, wherein the output signal is for a social parameter and/or a swallow parameter. The medical sensor may be for use with one or more additional stroke rehabilitation parameters selected from the group consisting of: gait, falls and physical activity. The medical sensor may comprise a stimulator that provides a haptic signal to a user to engage in a safe swallowing event.

The medical device may be configured to be worn by a user and for use in a respiratory therapeutic device, wherein the output signal is for respiratory inspiration and/or expiration: effort, duration, or airflow through the throat. The medical device may comprise a stimulator that provides a haptic signal to a user to engage in respiratory training.

The medical devices described herein may comprise an external sensor operably connected to the electronic device. The external sensor may comprise: a microphone and/or a mouthpiece.

The medical sensors described herein may be capable of reproducing an avatar or video representation of body position and movement of a subject across time.

In an aspect, provided is a method of measuring a real-time personal metric using any of the medical sensors described herein.

In an aspect provided is a method of measuring a real-time personal metric the method comprising the steps of: a) mounting any of the devices of the above claims to a user skin surface or implanting subdermally; b) detecting a signal generated by the user with the sensor; c) analyzing the filtered signal to thereby classify the filtered signal; and d) providing a real-time metric to the user or a third-party based on the classified filtered signal.

The described methods may comprise a step of filtering the detected signal before the analyzing step. The providing step may comprise one or more of: providing a haptic stimulus to the user; storing or displaying a clinical metric; and/or storing or displaying a social metric. The providing step may further comprise storing the real time metric on a remote server for subsequent analysis to generate a clinician or caregiver action. The action may comprise sending a command to the medical sensor.

The real time metric may be a mental, physical or social metric related to health. The analyzing step may comprise use of a machine learning algorithms. The machine learning algorithm may comprise an independent supervised learning algorithm, wherein each algorithm is independently trained to provide a personalized real-time metric specific for an individual user.

The personalized real time personal metric may be for a therapeutic or diagnostic application. The therapeutic or diagnostic application may be selected from the group consisting of: safe swallowing; respiratory therapy; cerebral palsy diagnosis or therapy; and a neonate diagnosis or therapy.

The real time personal metric may be for a medical application selected from the group consisting of: sleep medicine; dermatology; pulmonary medicine; social interaction evaluation; speech therapy; dysphagia; stroke rehabilitation; nutrition; obesity treatment; fetal monitoring; neonate monitoring; cerebral palsy diagnosis; maternal monitoring; bowel function; diagnosis or treatment of sleeping disorder; sleep therapy; injury; injury prevention falls or over extension of joints or limbs; injury prevention in sleep; firearm/ballistic related injuries; and cardiac output monitoring.

In an aspect, provided is a medical sensor comprising an electronic device having a sensor comprising an accelerometer; and a wireless communication system electronically connected to the electronic device.

The wireless communication system may be a bidirectional wireless communication system. The wireless communication system may be for sending an output signal from the sensor to an external device. The wireless communication system may be for receiving commands from an external controller to the electronic device.

The medical sensors described herein may be wearable or implantable. The medical sensors may comprise a wireless power system for powering the electronic device. The medical sensors may comprise a processor to provide a real-time metric. The processor may be on-board with the electronic device or is positioned in an external device that is located at a distance from the medical sensor and in wireless communication with the wireless communication system. The processor may be part of a portable smart device.

The medical sensors described herein may continuously monitor and generate a real-time metric. The real-time metric may be a social metric or a clinical metric. The clinical metric may be selected from the group consisting of a swallowing parameter, a respiration parameter, an aspiration parameter, a coughing parameter, a sneezing parameter, a temperature, a heart rate, a sleep parameter, pulse oximetry, a snoring parameter, body movement, scratching parameter, bowel movement parameter, and any combination thereof.

The social metric may be selected from the group consisting of: talking time, number of words, phonatory parameter, linguistic discourse parameter, conversation parameter, sleep quality, eating behavior, physical activity parameter, and any combination thereof.

The medical sensors described herein may comprise a processor configured to analyze the output signal. The processor may utilize machine learning to customize the analysis to each individual user of the medical sensor. The machine learning may comprise one or more supervised learning algorithms and/or unsupervised learning algorithms customizable to the user. The machine learning may improve a sensor performance parameter used for diagnostic sensing or a therapeutic application and/or a personalized user performance parameter.

The described sensors may be provided on or proximate to a suprasternal notch of a subject. The described sensors may be provided on or proximate to a mastoid process of a subject. The described sensors may be provided on or proximate to a neck of a subject. The described sensors may be provided on or proximate to a lateral neck of a subject. The described sensors may be provided on or proximate to a under the chin of a subject. The described sensors may be provided on or proximate to the jaw line of a subject. The described sensors may be provided on or proximate to the clavicle of a subject. The described sensors may be provided on or proximate to a bony prominence of a subject. The described sensors may be provided behind the ear of a subject.

The described electronic devices may comprise one or more three-axis high frequency accelerometers. The described electronic devices may comprise a mechano-acoustic sensor. The described electronic devices may comprise one or more of an onboard microphone, ECG, pulse oximeter, vibratory motors, flow sensor, and pressure sensor.

The described electronic devices may be a flexible device and/or a stretchable device. The described electronic devices may have a multilayer floating device architecture. The described electronic devices may be at least partially supported by an elastomer substrate, superstrate or both. The described electronic devices may be is at least partially supported by a silicone elastomer providing for strain isolation.

The described electronic devices may be at least partially encapsulated by a moisture resistant enclosure. The described electronic devices may further comprise an air pocket.

The wireless communication systems described herein may be a Bluetooth communication module. The wireless communication systems described herein may be powered by a wireless re-chargeable system. The wireless re-chargeable system may comprise one or more of a rechargeable battery, an inductive coil, a full wave rectifier, a regulator, a charging IC and PNP transistor.

The medical sensors described herein may comprise a gyroscope, for example, a 3-axis gyroscope. The medical sensors described herein may comprise a magnetometer, for example, for measuring the electric field generated by a patient's respiration. The medical sensors described herein may be mounted proximate to a suprasternal notch of a patient.

In an aspect, provided is a device comprising: an electronic device having a sensor comprising an accelerometer; a bidirectional wireless communication system electronically connected to the electronic device for sending an output signal from the sensor to an external device and receiving commands from an external controller to the electronic device; wherein the sensor senses multiple or single physiological signals from a subject that provides the basis of one or more corrective, stimulatory, biofeedback, or reinforcing signals provided to the subject.

The corrective, stimulatory, biofeedback, or reinforcing signals may be provided by one or more actuators. The one or more actuators may be thermal, optical, electrotactile, auditory, visual, haptic or chemical actuators operationally connected to said subject. The device may comprise a processor for providing feedback control of said one or more corrective, stimulatory, biofeedback, or reinforcing signals provided to the subject.

The multiple or single physiological signals may provide input for said feedback control. The feedback control may include a thresholding step for triggering said one or more corrective, stimulatory, biofeedback, or reinforcing signals provided to the subject. The thresholding step may be achieved by dynamic thresholding.

In an aspect, provided is a device comprising: an electronic device having a multi-modal sensor system comprising a plurality of sensors; wherein said sensors comprise an accelerometer and at least one sensor that is not an accelerometer; and a bidirectional wireless communication system electronically connected to the electronic device for sending an output signal from the sensor to an external device and receiving commands from an external controller to the electronic device.

The sensor system may comprise one or more sensor selected from the group consisting of an optical sensor, an electronic sensor, a thermal sensor, a magnetic sensor, an optical sensor, a chemical sensor, an electrochemical sensor, a fluidic sensor or any combination of these. The sensor system may comprise one or more sensors selected from the group consisting of a pressure sensor, an electrophysiological sensor, a thermocouple, a heart rate sensor, a pulse oximetry sensor, an ultrasound sensor, or any combination of these.

In an aspect, provided is a device comprising: an electronic device having a sensor comprising an accelerometer; and one or more actuators operationally connected to said sensor; wherein the sensor senses multiple or single physiological signals from a subject that provides the basis of one or more corrective, stimulatory, biofeedback, or reinforcing signals provided to the subject by said one or more actuators.

The one or more corrective, stimulatory, biofeedback, or reinforcing signals may be one or more optical signals, electronic signals, thermal signals, magnetic signals, chemical signals, electrochemical signals, fluidic signals, visual signals, mechanical signals or any combination of these.

The one or more actuators may be selected from the groups consisting of a thermal actuator, optical actuator, electrotactile actuator, auditory actuator, visual actuator, haptic actuator, mechanical actuator, or chemical actuators operationally connected to said subject. The one or more actuators may be one or more stimulators. The one or more actuators may be a heater, a light emitter, a vibrating element, a piezoelectric element, an sound generating element, a haptic element or any combination of these.

A processor may be operationally connected to said electronic device and said one or more actuators; wherein said processor provides for feedback control of said one or more corrective, stimulatory, biofeedback, or reinforcing signals provided to the subject. The multiple or single physiological signals may provide input for said feedback control.

The feedback control may include a thresholding step for triggering said one or more corrective, stimulatory, biofeedback, or reinforcing signals provided to the subject. The thresholding step may be achieved by dynamic thresholding.

The described devices may comprise a bidirectional wireless communication system electronically connected to the electronic device for sending an output signal from the sensor to an external device and receiving commands from an external controller to the electronic device. The corrective, stimulatory, biofeedback, or reinforcing signals may be provided to the subject for training or therapy. The training or therapy may be for respiratory or swallowing training.

The described devices may continuously monitor and generate a real-time metric. The real-time metric may be a social or clinical metric. The clinical metric may be selected from the group consisting of a swallowing parameter, a respiration parameter, an aspiration parameter, a coughing parameter, a sneezing parameter, a temperature, a heart rate, a sleep parameter, pulse oximetry, a snoring parameter, body movement, scratching parameter, bowel movement parameter, a neonate subject diagnostic parameter; a cerebral palsy diagnostic parameter, and any combination thereof. The social metric may be selected from the group consisting of: talking time, number of words, phonatory parameter, linguistic discourse parameter, conversation parameter, sleep quality, eating behavior, physical activity parameter, and any combination thereof.

The described devices may comprise a gyroscope, for example, a 3-axis gyroscope. The described devices may comprise a magnetometer.

In an aspect, provided is a method of diagnosis using any of the devices or sensors described herein.

In an aspect, provided is a method of training a subject using any of the devices or sensors described herein.

Additionally, the configuration of sensors provided may be used in conjunction to provide more precise measurements or metrics. For example, an accelerometer may be used in conjunction with a mechano-acoustic sensor for measuring a user's scratching. Scratching motion can be detected by the accelerometer, but other common motion (e.g. waving, typing) can be difficult to distinguish from scratching. The incorporation of an acoustic sensor proximate to the skins allows for secondary classification and improves data collection.

Differential measurement of separate areas of a patient's body may also be useful in improving data collection and accuracy. In some cases a single device may measure two different areas by being positioned on a biological boundary, in some cases, multiple devices may be used. For example, placement of a device on the suprasternal notch allows for accelerometric measurement of both the chest and neck. During respiration, there is a high degree of motion in the chest while the neck remains relatively static. This leads to more robust measurement and assessment using the devices described herein.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

BRIEF DESCRIPTION OF THE DRAWINGS

FIG. 28 provides an example configuration for measuring patient scratching using an epidermal mechano-acoustic-electrophysiological measurement/therapeutic device.

FIG. 30A provides a schematic illustrating potential mounting locations (schematically shown by superimposed boxes) on a subject. FIG. 30B provides photographs and schematics illustrating device placements on a subject including proximate to the lateral neck and proximate to the suprasternal notch. FIGS. 30C and 30D provide exemplary signals for X, Y and Z dimensions corresponding to the activity of a subject including holding breath, sitting talking, leaning, walking and jumping.

FIG. 31A provides a flow diagram corresponding to signal processing approach for the analysis of 3-axis accelerometer output. FIG. 31B provides exemplary signals corresponding to the activity of a subject.

FIG. 32A provides exemplary data for respiration rate GS vs. MA corresponding to a range of subjects. FIG. 32B provides exemplary data for heart rate GS vs. MA corresponding to a subject. FIG. 32C provides exemplary data for talking time GS vs. MA corresponding to a range of subjects. FIG. 32D provides exemplary data for swallow counts GS vs. MA corresponding to a range of subjects.

FIGS. 33A-33D. FIGS. 33A-33B provide exemplary signals corresponding to the activity of a subject including various configurations of face and head up and down movements. FIG. 33C provides a plot of rotation angle vs. time (min). FIG. 33D provides a plot of heart rate (BPM) vs. time (min).

FIG. 34A provides a schematic illustrating a research-grade wearable sensor of the invention incorporating a 3-axis accelerometer, gyroscope, and EMG detector into a multilayer, flexible device format. FIG. 34B provides a schematic showing a plurality of wearable sensors (5 in total) provide on different regions for a neonate subject including the limbs and trunk. In an embodiment, the sensors are provided on the neonate subject during 1-hour clinical visits. FIG. 34C provides accelerometer and gyroscope data acquired from the sensors.

FIG. 35A provides a schematic of a sensor of this embodiment, showing EMG and accelerometer modules and Bluetooth communication module. FIGS. 35B-35D provide examples of data acquired from a sensor including acceleration, reconfigured 3D motion and EMG.

FIG. 38 provides examples of data analytics useful for analyzing the output of sensors of the present example, for example, for clinical diagnostic applications.

FIG. 43A. Demonstration of device flexibility. FIG. 43B. Exploded view of floating device architecture. FIG. 43C. Wireless system operation architecture. FIG. 43D. Simulation of system level device deformation. FIG. 43E. System level device deformation.

FIG. 44A. A total of 60-second data capturing various of bioactivities. FIG. 44B. Sample time series, spectrogram, and spectrum information for heartbeat, talking, swallowing, and walking signals.

FIG. 45A. Block diagram of post-processing analytics for energy intensity (EI), heart rate (HR), respiration rate (RR), swallow count (SC) and talking time (TT). FIG. 45B. Detection of heartbeat peaks as local maximum of the 20-50 Hz band-passed waveform. FIG. 45C. Decoupling chest-wall motion from three-axis measurement and zero-crossing nodes counting for RR estimation. FIG. 45D. The talking signal features high-quality harmonics of fundamental frequencies in the range from 85 to 255 Hz for typical adults. FIG. 45E. Post zeroing talking and motion signals, the broadband swallow events are detected when both high-passed and low-passed signals exceed quiet-time limits simultaneously.

FIG. 47A. Image of the device on the suprasternal along with gold standard sleep sensors ensemble, including electrocardiogram (ECG), Pressure Transducer Airflow (PTAF), Abdomen Strain Gauge, Thorax Strain Gauge, Thermistor, Electroencephalography (EEG), and Electrooculography (EOG). FIG. 47B. Demonstration of the body orientation detection using the three-axis acceleration data. FIG. 47C. Comparisons of the heart rate measurement from the mechano-acoustic sensor with the electrocardiogram (EKG) measurement during sleep. FIG. 47D. Comparisons of the respiration rate measurement from the mechano-acoustic sensor with the nasal Pressure Transducer Airflow (PTAF), and Thorax Strain Gauge measurements during sleep. FIG. 47E. Comparisons of the body orientation measurement from the mechano-acoustic sensor with the visual inspection. FIG. 47F. Inference of the sleep stages based on the HR and RR values from the accelerometer in comparison with the clinical-inspected sleep stages. FIG. 47G. Cumulative Distribution Function as a function of heart rate and respiration rate. FIG. 47H. Example interface for Summary Statistics.

FIG. 49A simulation demonstrating wavelet cross spectrum analysis for differential mode signal extraction. FIG. 49B. Zero-crossing nodes count on sample data.

FIG. 50A Accelerometer measurement of quiet-time respiration signal in comparison with the Electrocardiography (ECG) measurement. FIG. 50B The HR measurement in comparison with the polar monitor measurement. The cardiac amplitude exhibits a linear correlation with the HR measurement.

FIG. 53A Subject 1. FIG. 53B Subject 2.

FIG. 54A Schematic of the double layer serpentine interconnects with the arc angle of 270°. FIG. 54B Relationship between the arc angle and elastic stretchability of the pre-compressed serpentine interconnects and plane serpentine interconnects.

FIG. 55A 40% compression before yielding. FIG. 55B 160° bending before yielding FIG. 56. Tensile deformation of the system level device and the effect of strain isolation layer. Strain isolation minimizes the resistance of the silicone substrate deformation from the rigid islands of electronics as compared to system without isolation layer.

DETAILED DESCRIPTION OF THE INVENTION

Figure 1:
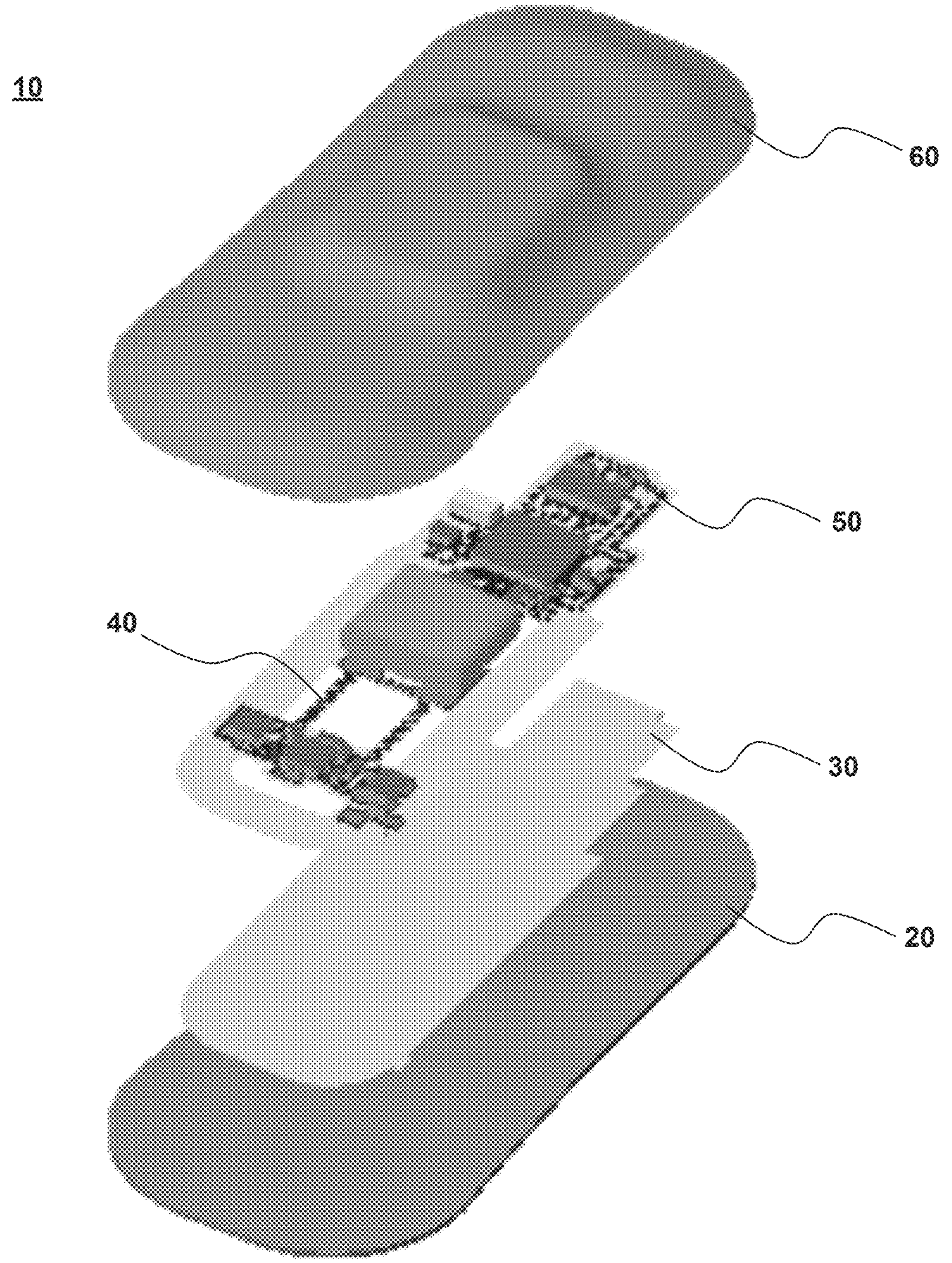
FIG. 1 provides an example exploded view schematic of a epidermal mechano-acoustic-electrophysiological measurement device.

In general, the terms and phrases used herein have their art-recognized meaning, which can be found by reference to standard texts, journal references and contexts known to those skilled in the art. The following definitions are provided to clarify their specific use in the context of the invention.

"Mechano-acoustic" refers to any sound, vibration or movement by the user that is detectable by an accelerometer. Accordingly, accelerometers are preferably high frequency, three-axis accelerometers, capable of detecting a wide range of mechano-acoustic signals. Examples include respiration, swallowing, organ (lung, heart) movement, motion (scratching, exercise, movement), talking, bowel activity, coughing, sneezing, and the like.

"Bidirectional wireless communication system" refers to onboard components of the sensor that provides capability of receiving and sending signals. In this manner, an output may be provided to an external device, including a cloud-based device, personal portable device, or a caregiver's computer system. Similarly, a command may be sent to the sensor, such as by an external controller, which may or may not correspond to the external device. Machine learning algorithms may be employed to improve signal analysis and, in turn, command signals sent to the medical sensor, including a stimulator of the medical sensor for providing haptic signal to a user of the medical device useful in a therapy. More generally, these systems may be incorporated into a processor, such as a microprocessor located on-board or physically remote from the electronic device of the medical sensor.

"Real-time metric" is used broadly herein to refer to any output that is useful in medical well-being. It may refer to a social metric useful in understanding a user's social well-being. It may refer to a clinical metric useful in understanding or training a biological function, such as breathing and/or swallowing.

"Customized machine learning" refers to the analysis of the output from the sensor that is tailored to the individual user. Such a system recognizes the person-to-person variabilities between users, including by medical condition (stroke versus dementia), weight, baseline fluency, resting respiratory rate, base heart rate, etc. By specifically tailoring the analysis to individual users, great improvement in the sensor output and what is done downstream by a caregiver is achieved. This is referred herein as generally an improvement in a "sensor performance parameter". Exemplary parameters include accuracy, repeatability, fidelity, and classification accuracy, for example.

"Proximate to" refers to a position that is nearby another element and/or location of a subject such as a human subject. In an embodiment, for example, proximate is within 10 cm, optionally for some applications within 5 cm, optionally for some applications within 1 cm, of another element and/or location on a subject.

In some embodiments, the sensor systems of the inventor are wearable, tissue mounted or implantable or in mechanical communication or direct mechanical communication with tissue of a subject. As used herein mechanical communication refers to the ability for the present sensors to interface directly or indirectly with the skin or other tissue in a conformable, flexible, and direct manner (e.g., there is no air gap) which in some embodiments allows for deeper insights and better sensing with less motion artifact compared to accelerometers strapped to the body (wrists or chest).

Various embodiments of the present technology generally relate sensing and a physical feedback interface, including a "mechano-acoustic" sensing. More specifically, some embodiments of the present technology relate to systems and methods for mechano-acoustic sensing electronics configured for use in respiratory diagnostics, digestive diagnostics, social interaction diagnostics, skin irritation diagnostics, cardiovascular diagnostics and human-machine-interface (HMIs).

Physiological mechano-acoustic signals, often with frequencies and intensities that are beyond those associated with the audible range, can provide information of great clinical utility. Stethoscopes and digital accelerometer in conventional packages can capture some relevant data, but neither is suitable for use in a continuous, wearable mode, typical non-stationary environment, and both have shortcomings associated with mechanical transduction or signal through the skin.

Various embodiments of the present technology include a soft, conformal, stretchable class of device configured specifically for mechano-acoustic recording from the skin, capable of being used on nearly any part of the body, in forms that maximize detectable signals and allow for multimodal operation, such as electrophysiological recording, and neurocognitive interaction.

Experimental and computational studies highlight the key roles of low effective modulus and low areal mass density for effective operation in this type of measurement mode on the skin. Demonstrations involving seismocardiography and heart murmur detection in a series of cardiac patients illustrate utility in advanced clinical diagnostics. Monitoring of pump thrombosis in ventricular assist devices provides an example in characterization of mechanical implants. Tracking of swallowing trend of normal relative to the breathing cycle presents new understanding of natural physical behaviors. Measuring the movement and listening to the sound of respiratory, circulatory, digestive system, and even typical movement such as scratching simultaneously with single device provides entire new dimension of the pathological diagnostics. Speech recognition and human-machine interfaces represent additional demonstrated applications. These and other possibilities suggest broad-ranging uses for soft, skin-integrated digital technology that can capture human body acoustics. Physical feedback system integrated with the sensor delivers the additional therapeutic functionality to the device.

In the following description, for the purpose of explanation, numerous specific details are set forth in order to provide a thorough understanding of embodiments of the present technology. It will be apparent, however, to one skilled in the art that embodiments of the present technology may be practiced without some of these specific details. While, for convenience, embodiments of the present technology are described with reference to cardiovascular diagnostics, respiration and swallowing correlation, and scratching intensity detection, the present technology provides many other uses in a wide variety of potential technical fields.

The techniques introduced here can be embodied as special purpose hardware (e.g. circuitry) as programmable circuitry appropriately programmed with software and/or firmware, or as a combination of special-purpose and programmable circuitry. Hence, embodiment may include a machine-readable medium having stored thereon instructions which may be used to program a computer (or other electronic devices) to perform a process. The machine-readable medium may include, but is not limited to, floppy diskettes, optical disks, compact disc read-only memories (CD-ROMs), magneto-optical disks, ROMs, random access memories (RAMs), erasable programmable read-only memories (EPROMs), electrically erasable programmable read-only memories (EEPROMs), magnetic or optical cards, flash memory, or other type of media/machine-readable medium suitable for storing electronic instructions.

The phrases "in some embodiments," "according to some embodiments," "in the embodiments shown," "in other embodiments," and the like generally mean the particular feature, structure, or characteristics following the phrase is included in at least one implementation of the present technology, and may be included in more than one implementation. In addition, such phrases do not necessarily refer to the same embodiments or different embodiments.

FIG. 1 illustrates an exploded view diagram of an example of a medical device 10, such as an epidermal mechano-acoustic-electrophysiological measurement device, according to some embodiment of the present technology.

In this example embodiment, an epidermal mechano-acoustic-electrophysiological measurement device comprises: a lower elastomeric shell 20, silicone strain isolation layer 30, stretchable interconnects 40, electronic devices 50 such as microprocessor, accelerometers, vibration motor, resistors, capacitors, and the like, and an upper elastomeric shell 60.

Figure 2:
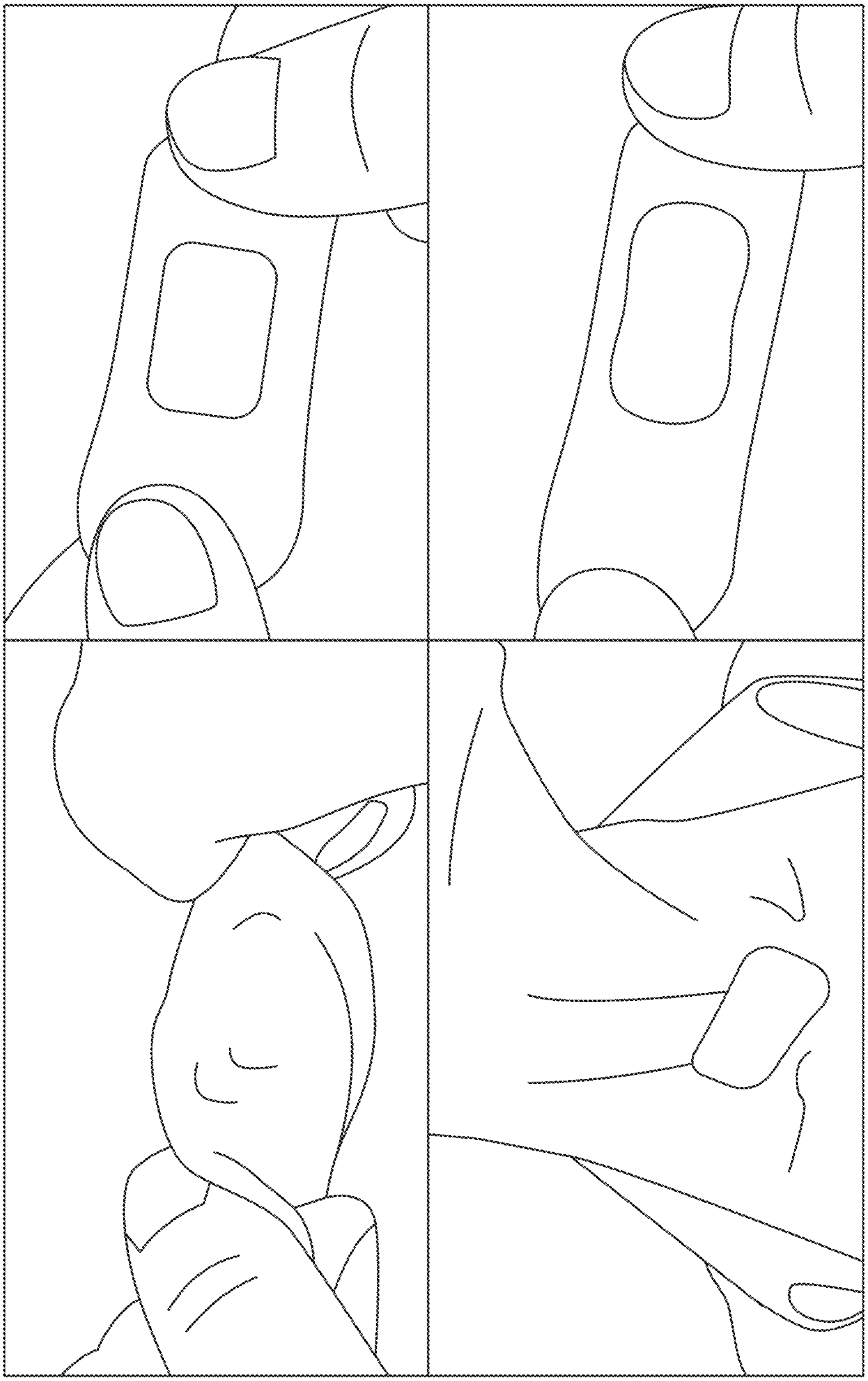
FIG. 2 provides an example of a wearable (e.g., epidermally mounted) mechano-acoustic electrophysiological measurement device as provided in FIG. 1.

FIG. 2 illustrates an example of a wearable (e.g., epidermally mounted) mechano-acoustic electrophysiological measurement device according to some embodiments of the present technology. This example assembly, includes the example epidermal mechano-acoustic-electrophysiological measurement device of FIG. 1, along with a stimulator, such as a vibration motor.

The present technology provides a different type of mechano-acoustic-electrophysiological sensing platform that exploits the most advanced concepts in flexible and stretchable electronics to allow soft, conformal integration with the skin without any requirement of wire connection to the device. The technology allows precision recordings of vital physiological signals in ways that bypass many of the limitations of conventional technologies (e.g. heavy mass and bulky package) with the freedom of application environment. The mechano-acoustic modality includes miniaturized, low-power accelerometers with high sensitivity (16384 LSB/g) and large frequency bandwidth (1600 Hz) with possible augmentation of its functional limitation. Soft, strain-isolating packaging assemblies, together with electronics for electrophysiological recording and active feedback system represent other example features of these stretchable systems. Example embodiments of the present technology have a mass of 300 mg (or less than 600 mg, or between 100 mg and 500 mg), a thickness of 4 mm (or between about 3 mm and 5 mm), effective moduli of 100 kPa (in both the x and y direction) (or between about 50 kPa and 200 kPa), which correspond to values that are orders of magnitude lower than those previously reported. In this manner, any of the medical devices provided herein may be described as conformable, including conformable to the skin of a user. Such physical device parameters ensure the device is not unduly uncomfortable and can be worn for long periods of time.

Example embodiments of the present technology provide qualitative improvements in measurement capabilities and wearability, in formats that can interface with nearly any region of the body, including curvilinear parts of the neck to capture signals associated with respiration, swallowing, and vocal utterances, with completely wireless form factor that can transfer, communicate, and power wirelessly. The following description and figures illustrate properties of this technology and demonstrates its utility in wide-ranging examples, from human studies on patients to personal health monitoring/training devices with customizable applications.

Specific data show simultaneous recording of gait, respiration, heart activity, breathing cycle, and swallowing. Also, vibrational acoustics of ventricular assist devices (VADs) (that is, devices used to augment failing myocardial function, through often complicated by intradevice thrombus formation) can be captured and used to detect pump thrombosis or device malfunction.

In addition, applications exist in speech recognition and classification for human-machine interfaces, in modes that capture vibrations of the larynx without interference from noise in the ambient environment. Baseline studies on the biocompatibility of the skin interface and on the mechanical properties and fundamental aspects of the interface coupling provide additional insights into the operation of the present technology.

Also, the device's functionality in interacting with patients through stimuli integrated in sensor allows it to be therapeutic device. Having the device in wireless form factor and personal use as well as clinical use, large data is collected. With machine learning, the devices not only utilize stimuli as output based on the scheduled moment, but also as input for the study of mechano-acoustic signal associated with the physiological responses.

Figure 3:
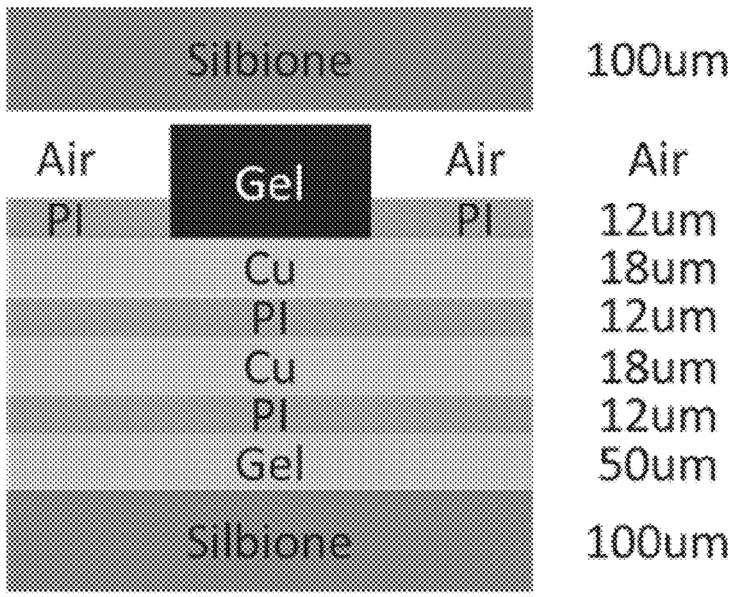
FIG. 3 provides a device cross-section of a wearable epidermal mechano-acoustic-electrophysiological measurement/therapeutic device including thickness and modulus information.

FIG. 3 illustrates a device cross-section of an example of a medical device, including a wearable epidermal mechano-acoustic-electrophysiological measurement/therapeutic device according to some embodiments of the present technology including thickness and modulus information.

Figure 4:
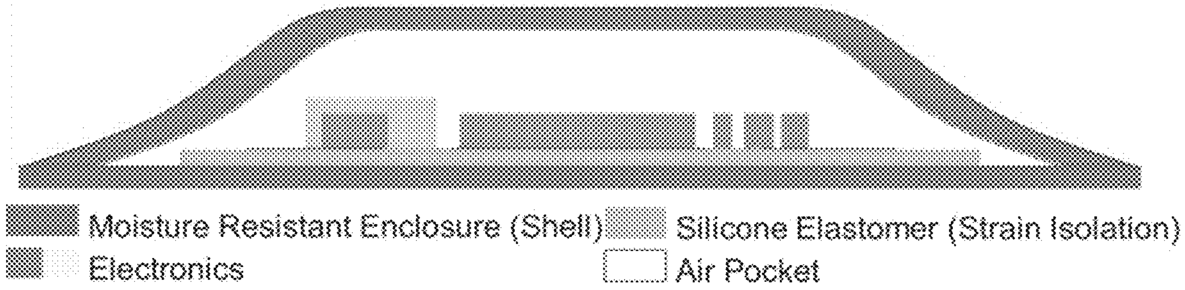
FIG. 4 provides a side view of an example epidermal mechano-acoustic-electrophysiological measurement/therapeutic device illustrating the various layers described herein. The thin membrane (300 mm) of low modulus and highly resilient silicone (Ecoflex Smooth-on, E=60 kPa) surrounds the electronics without making any physical interface with them.

Referring to FIG. 4, each layer of the example epidermal mechano-acoustic-electrophysiological measurement/therapeutic device is described in further detail. The lower elastomeric shell comprises a 100 μm layer of Silbione having a modulus of 100 kPa. The silicone gel layer between the device and shell comprises a 50 μm layer of Silbione Gel having a modulus of 5 kPa. The stretchable interconnect comprises double layer of serpentine copper trace 18 μm thick each encapsulated between two 12 μm layer of polyimide (PI) having a modulus of 2.5 GPa. The electronic devices are bonded to the stretchable interconnects, then covered with the upper elastomeric shell comprises a 100 μm layer of Silbione containing an air pocket between the electronics and the upper elastomeric shell.

The fabrication process involves five parts: (i) production of the of the flexible PCB (fPCB) device platform; (ii) chip-bonding onto the fPCB device platform; (iii) casting the top and bottom elastomeric shells from molds; (iv) layering the silbione gel; (v) bonding the top and bottom elastomeric shells.

The following describes the fabrication process in more detail: (i) Photolithography and metal etching process, or laser cutting process defines a pattern of interconnects in the copper. Spin-coating and curing process yields a uniform layer of PI on the resulting pattern. Photolithography and reactive ion etching (RIE, Nordson MARCH) define the top, middle, and bottom layers of PI in geometries matching those of the interconnects. (ii) Chip bonding process assembles the necessary electronic components for the device to operate. (iii) Pairs of recessed and protruded molds for each of top and bottom elastomeric shells define the shape of the outer structure of the device. (iv) Recessed region in the bottom shell contains the layer of Silbione gel for both bonding and strain isolating purpose of the device platform. (v) Bonding the curved thin top elastomeric membrane shells with the flat bottom elastomeric shells packages the electronic components along with the air pocket.

Figure 5:
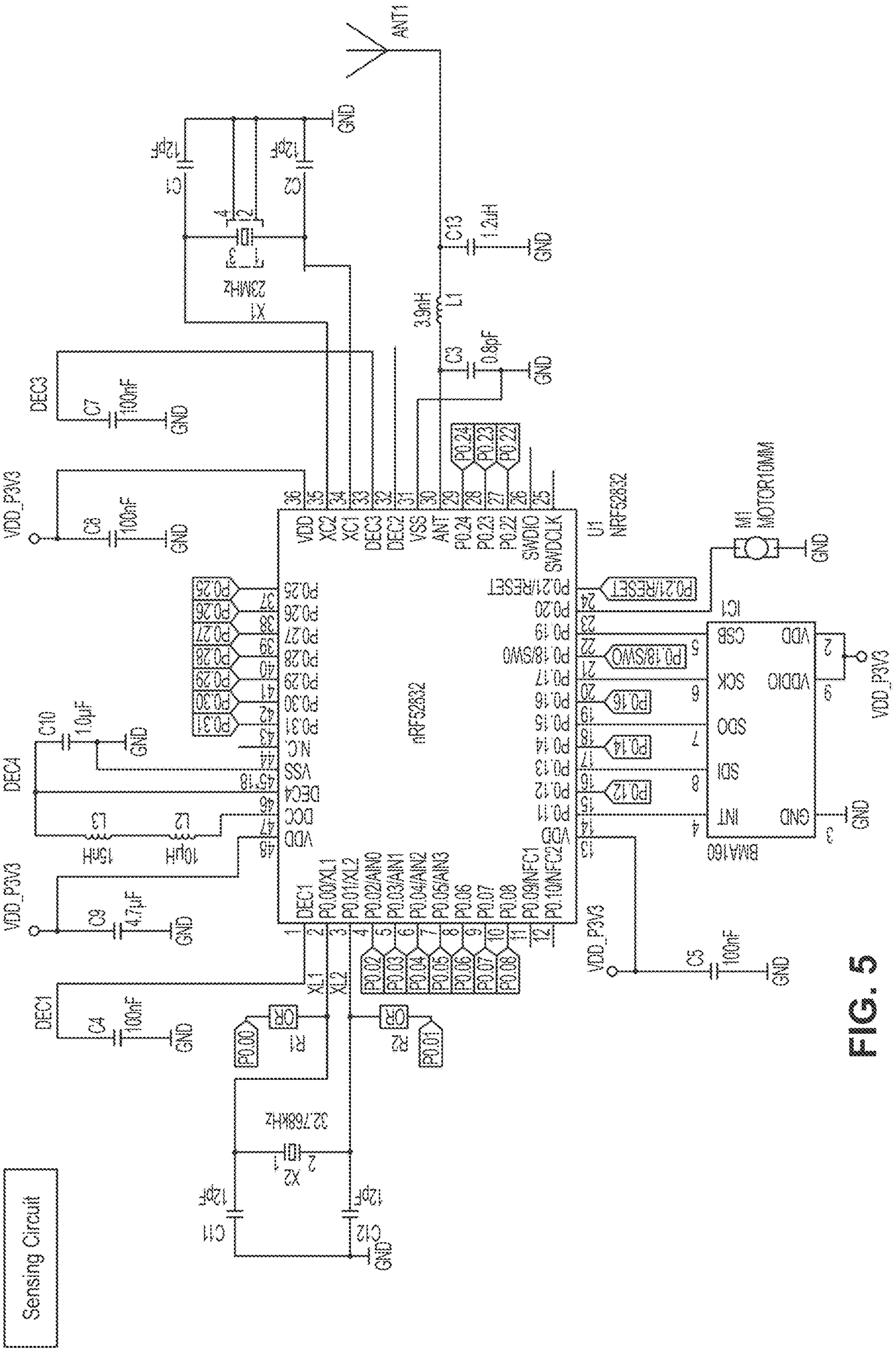
FIG. 5 provides an example sensing circuit diagram of an epidermal mechano-acoustic-electrophysiological measurement/therapeutic device.

FIG. 5 illustrates a sensing circuit diagram of an example of an epidermal mechano-acoustic-electrophysiological measurement/therapeutic device according to some embodiments of the present technology.

The sensing circuit comprises a mechano-acoustic sensor (BMI160, Bosch), coin cell motor and Bluetooth capable microcontroller (nRF52, Nordic Semiconductor). The sensor has a frequency bandwidth (1600 Hz) that lies between the range of targeted respiration, heart, scratching, and vocal fold movements and sounds. Additional sensors within the platform may include but are not limited to the following: onboard microphone, ECG, pulse oximeter, vibratory motors, flow sensor, pressure sensor.

Figure 6:
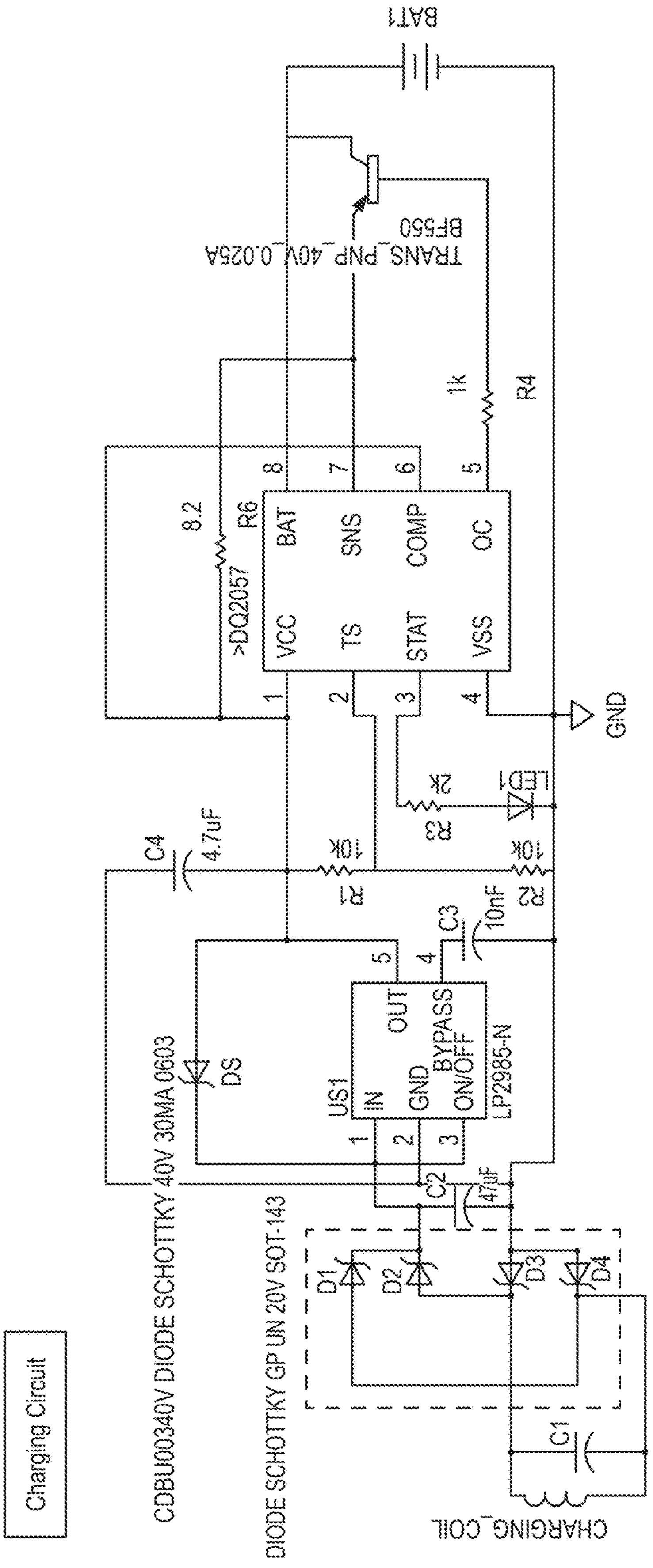
FIG. 6 provides an example charging circuit diagram of an epidermal mechano-acoustic-electrophysiological measurement/therapeutic device.

FIG. 6 illustrates a charging circuit diagram of an example of an epidermal mechano-acoustic-electrophysiological measurement/therapeutic device according to some embodiments of the present technology.

The wireless charging circuit comprises an inductive coil, full wave rectifier (HSMS-2818, Broadcom), regulator (LP2985-N, Texas Instruments), charging IC (BQ2057, Texas Instruments), and PNP transistor (BF550, SIEMENS).

The device can also couple with an external component, such as an external mouth piece to measure the lung volume. The mouth piece contains a diaphragm. Its deflection associated to a specific pressure. The amount of deflection of the membrane using the device defines the amount of volume of the air transferred during the period of expiration.

For healthy adults, the first sound (S1) and the second sound (S2) of the heart have acoustic frequencies of 10 to 180 Hz and 50 to 250 Hz, respectively. Vibration frequencies of vocal folds in humans range from 90 to 2000 Hz. With an average fundamental frequency of ~116 Hz (male, mean age, 19.5), ~217 Hz (female; mean age, 19.5), and ~226 Hz (child, age 9 to 11) during conversation. To enable sensing of cardiac operation and speech, the cutoff frequency of the low-pass filter is 500 Hz. The high-pass filter (cutoff frequency, 15 Hz) removes motion artifacts.

Low frequency respiration cycle (0.1-0.5 Hz), cardiac cycle (0.5-3 Hz), and snoring signal (3-500 Hz) have their own specific frequency band. By passing these specific frequency band for each of these biomarkers, the filter removes the high frequency noise and low frequency motion artifacts.

Aside from the present frequency range, from the raw data, it measures many other mechanical and acoustic bio signals (e.g. Scratching movement (1-10 Hz), Scratching sound (15-150 Hz)).

Figure 8:
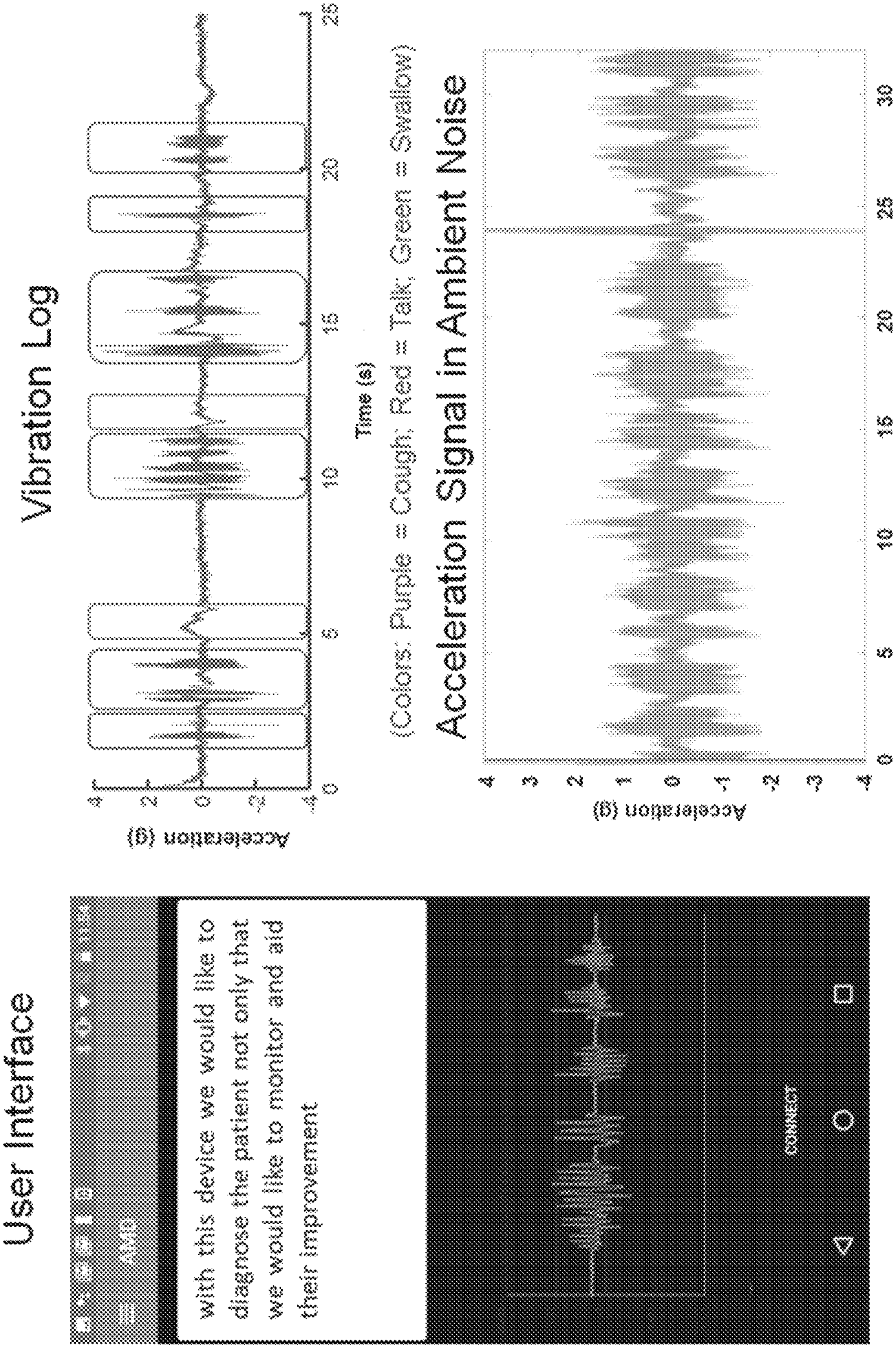
FIG. 8 provides data from epidermal mechano-acoustic-electrophysiological measurement of vocal folds (e.g., talking) and swallowing including vibration and acceleration and provides an example user interface for a processor providing a real-time metric.
Figure 9:
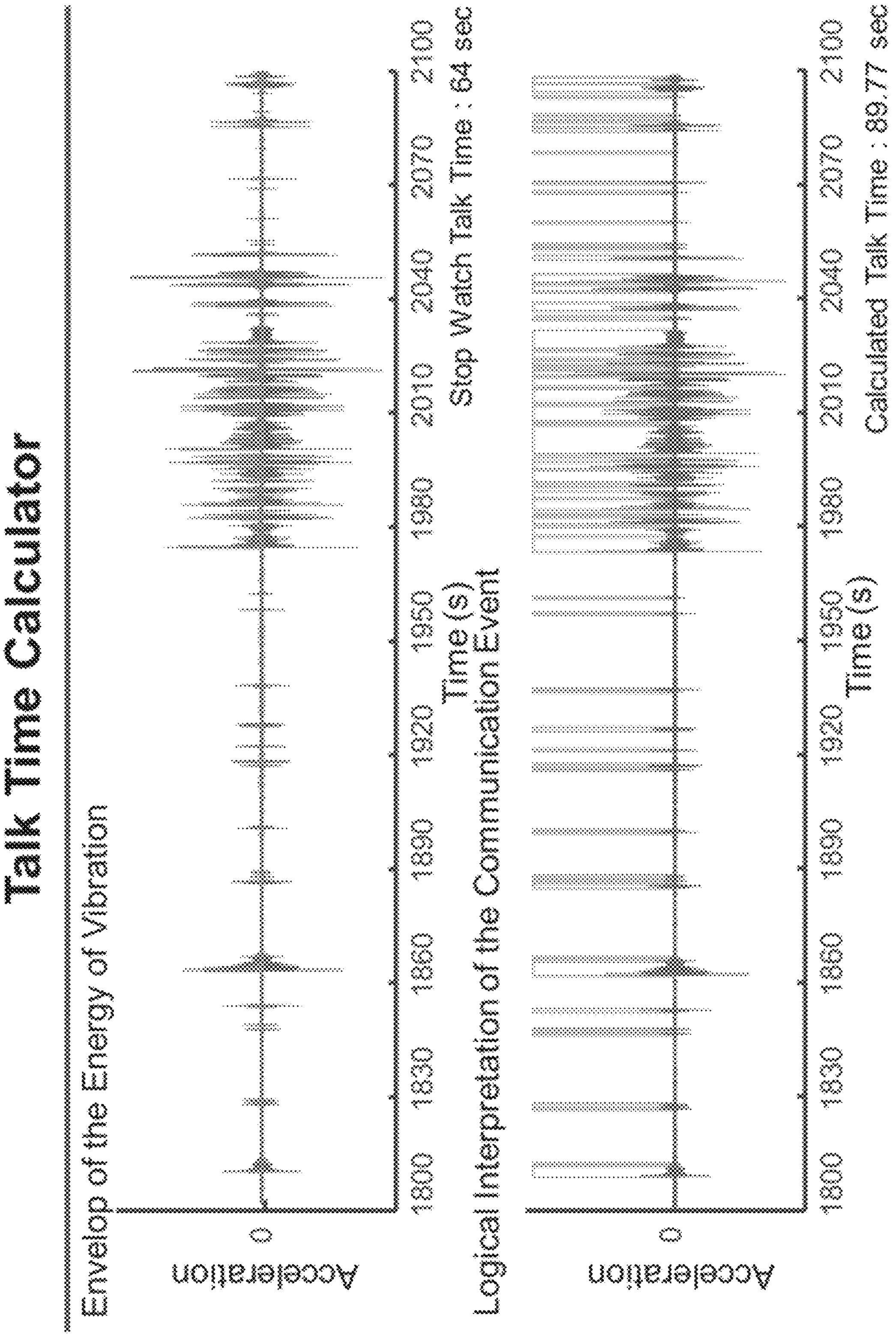
FIG. 9 provides data from epidermal mechano-acoustic-electrophysiological measurement of vocal folds measuring talking via acceleration.
Figure 10:
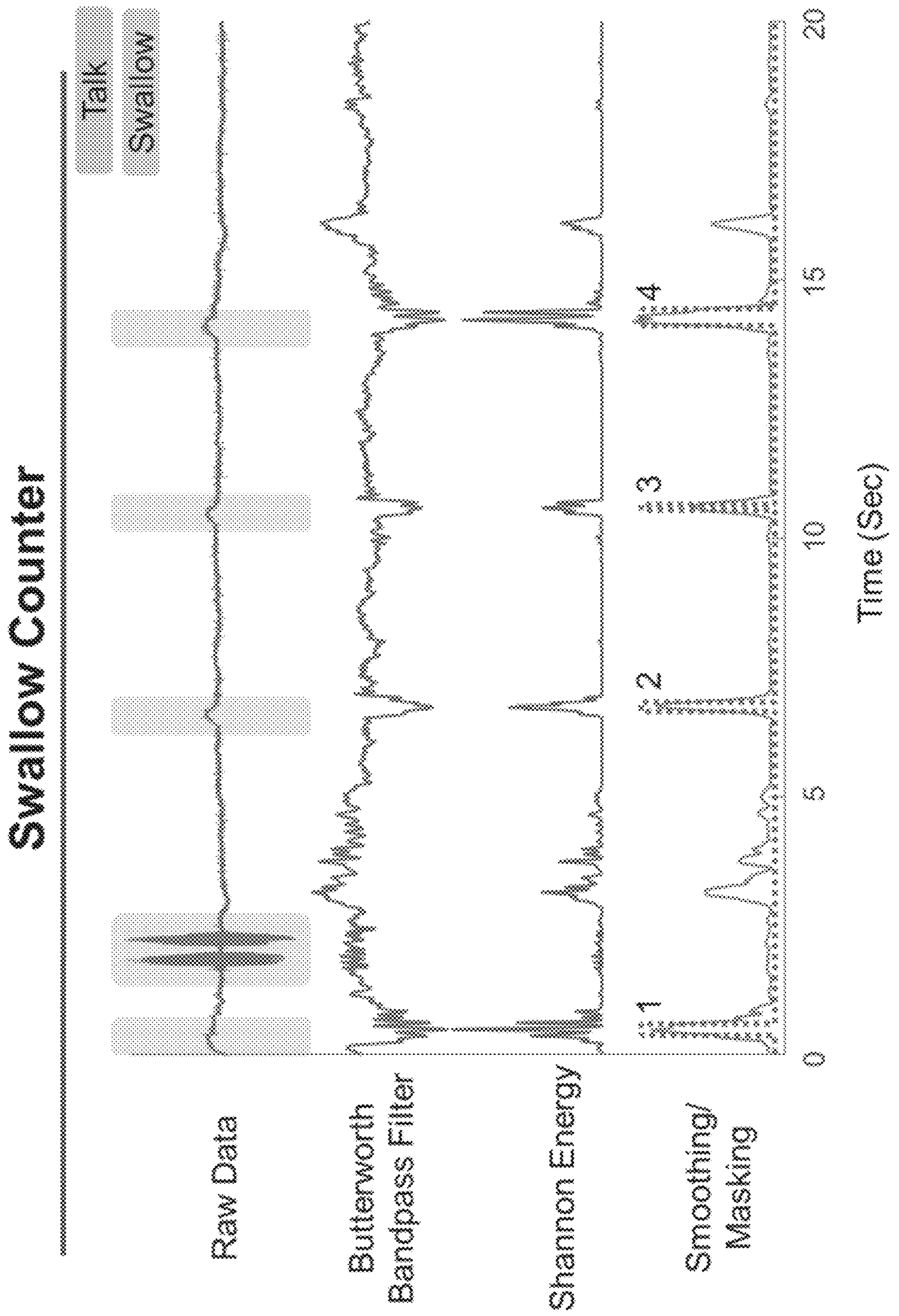
FIG. 10 provides data from epidermal mechano-acoustic-electrophysiological measurement of vocal folds including talking and swallowing.

FIGS. 8-10 illustrate examples of an epidermal mechano-acoustic-electrophysiological measurement of vocal folds (e.g., talking) and swallowing according to some processing algorithms of the present technology including filtering and automatic analysis of the signal.

Signal processing algorithms including but not limited to Shannon energy conversion, moving average smoothing, Savitsky-Golay smoothing, and automatic threshold set up faster analysis of the large volume of data.

The general signal processing involves seven parts: (i) collection of raw data; (ii) filtering of the data; (iii) normalization of the filtered data; (iv) energy conversion of the data; (v) smoothing of the data and production of the envelop; (vi) threshold setting; (vii) masking of the data.

The following describes the signal processing in more detail: (i) Capturing the raw acceleration signal without analog filter provides multiple signals superposed onto each other. (ii) Filtering of the data in various bands of frequency spectrum dissects the raw signal into multiple layer of signals specific to different biomarkers. (iii) Normalization of each filtered data allows reasonable comparisons of each signal. (iv) Converting the normalized filtered signal simplifies the signal to all positive values. Observing signals that are higher than DC frequency regime, the signal fluctuates across the zero-base line. For information related but not limited to the duration of talking, coughing, or swallowing, the true measurement is possible with energy interpretation of the signal. (v) smoothing the data contains the normalized filtered signal and represents the measured signal in simpler way. (vi) using histogram, or automatic threshold setting algorithm, certain activity can be determined and classified. (vii) Using the picked threshold value, mask defines the number of samples associated to the activity.

Wavelet transform method simply extracts out the signals related to certain activity, such as talking, laughing, coughing, or swallowing. Using the scale and time information from the transformation, it classifies specific characteristics of swallowing in specific type of food contents, and type of communication and interaction.

Supervised machine learning of labeled signal involves two parts: (i) labeling the activity to signal by time stamping the data at the time when the event occurs; (ii) multi-class classification methods including but not limited to the Random Forest method.

Such classification generates classification for specific incidents of breathing pattern (inspiration, expiration), swallowing specific type of food (fluid, solid), and human machine interface for vocal fold vibration recognition.

The following describes human interface in more detail. Learning the trend of respiration cycle and swallowing incident of normal, coin cell activates to cue the appropriate swallowing time based on the respiration cycle for people who has difficulty in swallowing. Also measuring the movement and frequency of the vocal folds and learning the letter and words associated to specific vibration.

Subjective study including social meter utilizes unsupervised learning. It includes dimension reduction methods such as Latent Dirichlet for obtaining predictors. Then, clustering methods including but not limited to k-modes and DBSCAN categorizes the specific group of people with share of similar behavior of the signal.

Reinforced learning correlates the clinical result of therapy given by the device's user interface. The implementation of reinforced learning happens towards to the end of classification and set of pilot studies.

FIG. 5 illustrates a sensing circuit diagram of an example of an epidermal mechano-acoustic-electrophysiological measurement/therapeutic device according to some embodiments of the present technology.

Figure 19:
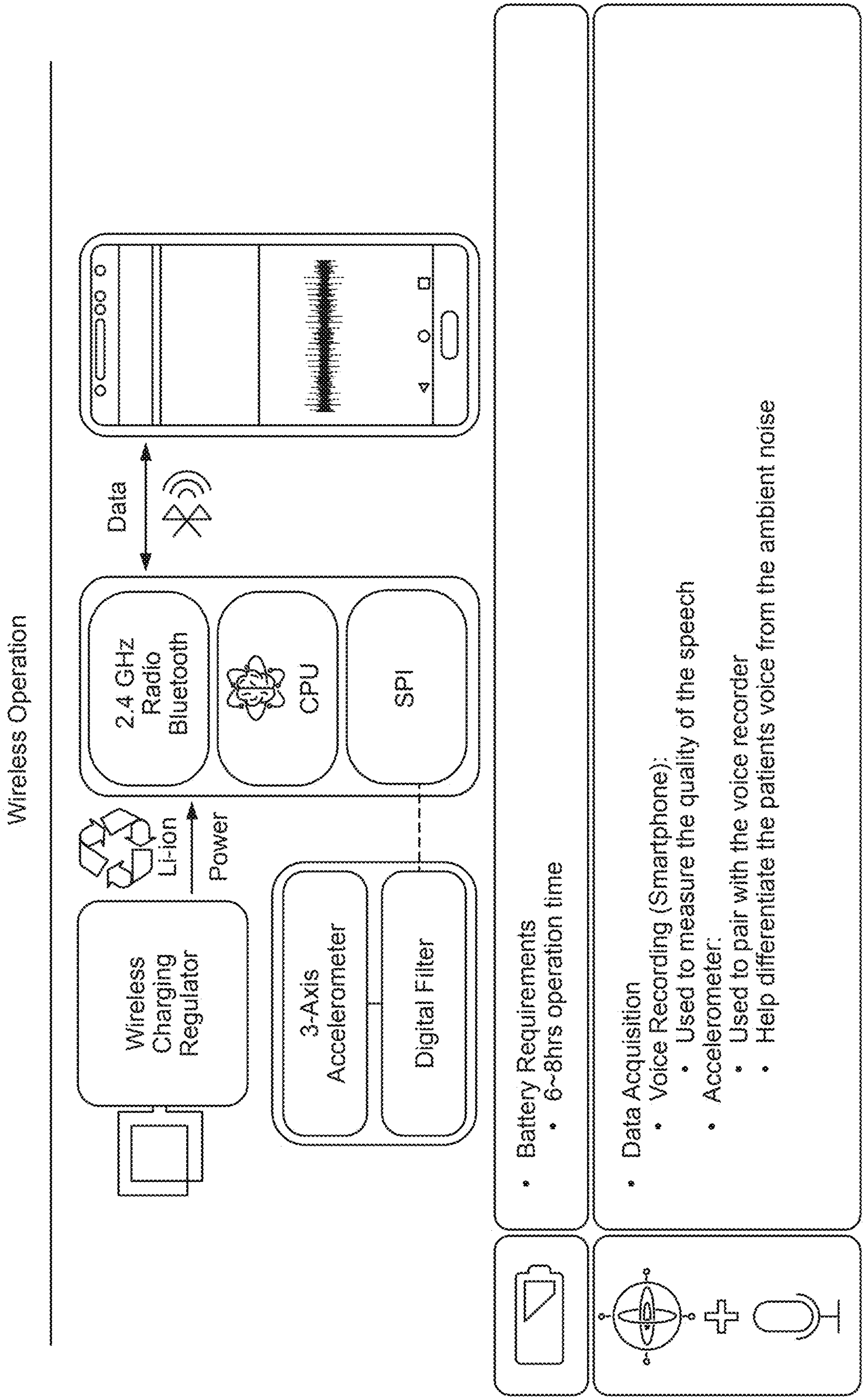
FIG. 19 illustrates wireless connection between an epidermal mechano-acoustic-electrophysiological measurement/therapeutic device and a processor (e.g. smartphone, tablet, laptop, etc.).
Figure 20:
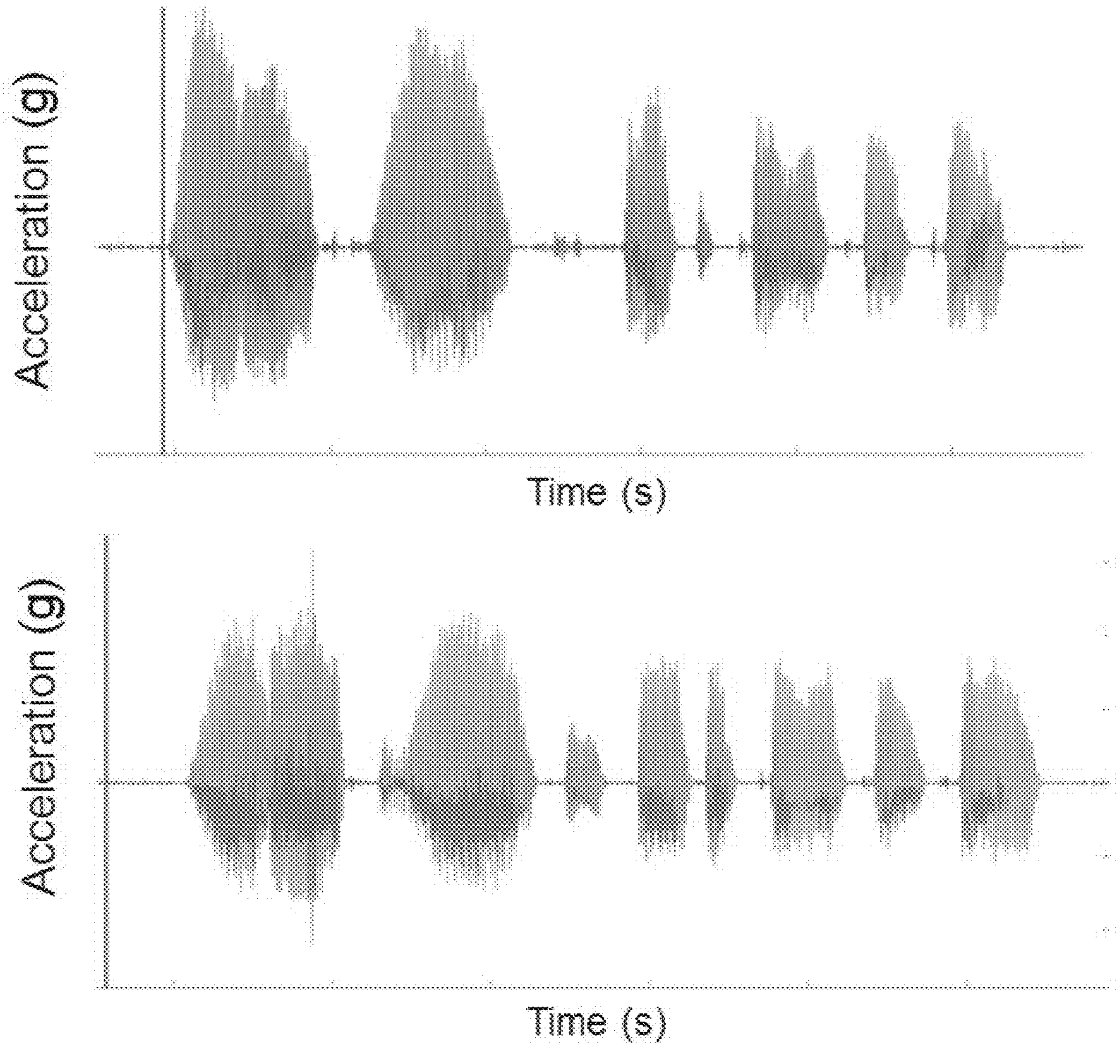
FIG. 20 illustrates that the devices described herein are insensitive to the ambient environment.

The system may employ any of a range of bidirectional communication systems, including those that correspond to the Bluetooth® standard, to connect to any standard smartphone (FIG. 19), tablet or laptop. It is a secure, both consumer-end and researcher-focused user interface. The data measurement meets HIPAA compliant data transfer and cloud storage—we have previously used Box® as a HIPAA compliant storage platform for our wireless sensors. Further signal analysis work would enable classification of other relevant behaviors for individuals with AD such as personal hygiene (brushing teeth), chores, or driving. This signal processing and further machine learning based on the output of the sensor can be deployed either on the device itself, a smartphone, or a cloud-based system.

On board memory provides maximum freedom in the wireless environment even without the user interface machines that are linked to the device for data streaming and storage.

Figure 7:
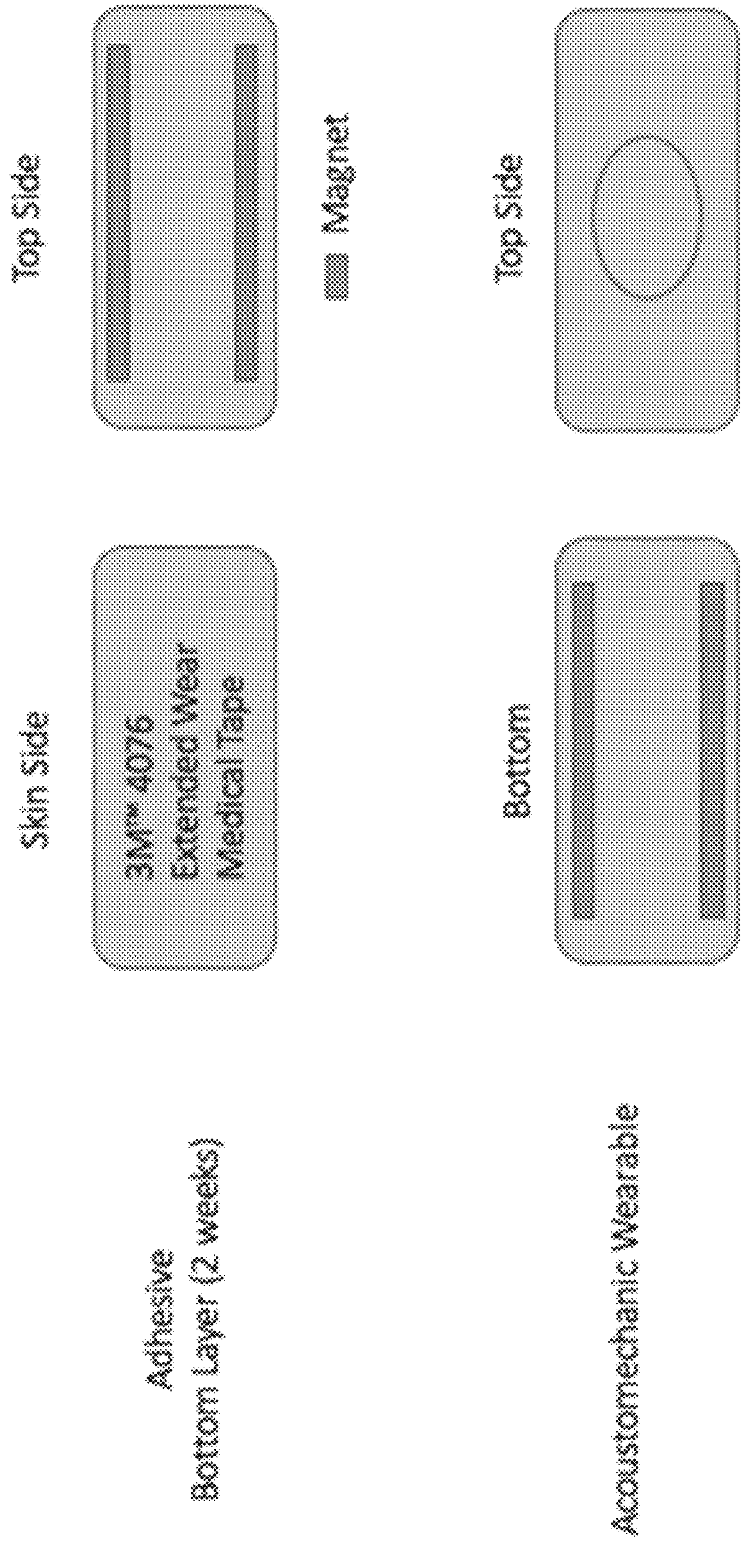
FIG. 7 provides examples of adhesive configurations useful for establishing contact of an epidermal mechano-acoustic-electrophysiological measurement/therapeutic device with a surface (e.g. tissue, skin).

Beyond the use of traditional adhesives—we propose a novel skin-device interface that incorporates adhesives that last up to 2 weeks of continuous wear. Rather than requiring the user to adhere and remove the sensor completely from the skin, particularly the fragile skin of the neck, our device can detach and reattach with the use of magnets. Other coupling mechanisms can involve buttons, clasps, hook and loop connections. The adhesive attached to the skin can be varied by type (e.g. acrylic, hydrogel, etc) and optimized to the desired length of skin adherence (FIG. 7).

Wireless Functionality:

Communications to the user interface machine that displays, stores, and analyzes the data are generally known. Here, in contrast, we present the sensor technology that has onboard processor, data storage, and also communicates to the user interface via a wireless protocol, such as BLUETOOTH®, or in some embodiments ultra-wide band or narrow band communication protocols, optionally capable of providing for secure transmission. This way, one can utilize the device in a naturalistic setting without requirement for an external power source.

The device is powered by inductive coupling and also can communicates and/or transfer data via near field communication (NFC) protocol. When the user is utilizing the device within a confined environment, such as a bed during sleep, or in a hospital setting, the power and data transmission can be done via inductive coil that resonates at 13.56 MHz. This allows continuous measurement without the need for an onboard battery or external power source.

Wireless battery charging platform enables a completely encapsulated device that separates the electronics from the surroundings, preventing substances that would otherwise damage the sensor. The encapsulation layer is made out of thin membrane of a polymer or elastomer, such as a silicone elastomer (Silbione RTV 4420). Such an encapsulation layer is even less permeable than the polydimethylsiloxane and ecoflex described in the prior art.

Advanced Signal Processing

Digital filtering: both type of (finite impulse response) FIR and infinite impulse response (IIR) digital filters are used appropriately. With the specific time window automatically selected in the region that has high signal to noise ratio, specific frequency band is selected to reduce the effect of artifacts and noise and maximize signal of interest Algorithms for signal-specific analysis: one method involves the processing of filtered signal in the time domain. When the signal of interested is filtered with the appropriate band of frequency, the specific event of interest (e.g. talking vs coughing vs scratching) is better elucidated from the acoustomechanic sensor's raw output. Using energy information generated from acceleration of the sensor, the information such as the duration of a discrete event or the number or the frequency of the event is better calculated. Another processing technique our system uses power frequency spectrum analysis where the power distribution of each frequency component is assessed. This allows the derivation of additional information from the raw signal (e.g. pitch from audio).

Machine Learning

Supervised Learning: supervised machine learning of labeled signal involves two parts: (i) labeling the activity to signal by time stamping the data at the time when the event occurs; (ii) multi-class classification methods including but not limited to the Random Forest method. Such classification generates classification for specific incidents of breathing pattern (inspiration, expiration), swallowing specific type of food (fluid, solid), and human machine interface for vocal fold vibration recognition.

Using the scale and time information from the transformation, as an example, we can classify the specific characteristics of swallowing that relate to the food content eaten (e.g. thin liquid like water, thick liquid, soft foods, or regular foods) through supervised machine learning. This process does not require the time or frequency ambiguity as much as the fast Fourier transform.

The following describes human interface in more detail. Learning the trend of respiration cycle and swallowing incident of normal, coin cell activates to cue the appropriate swallowing time based on the respiration cycle for people who have lost the ability to time swallowing with breathing. Also, the sensor measures the movement and frequency of the vocal folds and learning the letter and words associated to each specific signal.

Unsupervised Learning: this is accomplished without labeled signal inputs. In the case of a wearable social interaction meter, we employ unsupervised learning. It includes dimension reduction methods such as Latent Dirichlet for obtaining features relevant to quantifying social interaction. This includes features of voice (tone, pitch), physical activity, sleep quality, and talk time. Then, clustering methods (e.g. k-modes and DBSCAN) categorizes a specific group of signals into categories.

Reinforced Learning: this involves the sensor system learning of the effect of haptic stimulation on swallowing and then measuring the actual swallowing event along with respiration. This enables the system to auto-adjust and calibrate to ensure that the measured swallowing event corresponds to the ideal timing within the respiratory cycle.

Personalized "Physical" Biomarkers

The coupling of high-fidelity sensing, signal processing, and machine learning enable the creation of novel metrics that can serve as physical biomarkers of health and well-being. For instance, the ability to quantify spontaneous swallowing during the day has been shown previously to be an independent measure of swallowing dysfunction. Thus, the sensors provided herein can be used to calculate, in a patient's naturalistic environment, scores of swallowing function that are sensitive to small but clinically meaningful changes.

The timing of swallowing in relationship to the respiration cycle (inspiration, expiration) is important to avoid problems such as aspiration, which can lead to choking, or pneumonia. The ability to time swallowing is largely under involuntary control leading to a coordinated effort between respiration and swallowing. However in conditions such as stroke or head/neck cancer where radiation is delivered, this coordination is lost. Our sensor could then quantify swallowing events in the context of the respiratory cycle and provide a measure of "safe swallows." Social interaction scores can also be created via signal process and machine learning to create aggregate scores of social activity. This can be used as a threshold to engage caregivers, or loved ones to increase daily social interaction when a baseline threshold is not met. These are illustrative examples of how novel metrics can be derived from this sensor system to enable patient behavior change, or clinician intervention and caregiver intervention.

Therapeutic Wearable Sensors

In this present disclosure, there are advanced functionalities presented for the sensor system that serve a therapeutic purpose. Prior work has focused solely on diagnostic uses.

Examples of two therapeutic uses are described herein. First, the timing of safe swallowing enables prevention of dangerous events such as aspiration, which can lead to choking, pneumonia, or even death. Our sensor can be converted into a therapeutic swallow primer that triggers user swallowing based on sensing the onset of inspiration and expiration of the respiratory cycle. This enables the sensor to trigger swallowing during a safer part of the respiratory cycle (typically mid to late end expiration). Further, machine learning algorithms can be used to optimize the timing of the trigger in a feedback loop. For instance, the sensor can track both respiratory rate and swallowing behavior. A trigger is delivered that is timed to lead to a swallow event within an ideal respiratory timing window. In this embodiment to trigger a swallow, we propose a vibratory motor that provides direct haptic feedback. Other trigger mechanisms may include a visual notification (e.g. light emitting diode), an electrical impulse (e.g., electrodes), a temperature notification (e.g., thermistors). In some embodiments, for example, the system is configured to provide a sensor that detects one or more parameters which are used as the basis of input for a feedback loop involving a signaling device component that provides one or more signals to a subject (e.g., patient), such as a vibrational signal (e.g. electromechanical motor), and electrical signal, a thermal signal (e.g. heater), a visual signal (either LED or a full graphical user interface), an audio signal (e.g., audible sounds) and/or a chemical signal (elution of a skin-perceptible compound such as menthol or capsaicin). In such embodiments, the feedback loop is carried out for a specified time interval on the basis of measurements by the sensor, wherein one or more signals are provided to the subject periodically or repeatedly on the basis of the sensed parameter(s). The feedback approach may be implemented using machine learning, for example, to provide an individualize response based on measured parameters specific to a given subject.

In an embodiment, on-body sensing is achieved with an enclosed sensing/stimulating circuit enabled through real-time processing, wherein the feedback loop can be haptic, electrotactile, thermal, visual, audio, chemical, etc. In an embodiment, the sensors would also be able to work in a network—and that anatomically separate sensing allows for more information—one sensor could measure (e.g. on the suprasternal notch) but trigger feedback in a sensor somewhere else that is more hidden (e.g. chest).

Figure 11:
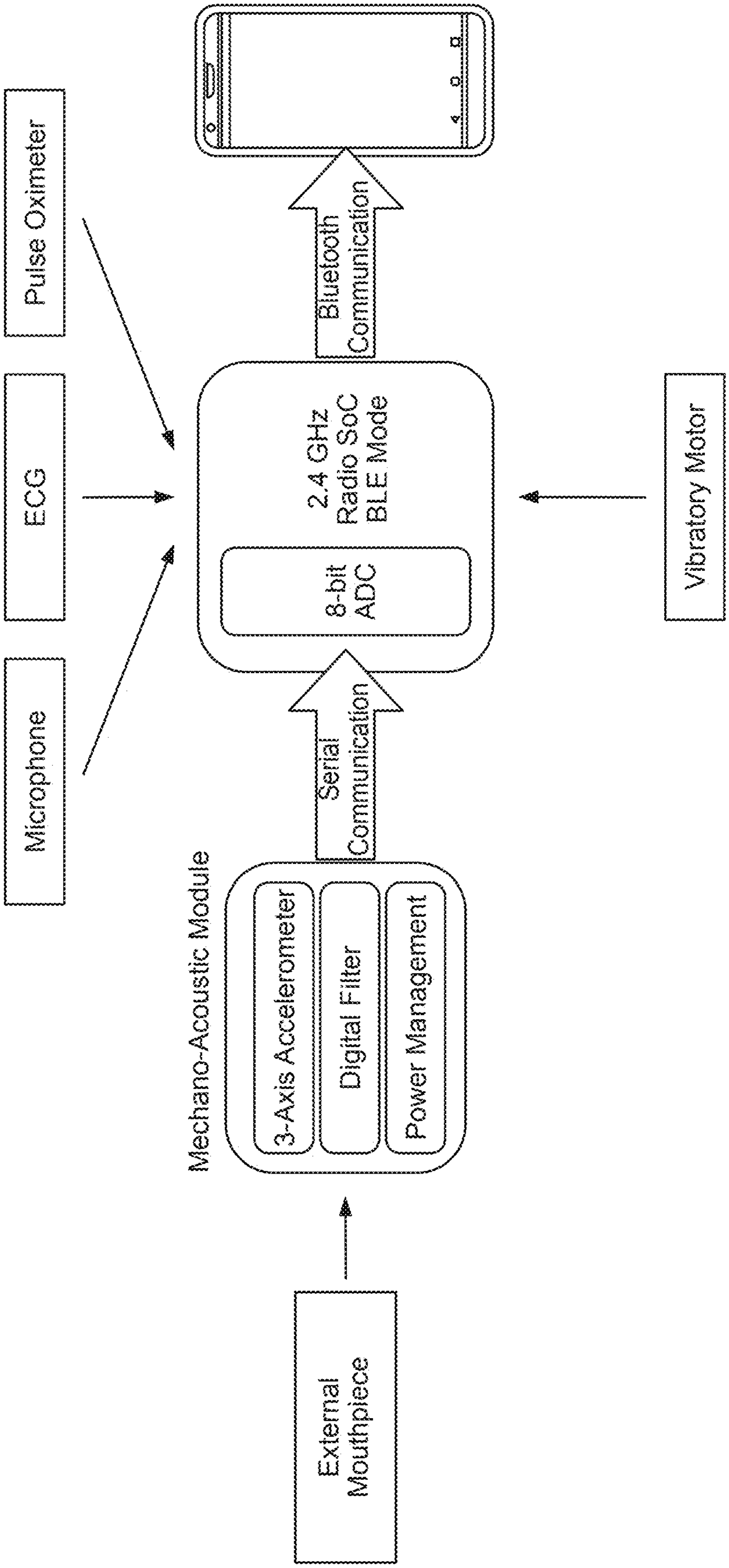
FIG. 11 provides a flowchart for an epidermal mechano-acoustic-electrophysiological including an external mouthpiece operating as a wireless spirometer in Bluetooth communication with an external device.
Figure 12:
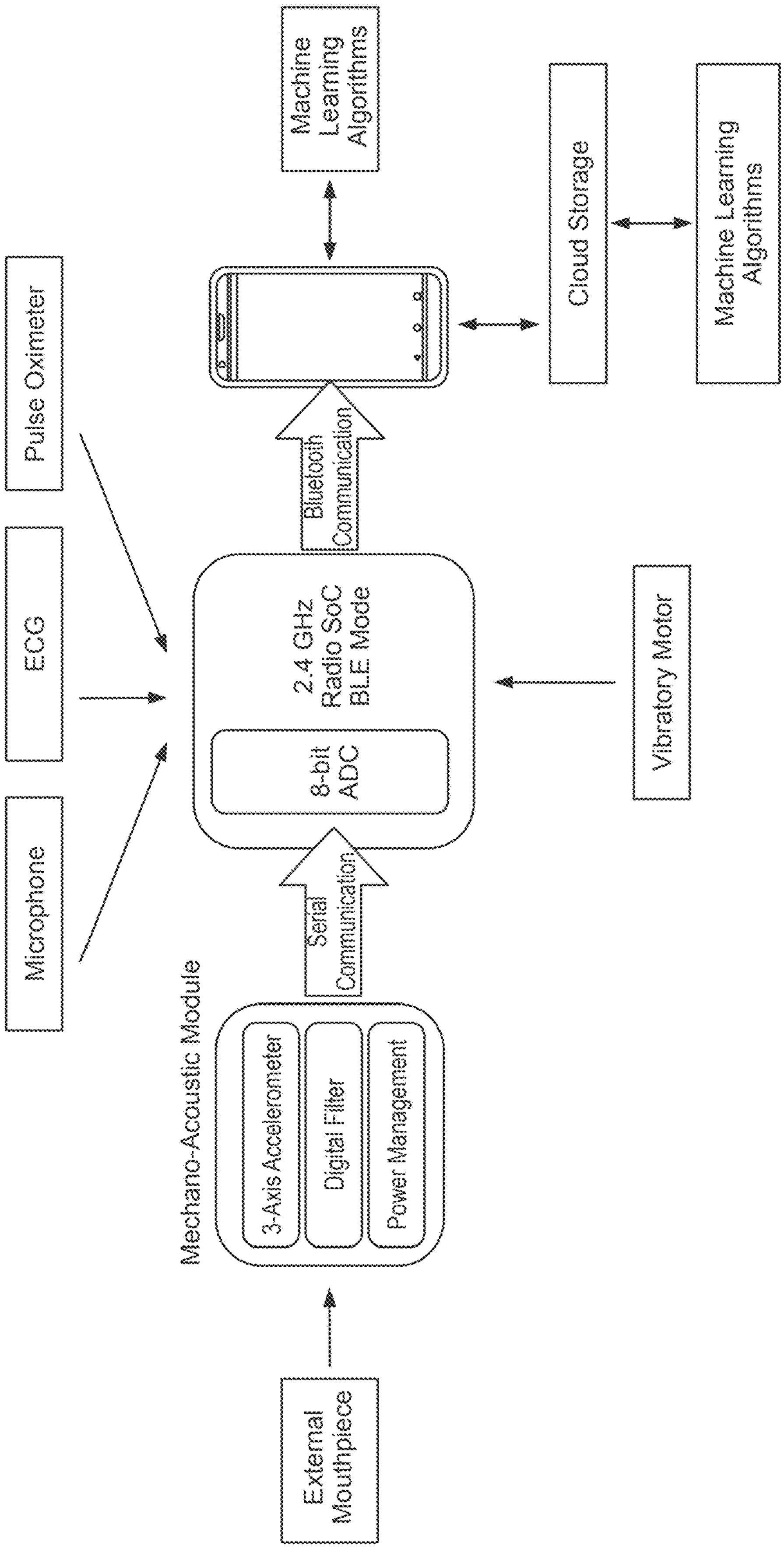
FIG. 12 provides a flowchart for an epidermal mechano-acoustic-electrophysiological including an external mouthpiece illustrating connectivity to cloud storage and machine learning algorithms.
Figure 13:
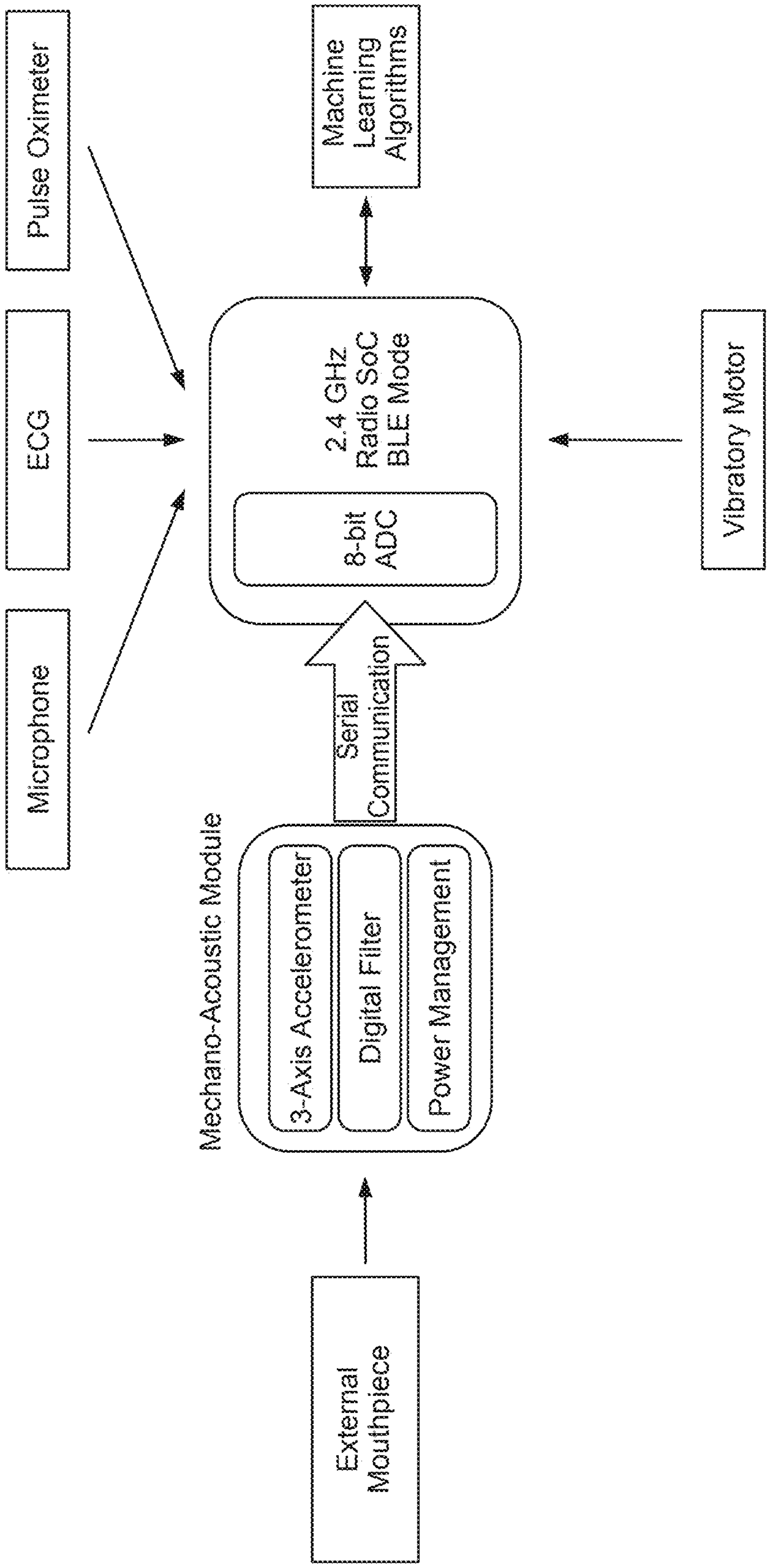
FIG. 13 provides a flowchart for an epidermal mechano-acoustic-electrophysiological including an external mouthpiece utilizing machine learning algorithms.
Figure 14:
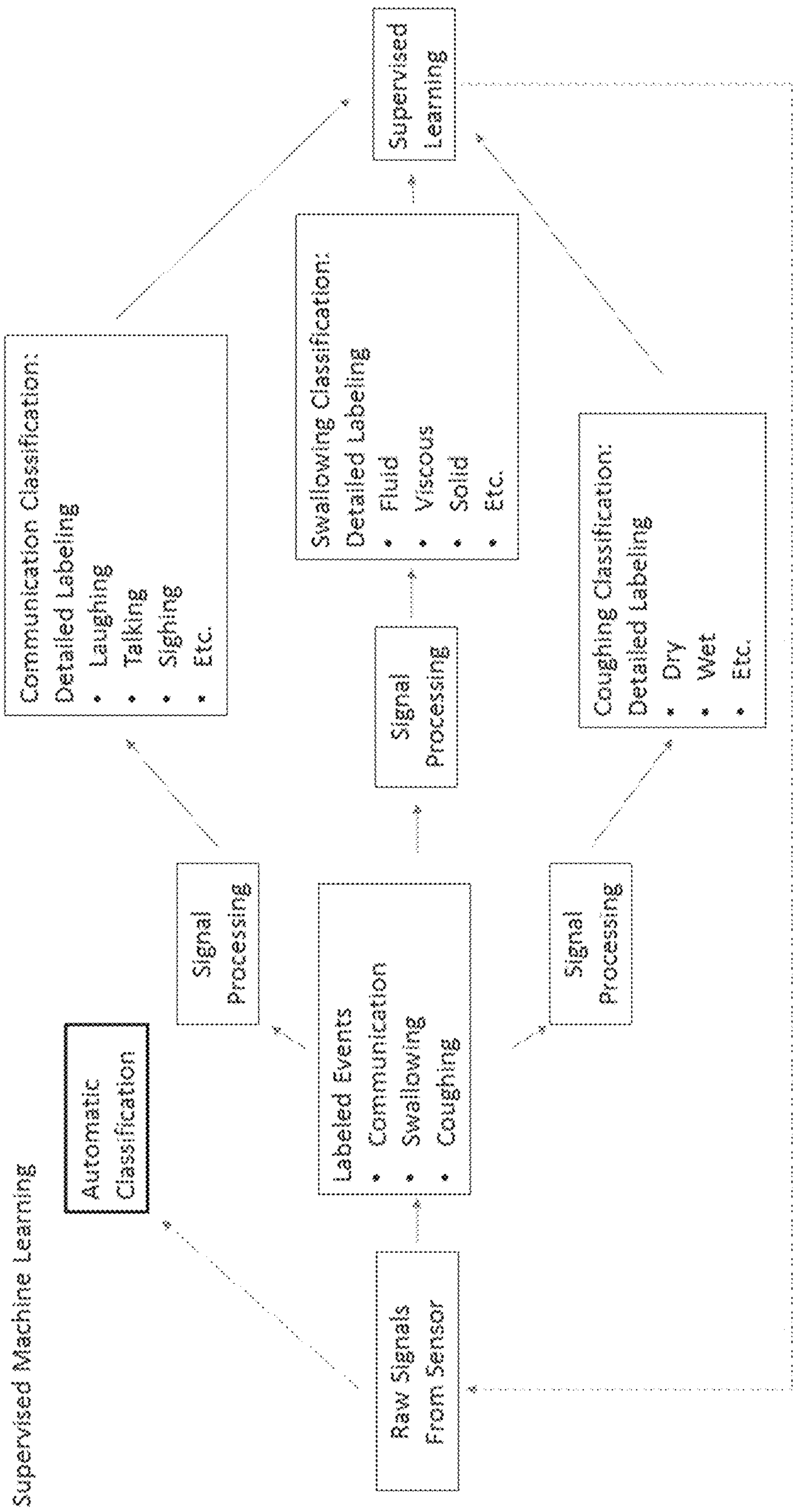
FIG. 14 provides an example flowchart for supervised machine learning and signal processing that may be used with the various devices described herein.
Figure 15:
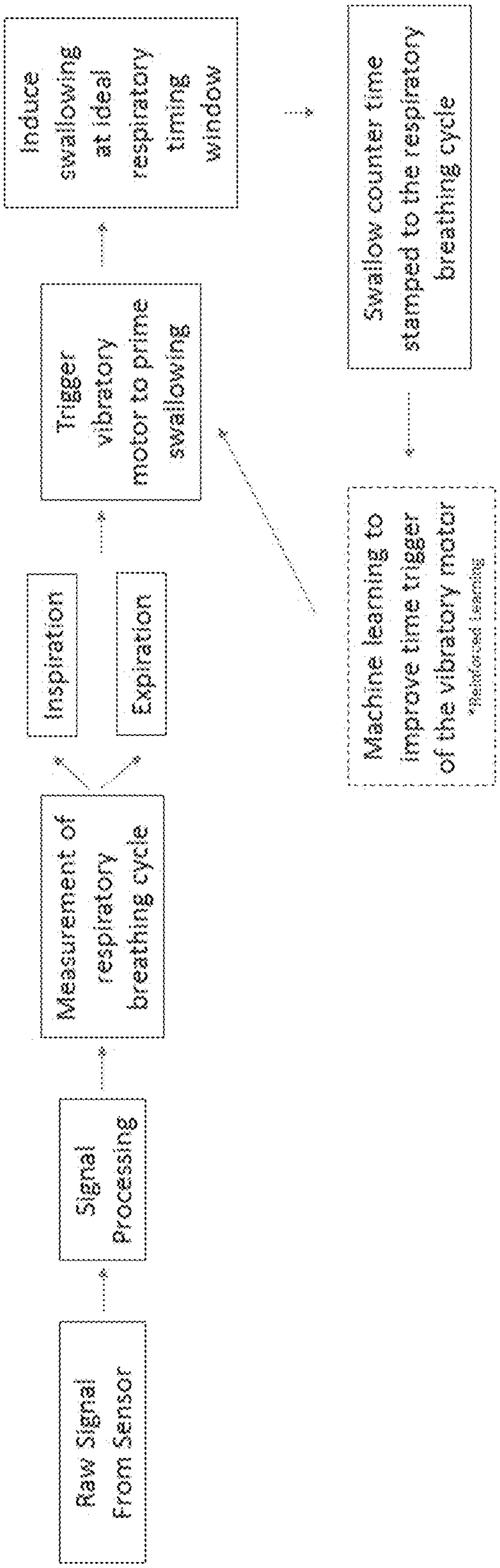
FIG. 15 provides an example flowchart of a treatment of a user (e.g. patient) and analysis that may be used with the various devices described herein.
Figure 16:
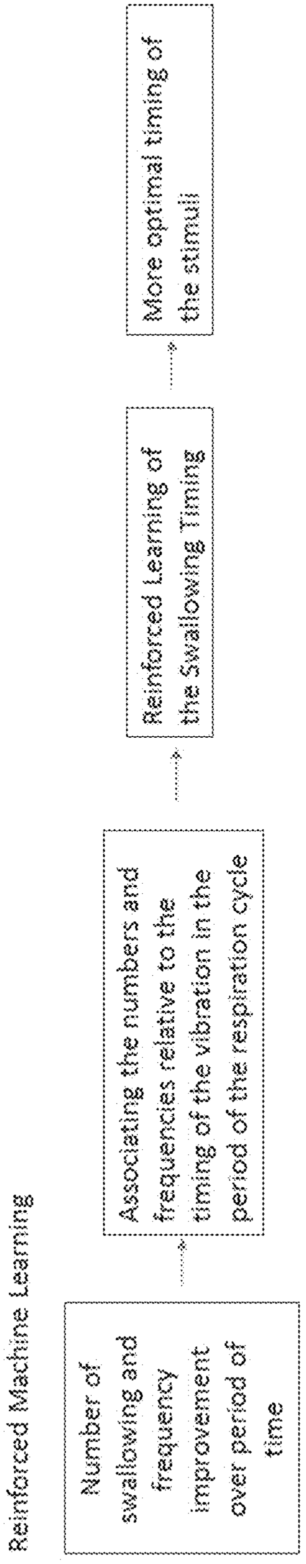
FIG. 16 provides an example flowchart for reinforced machine learning and signal processing that may be used with the various devices described herein.
Figure 17:
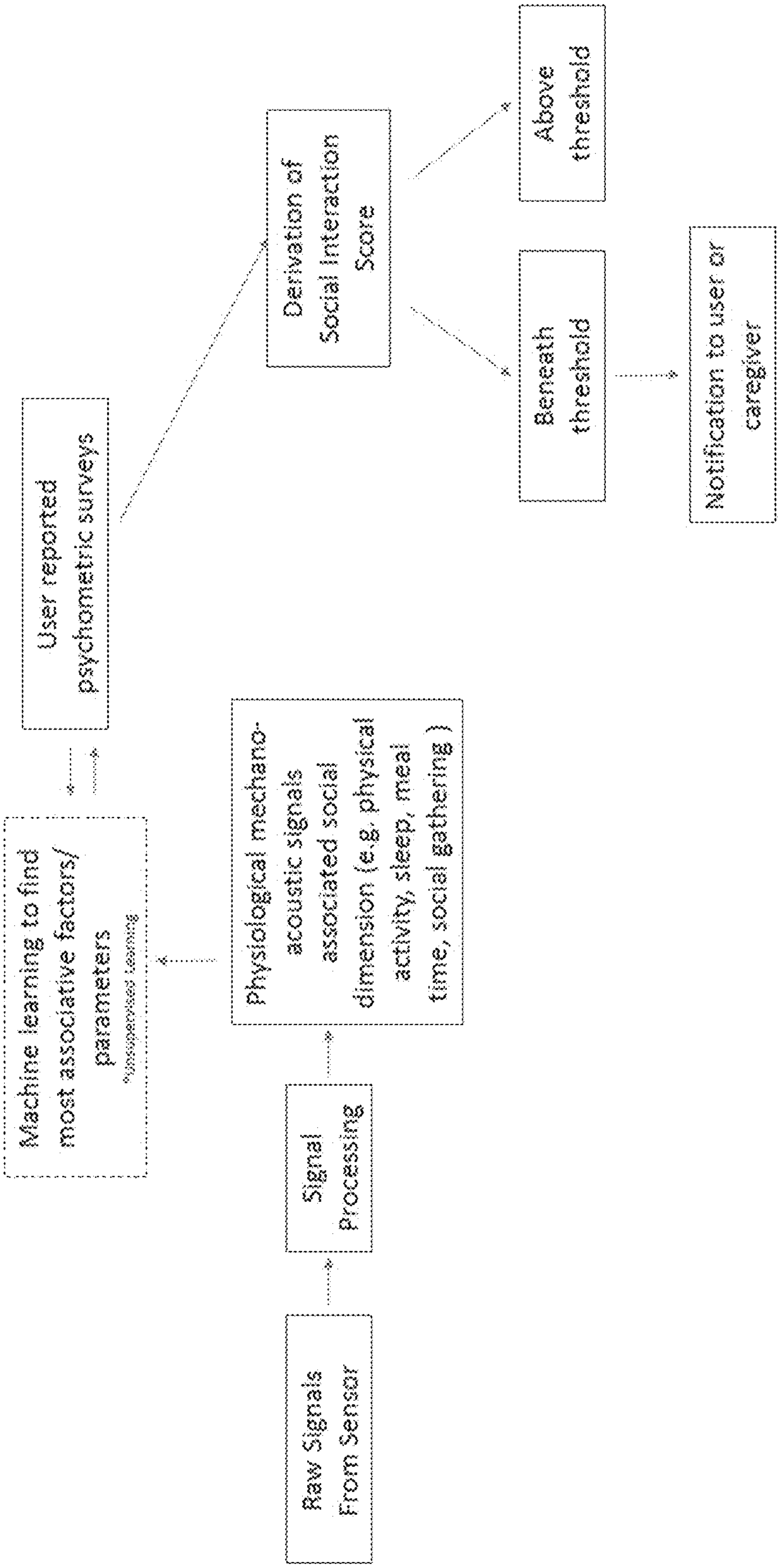
FIG. 17 provides an example flowchart for supervised machine learning and signal processing that may be used with the various devices described herein, including the use of thresholding with relation to a social interaction score.
Figure 18:
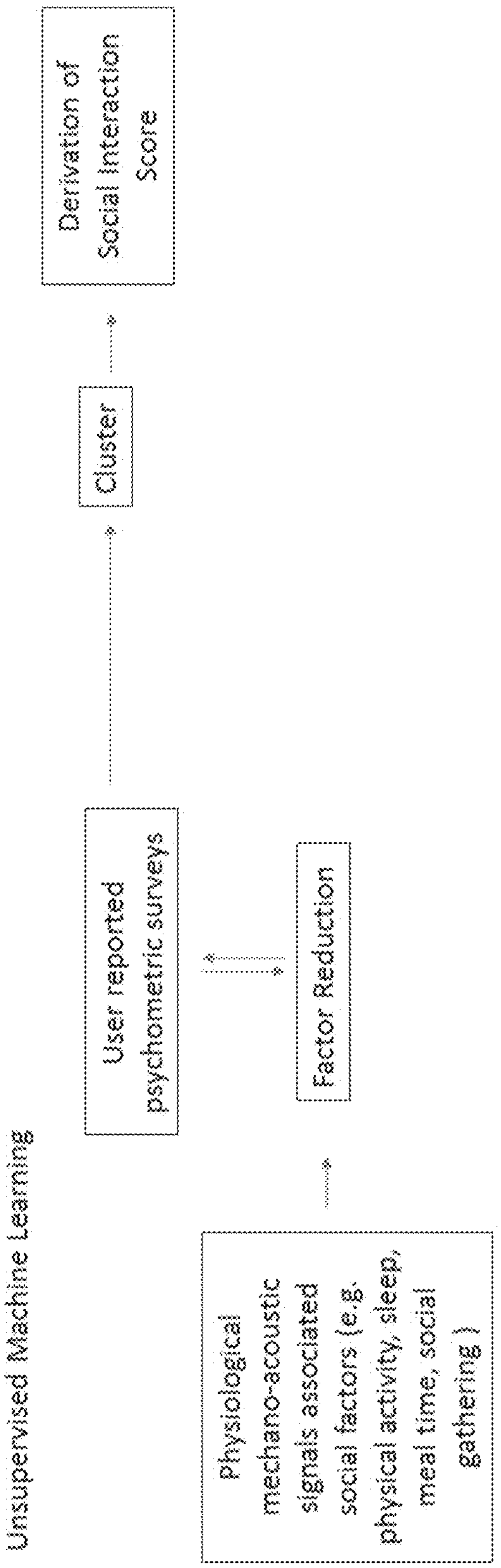
FIG. 18 provides an example flowchart for unsupervised machine learning and signal processing that may be used with the various devices described herein.

A second therapeutic modality is for the sensor to act as a wearable respiratory therapy system. In conditions such as chronic obstructive pulmonary disorder (COPD), dyspnea or shortness of breath is a common symptom that greatly impacts quality of life. Respiratory therapy is a commonly deployed method that trains a subject to control their breathing (both timing and respiratory effort) to increase lung aeration and improve respiratory muscle recruitment. Our sensor can be used to track respiratory inspiration and expiration efforts and duration. Based on these measurements, haptic feedback (or visual feedback via an LED) can potentially train users to extend or shorten inspiration or expiration to maximize airflow. Respiratory inhalation effort can also be triggered as well. For instance, if a certain respiratory inspiratory effort is achieved a threshold is passed triggering a haptic vibration. This haptic feedback can also be triggered after a certain length of time is reached for an inspiratory effort. Thus, the sensor can track airflow through the throat and use this as a way to deliver on-body respiratory training. In another embodiment, the sensor itself can be outfitted with an external mouthpiece (FIGS. 11-13) and operate as a wireless spirometer during training sessions and then be placed back on the throat for regular sensing.

Another therapeutic modality involves use of the present sensor systems to assess and, optionally treat a patient regarding, positioning of the body of a subject, or portion thereof, to prevent injury and/or support a given therapeutic outcome. Body injury can occur with motion and movement of limbs to points of significant deformation. This can occur for instances, for example, where a limb (e.g. shoulder) is injured and must be placed in a relatively immobile or limited in a safe range of motion, for example, to support healing or therapy. In instances of sleep or daily activity, the subject may inadvertently position this limb into a deformation that would cause injury. In these embodiments, the present sensors here are used as a sentinel system to assess the position in space of the limb—and lead to a notification (either haptic, sound, visual, thermal, chemical, electrical, etc.) to alert the user and/or a caregiver.

Medical Use Cases

Sleep Medicine: wireless sleep tracker with ability to measure: time until sleep, wake time after sleep onset, sleep duration, respiration rate, heart rate, pulse oximetry, inspiration time, expiration time, snoring time, respiratory effort, and body movement. Intimate skin coupling on the suprasternal notch enables capture of respiration and heart rate given the proximity to the carotid arteries and trachea. As an example, sleep medicine applications can extend beyond simply measuring vital signs sleep or provide sleep quality metrics. The present sensor systems also support applications to improve sleep. Example of applications for this aspect include the following:

1. In sleep, the sensor can detect a subject having altered vital signs (aberrant vital signs) that may include a combination of elevated or depressed heart rate, cessation of respiratory rate, decrease in pulse oximetry, or snoring (aberrant respiratory sounds). This then triggers a feedback mechanism such as a vibration, audio, visual, electrical, or thermal that causes the individual to shift position or become aware/awake.
2. In instances of injury or post-surgical situations, excessive movement or range of motion can lead to exacerbation of an injury—particularly in periods of unconsciousness such as sleep. An acoustomechanic sensor alone or within a network of multiple spatially separated sensors can detect a limb in space and trigger a feedback mechanism (e.g. vibration, audio, visual, etc) that notifies the user to return to safe position or avoid exacerbation of an injury.
3. In instances where difficult to quantify symptoms (e.g. pain and itch)—sleep quality is a surrogate marker of the severity of these symptoms. The sensor can thus be used to indirectly assess symptoms (e.g. pain or discomfort) by measuring sleep quality.

Figure 41:
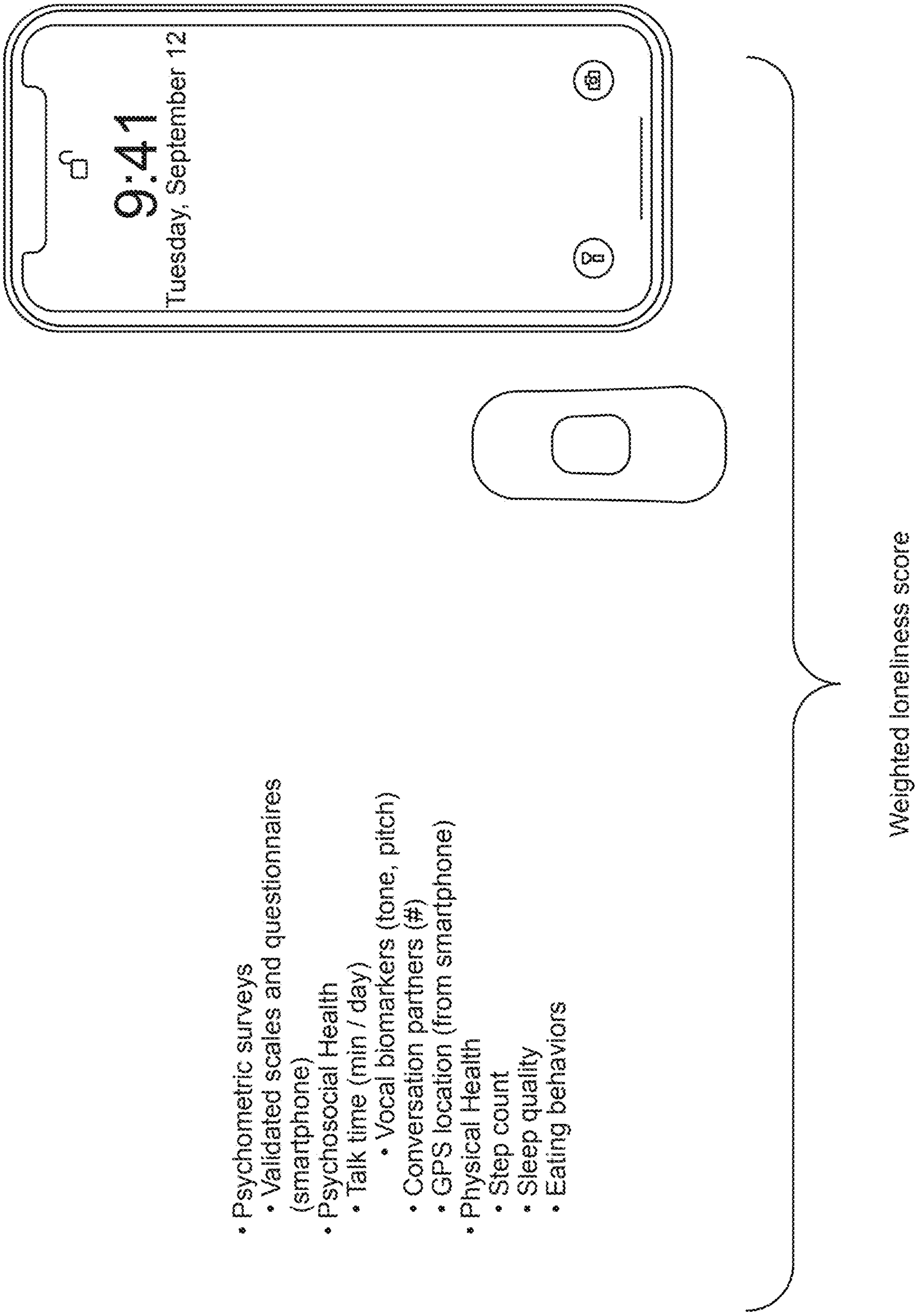
FIG. 41 provides an example of a sensing system comprising a sensor in communication with a portable electronic device for creating social interaction scores and metrics, including those based on psychometric surveys, based on validated scales and questionnaires and physical heath parameters derived, at least in part, from sensor signals and/or measured characteristics.

Another novel feature of this aspect of the invention is recapitulating sleep position and/or motion using the sensor across time. This allows using the accelerometer on the sensor to reconstruct movement and body position. This may allow for direct video feedback to the user and the ability to tie body position with vital signs or respiratory sounds (e.g. snoring) visually. FIG. 41 provides example sensor data for use of multimodal sensors of the inventor for sleep therapy, for example, for determination of body position and correlation of body position with vital signs and/or respiratory sounds.

In an embodiment, the sensors can evaluate position in space for specific limbs or body locations that are prone to injury (e.g. post-surgical rotator cuff) where if a dangerous range of motion or position is sensed this triggers a biofeedback signal that warns the user or causes the user to alter their position to avoid sleeping on an injured arm. The present sensor systems are also useful for monitoring an therapy in connection with snoring, for example, wherein sensing of snoring leads to vibratory biofeedback to trigger positional change.

In an embodiment, the sensors are used to recapitulate a video and/or visual representations of a subject's position in space. Benefits of this aspect of the invention included that it mitigates privacy concerns, data storage also.

Dermatology: ability to capture scratching behavior and distinguish this from other limb movements through coupling mechanical and acoustic signal processing.

Pulmonary Medicine: chronic obstructive pulmonary disease (COPD) is a chronic condition characterized by relapsing pulmonary symptoms. Our sensor would be able to quantify important markers indicative of COPD exacerbation including: cough, throat clearing, wheezing, altered air volume with forced lung expiration, respiratory rate, heart rate, and pulse oximetry. Asthma and idiopathic pulmonary fibrosis can similarly be assessed with the same measures.

Social Interaction Metrics, Quantification of Acoustic and Linguistic features of single speaker and multiple speaker tasks: measurement of spoken discourse and speech signals as components of social interaction is complex, requiring a sensor capable of capturing a wide range of acoustic and linguistic parameters, as well as acoustic features of the speaking environment. The sensor can quantify key parameters of social interaction related to the inbound acoustic signal including talking time and number of words. The recorded signal can be used to extract additional data including phonatory features (e.g., F0, spectral peak, voice onset time, temporal features of speech) as well as linguistic discourse markers (e.g. pausing, verbal disfluencies). When worn by individual interlocutors, the sensor is able to capture linguistic features across multiple interlocutors from the separately recorded signals, facilitating analysis of conversation social interactions. The coupling to skin along the suprasternal notch enables precise quantification of true user talk time regardless of ambient condition. Furthermore, social interaction is a complex multi-factorial complex. The present disclosure enables quantification of important physical parameters (e.g. sleep quality, eating behavior, physical activity) that can potentially be combined into a novel metric for social interaction.

Figure 40:
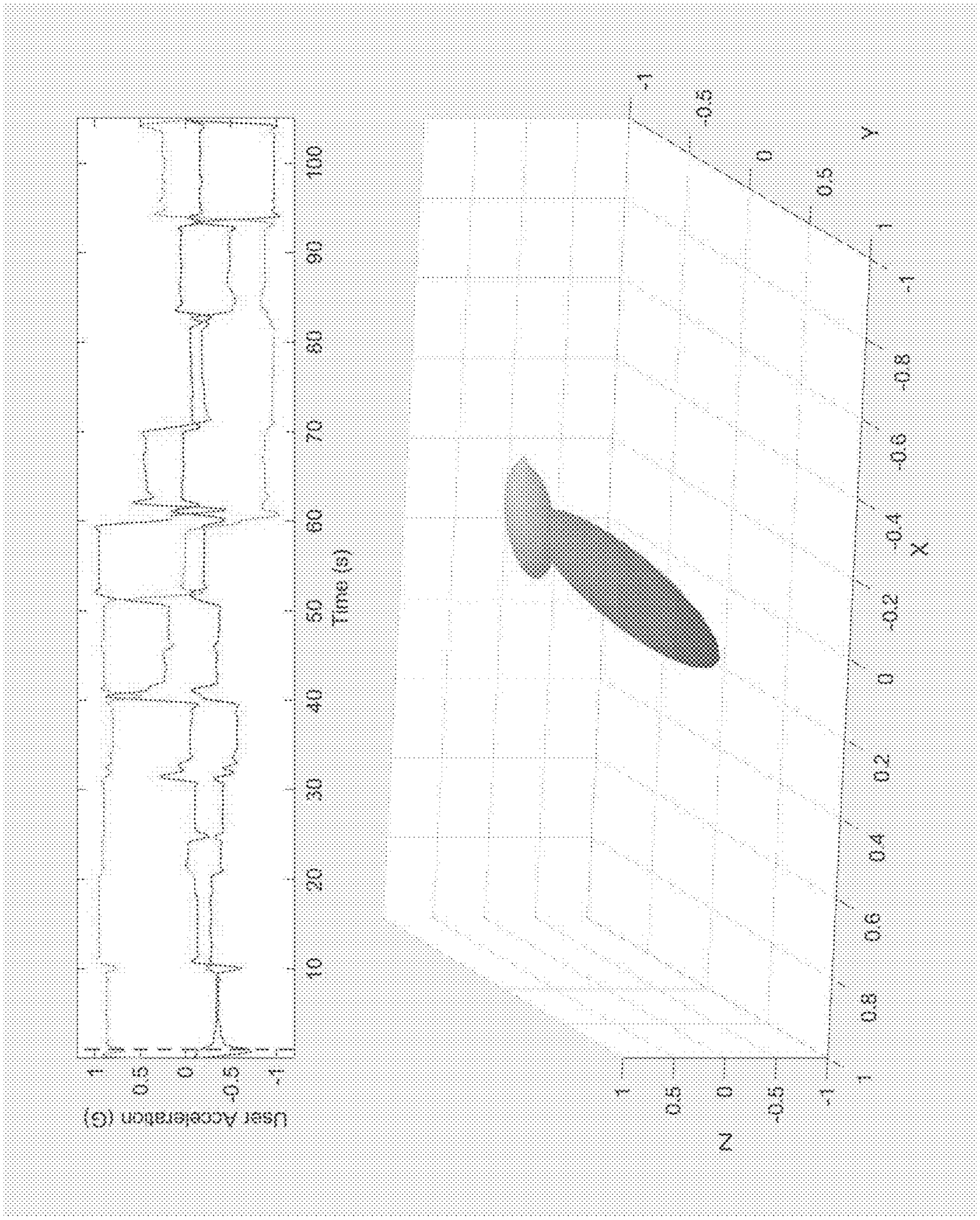
FIG. 40 provide results for a study of wearable sensors for children (24 months or younger) with cerebral palsy compared to age matched controls: development of a new early detection tool.

The present sensor systems are also useful for creating and monitoring social interaction scores and metrics, for example, using approaches based on sensor signals, feedback analysis and/or signaling to a subject. FIG. 40 provides an example of a sensing system comprising a sensor in communication with a portable electronic device (e.g., smart phone) for creating social interaction scores and metrics, including those based on psychometric surveys, based on validated scales and questionnaires (using smartphone, in combination with psychosocial health parameters (e.g., including Talk time (min/day), Vocal biomarkers (tone, pitch), Conversation partners (#), GPS location (from smartphone)) and physical heath parameters (e.g., Step count, Sleep quality, Eating behaviors, etc.) derived, at least in part, from sensor signals and/or measured characteristics. In some embodiments, sensor outputs and surveys on smartphone apps are weighted to generate social interaction scores representative of a subject.

The ability to monitor a broad range of acoustic and linguistic features in ecologically valid settings is key in identifying individuals at increased risk for mood disorders, identifying those at risk for social isolation that may lead to increased risk of cognitive decline, and those at risk for other disorders marked by early changes in speech, voice, and language quantity/quality (e.g., early language changes in dementia Alzheimer's type, prodromal Huntington's disease, fluency changes in Multiple Sclerosis, Parkinson's disease, among others).

Acquired Neurocognitive and Neuro-linguistic disorders (e.g., aphasia, cognitive-communication impairments associated with neurodegenerative disorders with/without dementia, traumatic brain injury, right brain injury), acquired motor speech and fluency disorders, neurodevelopmental disorders, and child language disorders. The device can also be used in clinical applications in recording conversation quantity and quality in hearing loss treatment/aural rehabilitation applications. The device can also be used to monitor vocal use patterns in professional voice users and those with vocal pathologies.

The present sensor systems and methods are also useful for treatment of diseases associated with loss of muscular or neurological function such as amyotropic lateral sclerosis, Lambert-Eaton myasthenic syndrome, myasthenia gravis, Duchenne's muscular dystrophy, the sensor can be used to assess functional performance of the subject, for example, by assessing physical activity, breathing performance or swallowing performance in these conditions.

As mentioned above, the ability to quantify speech recovery in a wearable format impervious to ambient noise conditions would hold high value in evaluating the nature of and treatment outcomes for numerous disorders associated with voice, speech, language, pragmatic, and cognitive-communication disorders. Further applications include quantifying stuttering frequency and severity in individuals with fluency and fluency related disorders. The coupling to skin along the suprasternal notch enables this functionality, with minimal stigma associated with wearing the device. Recording large volumes of data from ecologically valid environments is key for advancing clinical assessment, monitoring, and intervention options for a number of disorders.

Dysphagia and Swallowing Problems: difficulty swallowing (dysphagia) remains a problem across a host of conditions that include, but not limited to: head/neck cancer, stroke, scleroderma, and dementia. Prior works have indicated the frequency of spontaneous swallowing is an independent marker of dysphagia severity. Furthermore, in hospitalized patients, the ability to determine the safety and efficiency of swallowing function is critical for identifying patients at risk for aspiration, diet modifications that optimize nutrition and prevent aspiration, facilitate timely hospital discharge and avert readmission related to aspiration pneumonia. This sensor could potentially operate as a screening tool that detects abnormal movements associated with dysphagia and/or potentially guide dietary recommendations. The improvement of dysphagia with therapeutic intervention can also be tracked with this sensor. This application could be applied across a wide range of age groups from neonates to elderly adults.

Stroke Rehabilitation: as mentioned, the sensor provides the unique ability to assess speaking and swallowing function. Both are key parameters in stroke recovery. Beyond this, the sensor can also measure gait, falls, and physical activity as a comprehensive stroke rehabilitation sensor.

Nutrition/Obesity: the preferred deployment of the sensor is via intimate skin coupling to the suprasternal notch. This enables quantification of swallowing and swallowing count. The passage of food leads to a unique sensor signature that enables us to predict for mealtime and feeding behaviors. The mechanics of swallowing differs based on the density of the food or liquid bolus being ingested. Thus, our sensor can detect the ingestion of liquids versus solids. Furthermore, our sensor can assess swallowing signals that can distinguish between the ingestion of solid foods, denser semi-liquid foods (e.g. peanut butter), or thin liquids (e.g. water). This may hold utility for food ingestion tracking for weight loss. Other uses include assessing food intake in individuals with eating disorders (e.g. anorexia or bulimia). Further uses include assessing meal-time behavior in individuals who have undergone gastric bypass—the sensor can provide warning in instances where too much food or liquids are ingested post-operatively.

Maternal/Fetal Monitoring: currently, ECHO Doppler is the most common modality to capture fetal heart rate in pregnant women. However, this modality is limited in the sense that fetal heart rate from obese patients can be difficult to capture. Furthermore, the Doppler signal is frequently lost as the fetus descends during labor. Prior work has demonstrated the potential value of mechano-acoustic sensing for fetal heart rate monitoring. Our wearable sensor system would be well-suited for this application.

Post-operative Surgery Monitoring of Bowel Function: The stethoscope is used commonly to assess return of bowel function after abdominal surgery. Bowel obstruction, or failure of bowel function return is a common cause of hospitalization or delayed discharge. A sensor capable of quantifying return of bowel function through acoustic signal measurement would have utility in this context.

Cardiology: the stethoscope is standard of care for diagnosis and disease monitoring. The sensor presented here represents the ability to continuously capture data and information derived from the stethoscope. This includes the continuous evaluation of abnormal murmurs. In certain instances such as congenital heart defects, the presence of a murmur is critical to the subject's health. The present sensor systems may provide a continuous acoustic measurement of heart function. Abnormal sounds are also reflective of heart valve disease. Accordingly, the sensors here may be used to track the stability or worsening of valve disease such as aortic stenosis, mitral valve stenosis, mitral valve regurgitation, tricuspid stenosis or regurgitation, or pulmonary stenosis or regurgitation.

Specific to cardiology, non-invasive ways to assess cardiac output and left ventricular function remains elusive. Cardiac echocardiography is non-invasive, but requires specialized training and is not conducive to continuous wearable use. A non-invasive method to continuously track cardiac output is of high clinical value for numerous conditions including congestive heart failure. Embodiments of the present sensor systems are able to provide a measure of both heart rate and stroke volume (the volume of blood pumped per beat). Cardiac output is the product of heart rate and cardiac output. This may be accomplished, for example, by assessing the time delay between peaks for heart rate. In turn, the attenuation in the amplitude of the accelerometer represents the intensity of each heartbeat by measuring the displacement of the skin with each beat.

Figure 42:
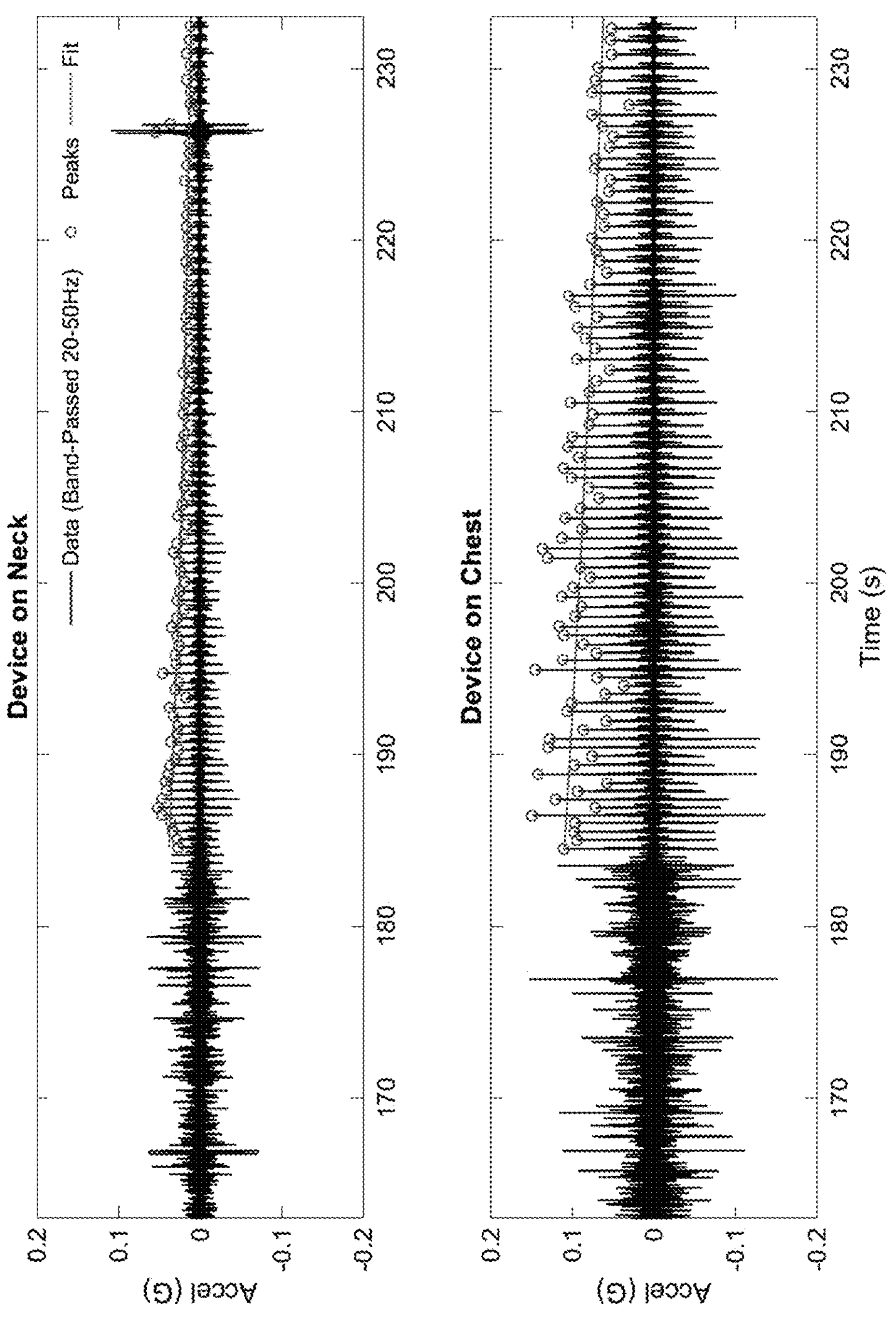
FIG. 42 provides example data for use of the present sensor systems for monitoring advanced physical performance metrics for cardiac output.

FIG. 42 provides example data for use of the present sensor systems for monitoring advanced physical performance metrics for cardiac output. As shown in the figure, after intense physical activity, the sensor is picking up an elevated heart rate but also an elevated deflection. As the user returns to baseline, the heart rate and amplitude normalizes. This is an example of how the amplitude can be used to assess and correlate to the amount of blood pumped with each heart beat.

Another embodiment is in military: Injury from a firearm or explosion leads to propagation of mechanical waves from the point of impact. The sensor can be used to assess the severity of such an impact as a way to non-invasively assess a bullets impact or proximity of the user to a blast. The sensor can also be used to assess the likelihood of damage to a vital organ (e.g. placement over the heart or lungs). The sensor may be deployed directly on the user (e.g. police officer, soldier) or in clothing or in body armor.

External Modifications:

Any of the medical devices provided herein may have one or more external modifications, including to provide access to new diagnostic and therapeutic capabilities. For instance, the addition of an external mouthpiece enables a controlled release of airflow from a user that can then be measured by the sensing elements within the sensor system (e.g. accelerometer or microphone). This enables the quantification of airflow (volume over time) without the need for expensive equipment such as spirometry. Critical parameters such as forced expiratory volume in 1 second (FEV1) could then be collected at home with the data transmitted and stored wirelessly. Changes in air-flow parameters such as FEV1 could then be coupled to other parameters such as wheeze sounds, cough frequency, or throat clearing to create novel metrics of disease that can serve as an early warning system of deterioration.

Therapeutic Applications: In respiratory diseases such as chronic obstructive pulmonary disease (COPD) or asthma, respiratory training is a key component to reducing shortness of breath (dyspnea). This includes teaching breathing techniques such as pursed lip breathing (PLB). This involves exhaling through tightly pressed lips and inhaling through the nose with the mouth closed. The length of inspiration and expiration are also adjusted to meet the patient's unique respiratory status. The length of expiration and inspiration can be adjusted depending on user comfort. The sensor can then be deployed in a therapeutic manner to distinguish mouth breathing from nose breathing by variations in throat vibration or airflow. The sensor can also time the length of inspiration and expiration. A respiratory therapist could set an ideal time length for instance and the sensor can provide haptic feedback to the patient/user of when an ideal inspiratory or expiratory time length is reached. Overall, the sensor can act as a 'wearable' respiratory therapist that reinforces effective breathing patterns and techniques to improve breathing and patient symptoms, and prevent exacerbations of respiratory diseases. Further work could couple this with continuous pulse oximetry.

Alzheimer's Dementia:

Alzheimer's dementia (AD) affects 5.4 million Americans, costs $236 billion dollars in yearly spending, and requires a collective 18.1 billion hours of care from loved ones. 1 Reduced social interaction or loneliness is a key accelerator of cognitive decline, and directly increases the risk of depression in patients with AD. Second, quality social interaction is associated with reduced risk of dementia later in life offering a non-pharmacological strategy to reduce the morbidity and mortality of AD. Third, social interaction and conversation changes represents a potential biomarker for early identification of AD and disease progression. A major barrier in advancing the use of social interaction in AD patients has been the lack of tools capable of comprehensively assessing the amount and quality of social interaction in real world settings. Social interaction rating scales (self-report/proxy report) are subject to reporting bias and lack sensitivity. Smartphones have limited sensing accuracy, exhibit variability in sensor performance between manufacturers, lack the ability to measure key parameters (e.g. meal time behavior), and suffer poor audio fidelity in noisy ambient settings. While devices to measure social interaction have been reported in the literature, those systems are bulky and heavy precluding continuous use, and lack the comprehensive sensing capabilities necessary to adequately capture the entire spectrum of parameters in social interaction. Furthermore, these systems have not been validated rigorously in the elderly population where technical literacy is low.

To advance the care of patients with AD, there is a need for wearer-accepted, non-invasive, remote monitoring technology capable of tracking the broad range of parameters relevant to social interaction across mental, social, and physical health domains. To address this, we propose the development of the first integrated wearable sensor capable of continuous measurement of critical parameters of social interaction in a networked environment that minimizes user stigma through an optimized wearable form factor. The current prototype incorporates a high-frequency 3-axis accelerometer capable of measuring speech, physiological parameters (e.g. heart rate, heart rate variability), sleep quality, meal-time activity and physical activity (e.g. step count) in ecologically valid environments through additional signal analytics. The sensor is completely enclosed in medical-grade silicone that is less than 4 mm thick with bending and moduli parameters orders of magnitude lower than previously reported technologies. The sensor, adhered to the suprasternal notch with hypo-allergenic adhesives, enables unobtrusive, intimate skin connection allowing our technology to collect mechano-acoustic signals invisible to wristband based sensors and smartphones. This includes the ability to measure respiration rate, heart rate, swallowing rate, and talk time with accuracy unachievable by other technologies. We propose the development of a fully-integrated social interaction sensor with additional functionality, designed rationally with the input from AD patients and their caregivers and validated against clinically standard equipment, with more advanced signal processing. The estimated cost of each sensor is <$25 USDs with a total addressable yearly market of $288 million USDs yearly. Aim 1 will add an integrated microphone to our existing wearable, flexible sensor platform that already includes a high-frequency 3-axis accelerometer capable of continuous communication via Bluetooth®. The success criteria will be successful bench testing showing high-fidelity audio capture from the full range of 38 dB (whispers) to 128 dB (concert) inputs, and successful wireless data transfer to a HIPAA secure database. A user interface is provided for researchers to enable more advanced analytics. Additional parameters may be extracted: pitch, tone, speech paucity, overtalk time, and conversation turn-taking count.

The development of the first truly wearable social interaction sensor capable of continuous, multimodal, and real-world sensing represents an important innovation, including for the AD research community, as an observational tool, and to patients and their caregivers as ah interventional tool. By accurately, reliably, and discretely capturing the numerous parameters relevant to social interaction, we hope our sensor can detect social isolation in individuals with AD and provide subtle feedback that encourages more engagement and reduces loneliness.

Alzheimer's dementia (AD) affects 5.4 million Americans, represents the 6th most common cause of death increasing 71% from 2000 to 2013, costs $236 billion dollars in yearly spending, and require a collective 18.1 billion hours of care from loved ones yearly. There are limited therapies (behavioral and pharmaceutical) for AD with numerous candidates failing in late stage clinical trials. Advancing the next generation of AD therapies depends on high-quality clinical measurement tools for detecting novel, ecologically valid, and sensitive biophysical markers of cognitive decline. As the search for new therapies continues, there is an urgent need for alternative strategies that bend the disease trajectory by addressing social interaction contributors and consequences associated with AD. Central to these strategies is the recognition that loneliness and social isolation pose serious threats to the health of older adults, leading to self-harm, self-neglect, cognitive disability, physical disability, and increased mortality. Addressing modifiable risk factors, specifically social isolation, is a major policy goal of public health institutions and governments to mitigate the tremendous burden of AD. A large body of rigorous research supports the protective effects of high quality social interaction in mitigating the deleterious effects of AD and in optimizing healthy aging (mental, physical, and social). Increased conversation difficulties such as breakdowns in message exchanges between interlocutors or increased time required to convey and to understand messages manifest early in AD, result in increased social isolation, which accelerates cognitive decline; and add significantly to caregiver burden in AD. Additionally, because the natural course of AD is marked by periods of disease stability, punctuated with periods of rapid decline, measuring social interaction changes longitudinally would facilitate a deeper understanding of the natural progression of AD. Conversation and social interaction behaviors extracted from real-world communication contexts are promising next generation biophysical markers of cognitive change and treatment outcome measures. Despite their significant clinical importance, changes to conversation abilities and social interaction in real-world contexts are not easily evaluated during clinical visits. Clinicians must rely on patient and proxy reports that are subject to inaccuracies and reporting biases. Developing a reliable, non-invasive, user-accepted wearable technology for collecting conversation and social interaction data would be an invaluable tool for the field. Currently, there is no existing commercially available technology capable of measuring the wide range of parameters relevant for social interaction in a form factor that enables long-term, real-world use in individuals with AD. Accordingly, any of the devices and methods provided herein may be used in AD evaluation, diagnosis and therapy.

Parameters of Importance for Social Interaction (Physical, Mental, and Social): Social interaction is a complex construct. Prior research links social interaction to cognitive function, mental health, sleep quality, physical activity, social activity, eating behaviors, and language use in dementia. Thus, assessment of social interactions requires tools capable of collecting numerous behaviors within a naturalistic environment.

(1) Physical functioning: physical activity, sleep quality, mobility spheres are all relevant to social interaction.

(2) Phonatory features: speaking rate, talk time, voice pitch, tone, pausing, intensity, intelligibility, and prosody that reflect aspects of mood as well as sources of conversation breakdown.

(3) Meal time behaviors: meal frequency, hyperphagia or hypophagia using swallow frequency counts.

(4) Conversation and linguistic behaviors from the person with dementia and their interlocutors: number of turns, turn duration, overtalk (when one partner speaks over another), conversation breakdowns and repairs, topic maintenance, word retrieval difficulty.

Assessing collecting social interaction in adults typically involves self-report and proxy-report psychometric surveys (e.g. Friendship Scale, Yale Physical Activity Scale, SF-36). However, this method of data collection is prone to bias, lacks sensitivity, and is frequently inaccessible by individuals with cognitive and language impairments. Moreover, psychometric survey tools, in isolation, do not reflect the changes in conversation abilities that frequently underlie social interaction changes in aging and dementia. Consequently, survey tools are best considered in conjunction with objective measures of conversation changes in real-world environments. Smartphones with custom mobile apps have been explored previously for this purpose. Elderly individuals are the least likely to use smartphones and exhibit lower technical literacy. However, smartphones offer some advantages including wide availability, onboard sensors (e.g. accelerometer, microphone), and wireless communication capabilities. While previous studies have shown that smartphone collected data (text message and phone use) correlates with traditional psychometric mood assessments, the overall accuracy of these smartphone-based remains poor (<66%). While there is compelling evidence that voice, conversation, and linguistic features are sensitive markers of mood, cognitive-linguistic, and social interaction changes, smartphone audio recordings are of insufficient quality for clinical monitoring of these behaviors particularly in the context of real-world situations with high ambient noise. Furthermore, there remains accuracy concerns of smartphone based accelerometers for monitoring physical activity and sleep. The large number of available smartphone platforms with their distinct hardware specifications precludes the ability to normalize data inputs. Commercially available systems attached to the wrist (e.g. FitBit®) are largely limited to tracking step counts and thus do not capture mobility sphere data. While remote data recording systems such as LENA offer more advanced signal processing, they have been tested only in parent-child social interactions, limited to only speech collection, and have not demonstrated the ability to capture important speech features in AD. For instance, measuring 'overtalk' time, a primary source of conversation breakdowns and a negative behavior evinced by healthy conversation partners, is important in the context of AD. The most advanced system reported in the literature for social interaction includes both an accelerometer and microphone in a strap-on device. However, the system is bulky making daily wear infeasible, raises the concern of user stigma, and requires quiet ambient conditions to operate. Furthermore, these systems are not able to collect relevant physiological parameters (e.g. heart rate, heart rate variability, respiration rate) for social interaction. Since mealtime behaviors are associated with alterations in mental health and social interaction, a number of groups have reported wrist-based and neck-based sensors to measure hand movements and chewing/swallowing behaviors but only modest accuracy. These eating behavior sensors lack the ability to collect other relevant parameters such as speech, physical activity, or physiological metrics. Currently, there is a critical need for a technology that is capable of providing objective, comprehensive and unobtrusive measurements that capture the wide range of parameters important to social interaction for individuals with AD.

Recent advances in materials science and mechanics principles, have enabled a new class of stretchable, bendable, and soft electronics. These systems match the modulus equivalent to skin enabling mechanically invisible use for up to 2 weeks with coupling to any curvilinear surface of the body. The intimate coupling with skin, similar to a temporary tattoo, enables physiological measurements with data fidelity comparable to FDA-approved medical devices. Specifically, mechano-acoustic signals are of high clinical relevance. The propagation of mechanical waves through the body, measureable through the skin, reflects a range of physiological processes including: opening/closing of heart valves on the chest, vibrations of the vocal cords on the neck, and swallowing. Thus, a wearable sensor intimately connected to the skin is key to sensing these bio-signals and enabling a broad range of sensing possibilities. This is contrast to external accelerometers embedded in smartphones and wrist-based to traditional "wearables", which are limited to measuring only basic physical activity metrics (e.g. step count). Described are the use of high-frequency accelerometers coupled to the skin to sense a wide range of parameters relevant to assessing social interaction.

We present a novel mechano-acoustic sensing platform (FIG. 19) that incorporates the most advanced concepts in stretchable electronics adhered on the suprasternal notch capable of providing continuous measurement, storage and analysis of key parameters of social interaction in a distributed network. The mechano-acoustic system incorporates filamentary serpentine copper traces (3 μm) placed between layers of polyimide encapsulation connecting small-chip components. The central sensing unit is a high-frequency 3-axis accelerometer that can capture low frequency signals from a fraction of 1 Hz (e.g. step count, respiration rate) to high frequency signals up to 1600 Hz (e.g. speech) all operating with ultra-low power consumption. This ability to sample high-frequency signals is in stark contrast to the majority of commercially available accelerometer based sensors (e.g. Actigraphy/FitBit®) that operate only in the low-frequency range. The resulting devices have a mass of 213.6 g, a thickness of 4 mm, effective moduli of 31.8 kPa (x-axis) and 31.1 kPa (y-axis), and bending stiffness of 1.02 μN m (x-axis) and 0.94 ρN m (y-axis), which correspond to values that are orders of magnitude lower than those previously reported enabling long-term wear. The entire system floats within an ultra-low modulus elastomeric core (Silbione RT Gel). Another thin layer of ultra-low modulus silicone (Ecoflex) serves as a shell that reduces skin surface contact stress, which maximizes user comfort and water protection.

This platform provides a system that employs a high-frequency accelerometer intimately mated to the skin enabled by low-modulus construction and robust adhesion capable of multimodal operation. The system may use Bluetooth® to communicate with the smartphone, although the smartphone largely serves as a visual display and additional data storage unit. The current system can also engage, in an additive fashion, with a smartphone's sensors including the microphone if desired.

Figure 21:
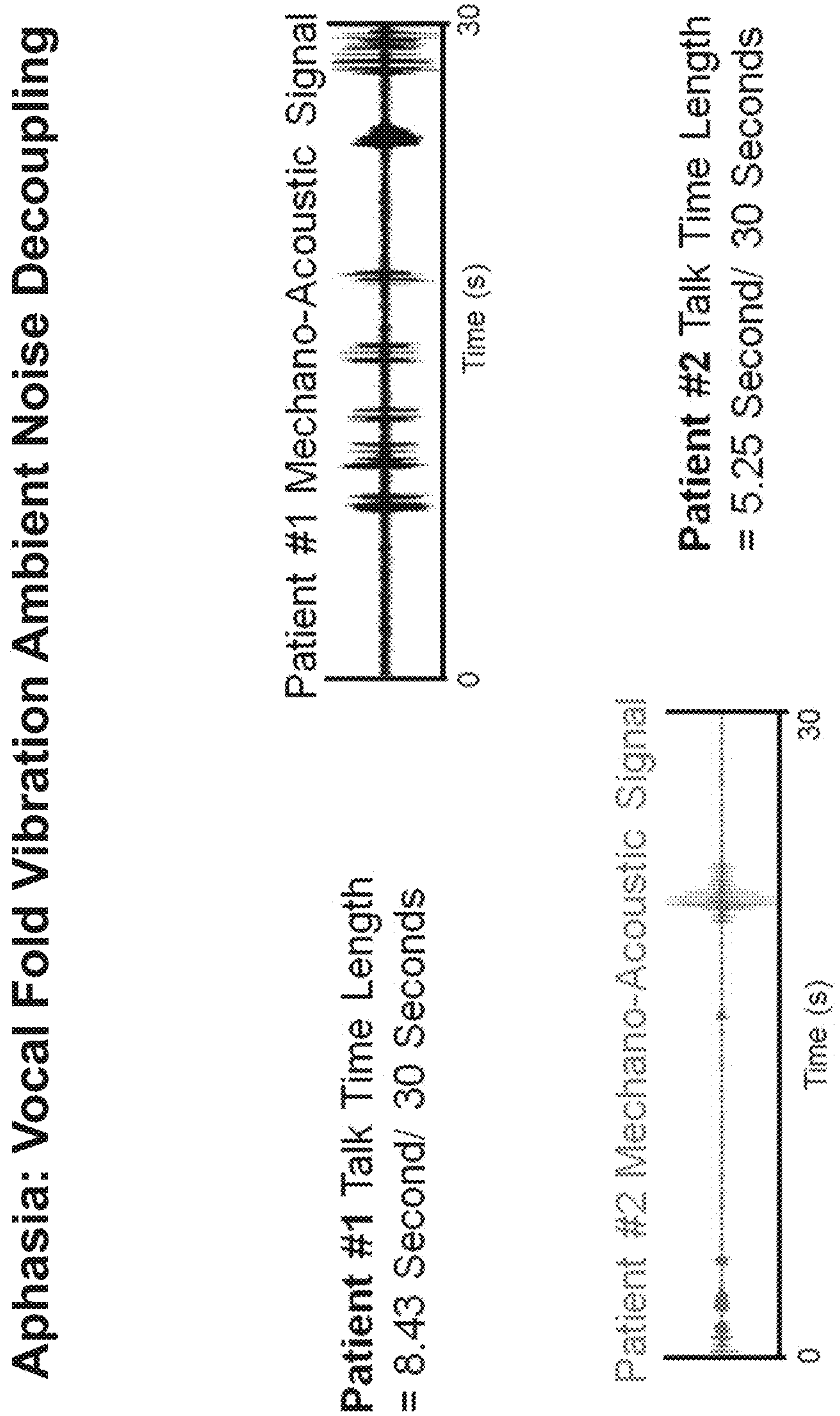
FIG. 21 demonstrate the system's ability to identify specific interlocutors and quantify talktime in a group of 3 stroke survivors with aphasia and one speech language pathologist.
Figure 22:
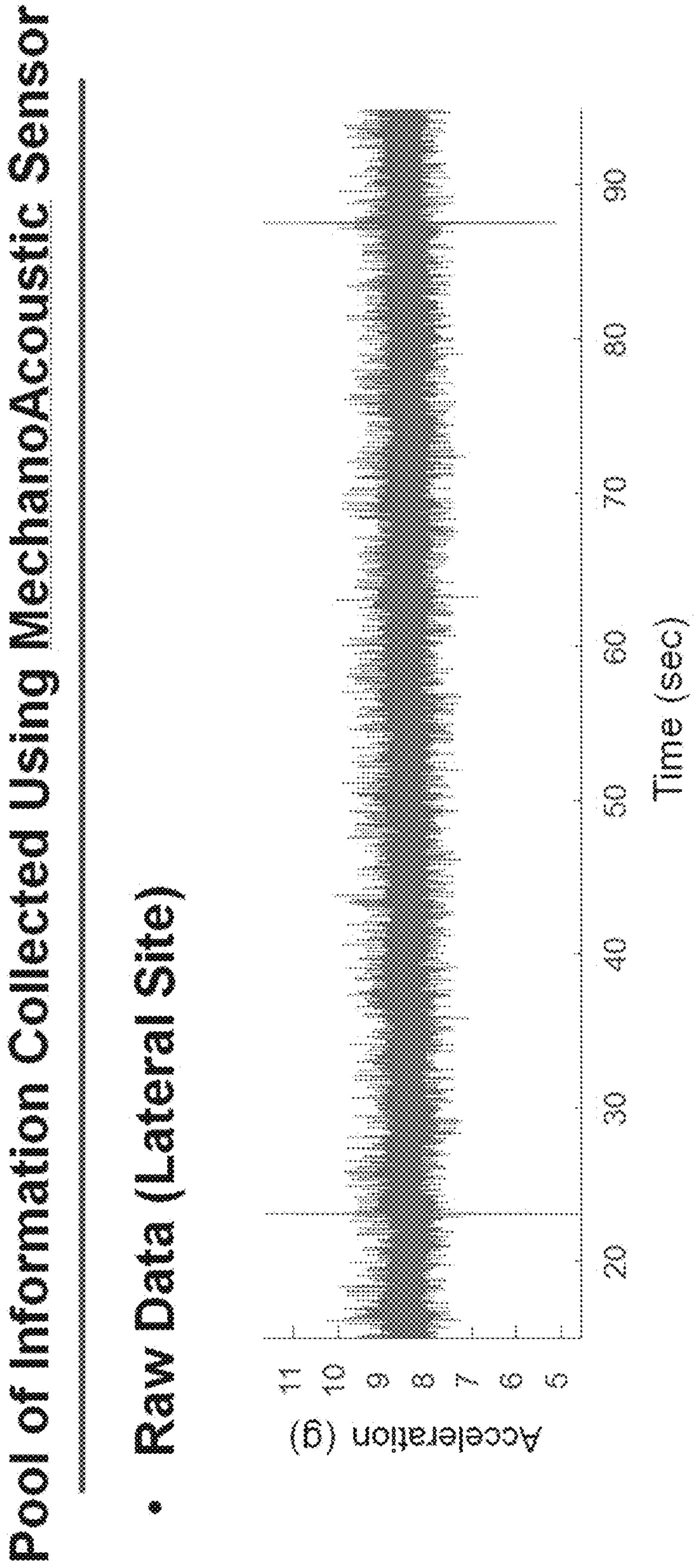
FIG. 22 provides an example of a raw data signal collected by an epidermal mechano-acoustic-electrophysiological measurement/therapeutic device.
Figure 23:
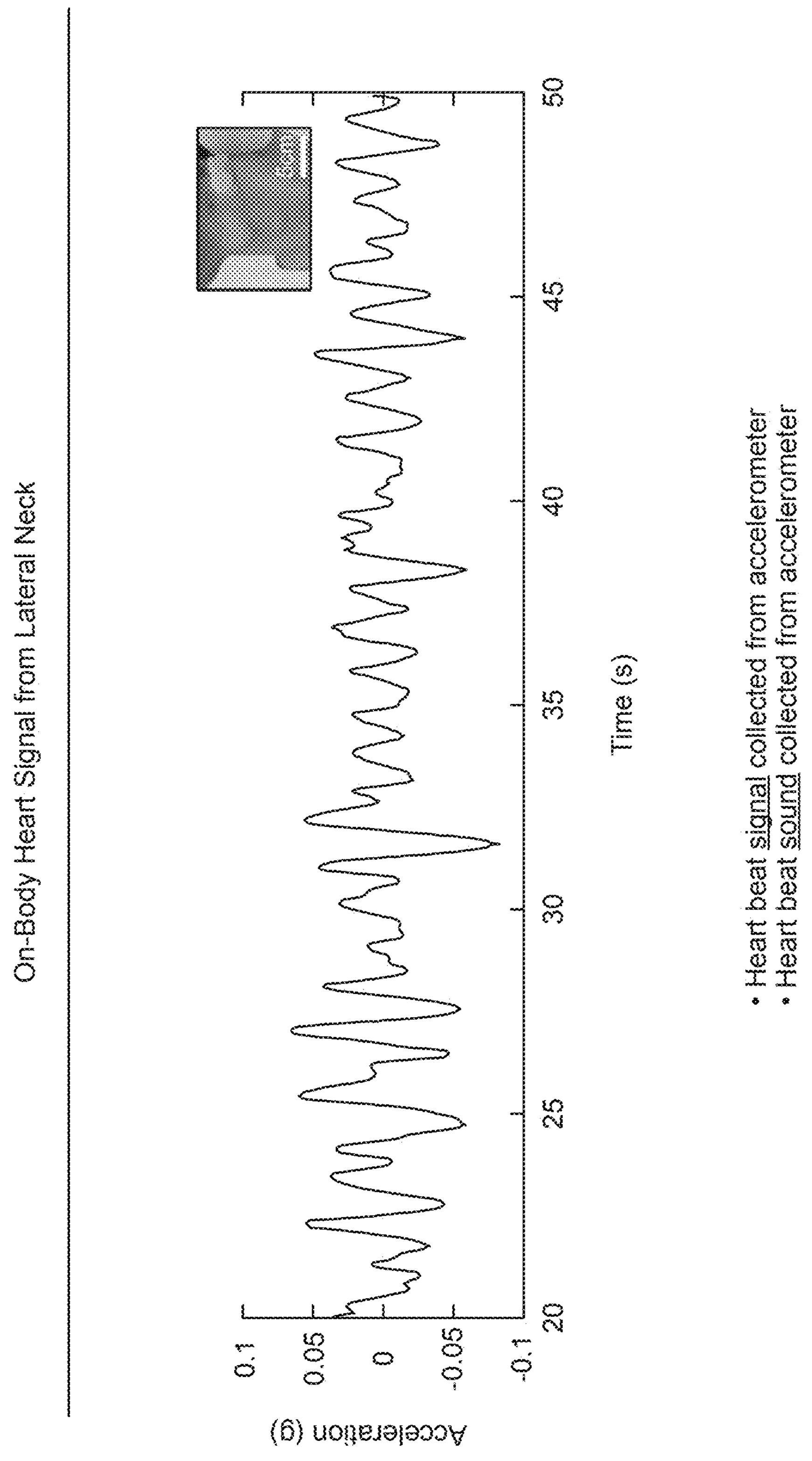
FIG. 23 provides example data of on-body heart signal collected from the lateral neck.
Figure 24:
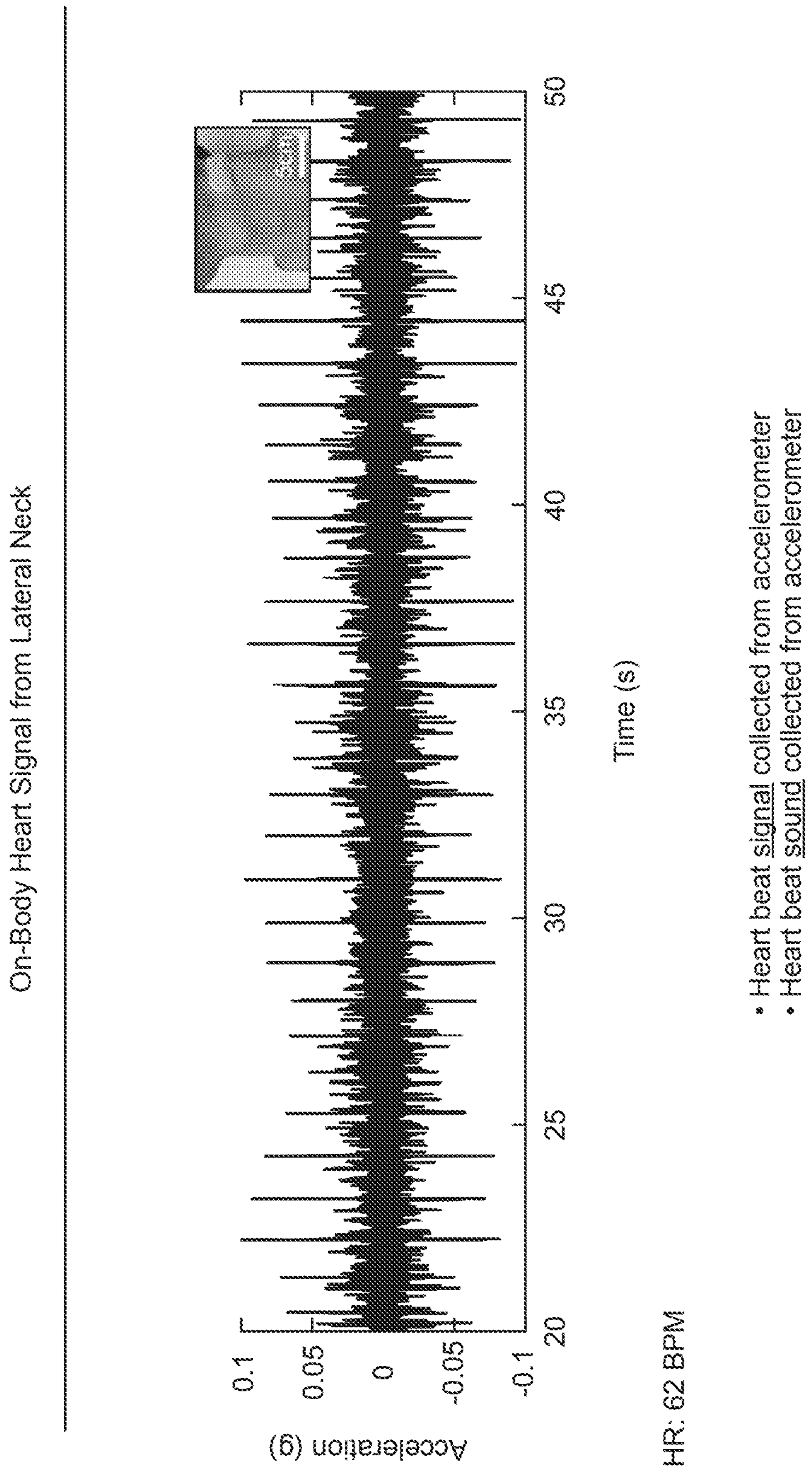
FIG. 24 provides example data of on-body heart signal collected from the lateral neck.
Figure 25:
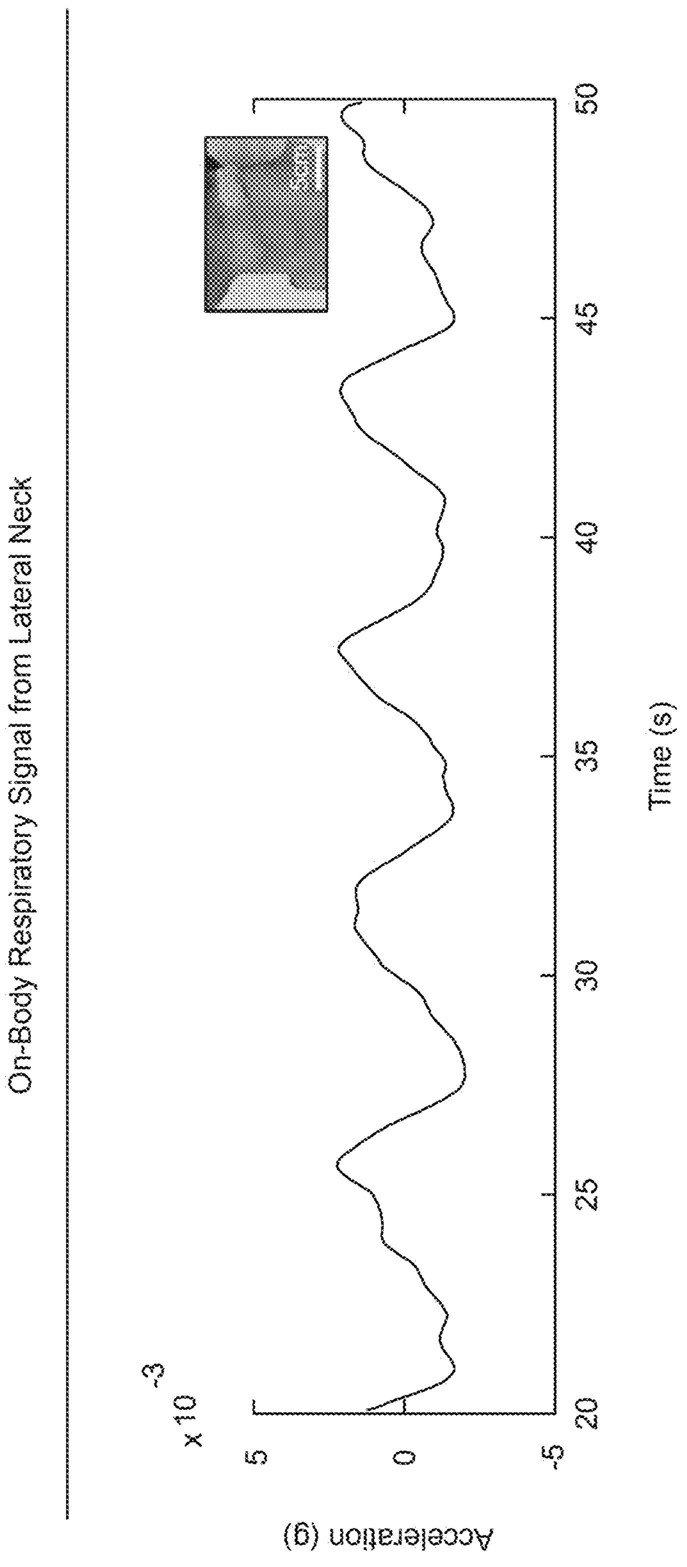
FIG. 25 provides example data of on-body respiratory signal collected from the lateral neck.

Software and Signal Analytics for Novel Data Collection Relevant to Social Interaction: Provided is a suite of signal processing capabilities that involves bandpass filters of the raw acousto-mechanic in selective ranges within the accelerometer's bandwidth enabling multimodal sensing for numerous biomarkers, from step counts and respiration (low band of the spectrum), to swallowing (mid band of the spectrum), and speech (high band of the spectrum). The intimate skin coupling enables the highly sensitive measurement with high signal to noise ratio. This allows the sensor to measure both subtle mechanical activities and acoustic bio-signals that are below the threshold for audible level with conventional microphones. We demonstrate the ability to use our acousto-mechanic sensor to detect the words (left, right, up, and down) by differentiating their time-frequency characteristics from vocal cord vibrations associated with the creation of each word. This ability can then be used by the sensor to control a computer game (e.g. Pacman). In the case of talktime calculations, the raw mechano-acoustic signal is filtered with an eighth-order Butterworth filter. The filtered signal is then passed through a root-means square value threshold. The energy of the signal is then interrogated with a 50-ms window enabling the determination of talktime and word count. A Short Time Fourier Transformation defines the spectrogram of the data. The results are averaged and reduced in dimensionality using principal components analysis to form a feature vector. Finally, the feature vector is classified using linear discriminant analysis. We demonstrate the system's ability to identify specific interlocutors and quantify talktime in a group of 3 stroke survivors with aphasia and one speech language pathologist (FIG. 21).

Figure 26:
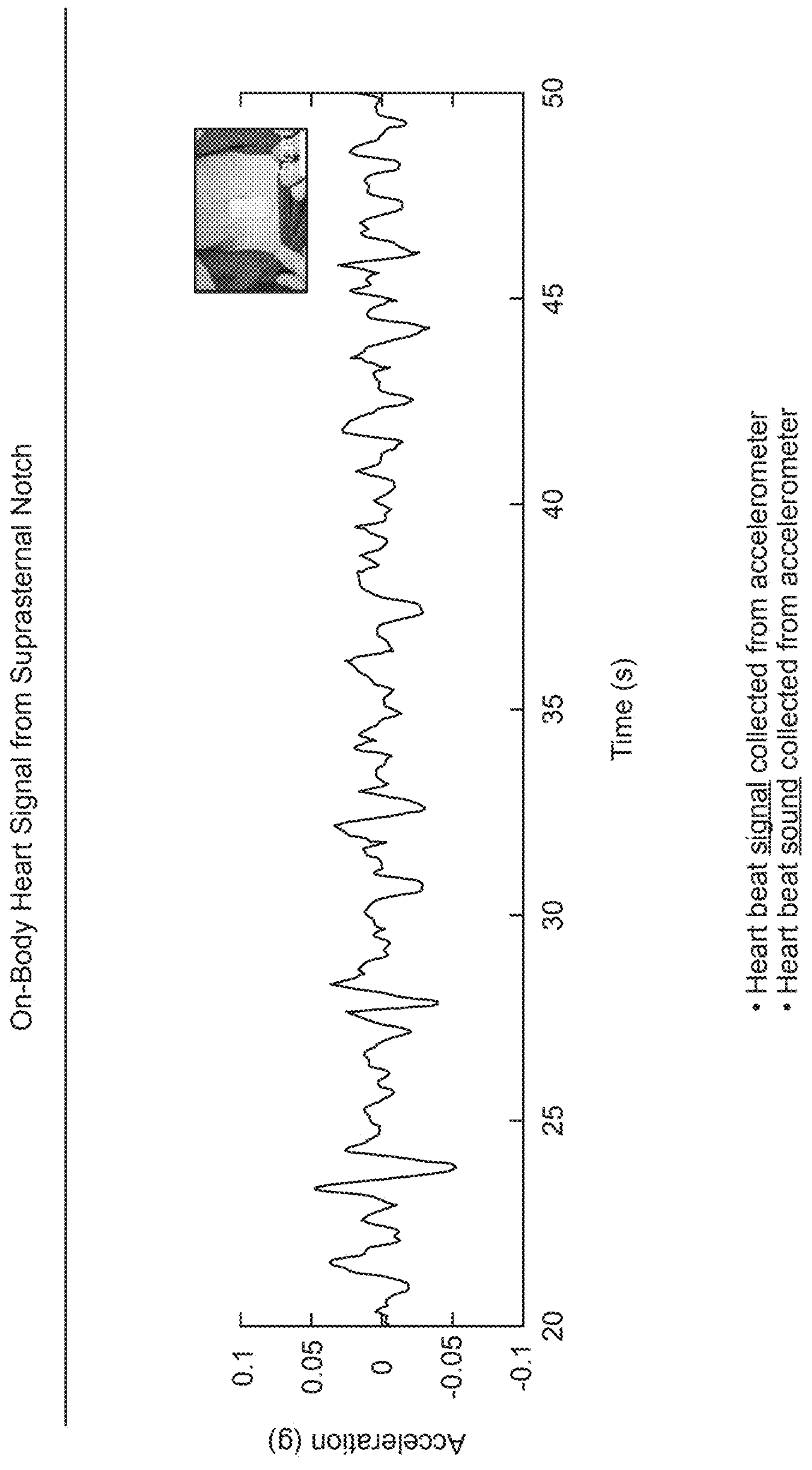
FIG. 26 provides example data of on-body heart signal collected from the suprasternal notch.
Figure 27:
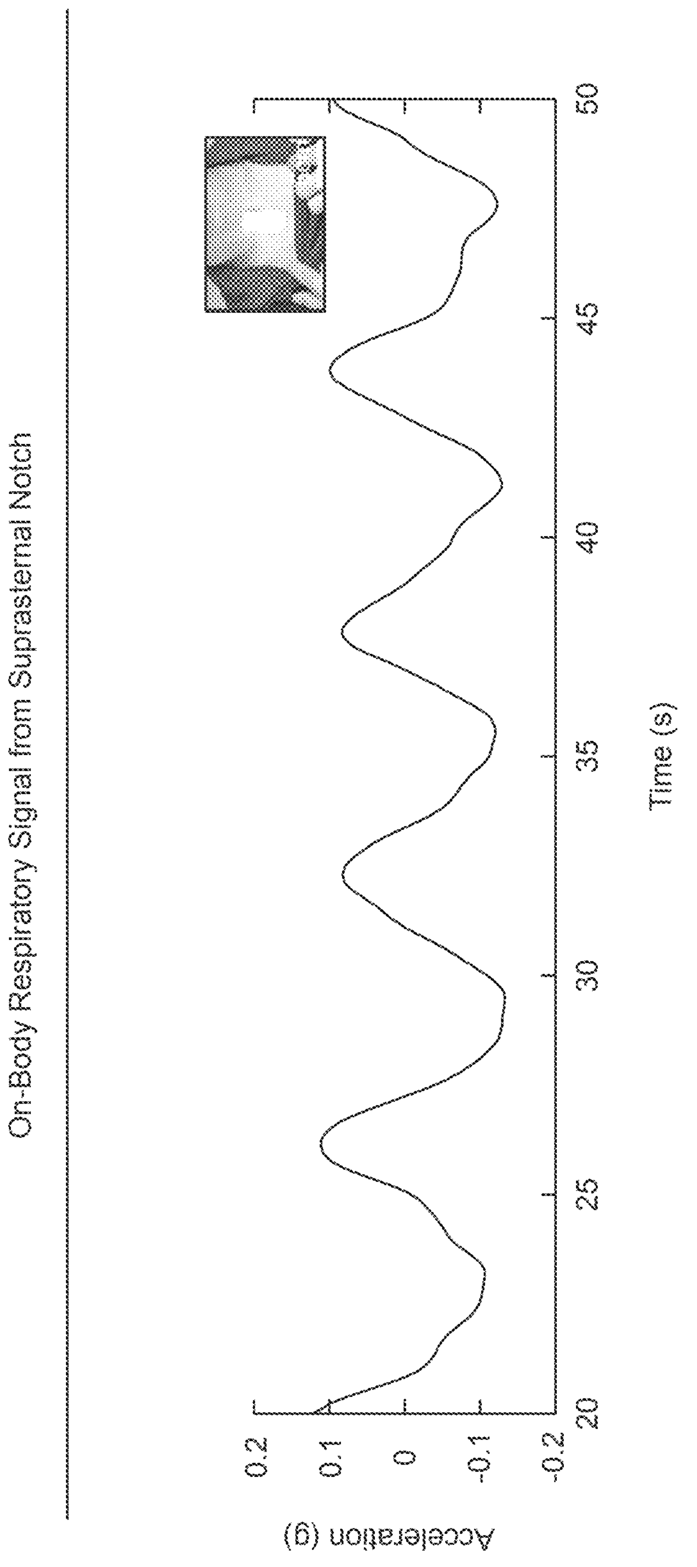
FIG. 27 provides example data of on-body heart signal collected from the suprasternal notch.
Figure 29:
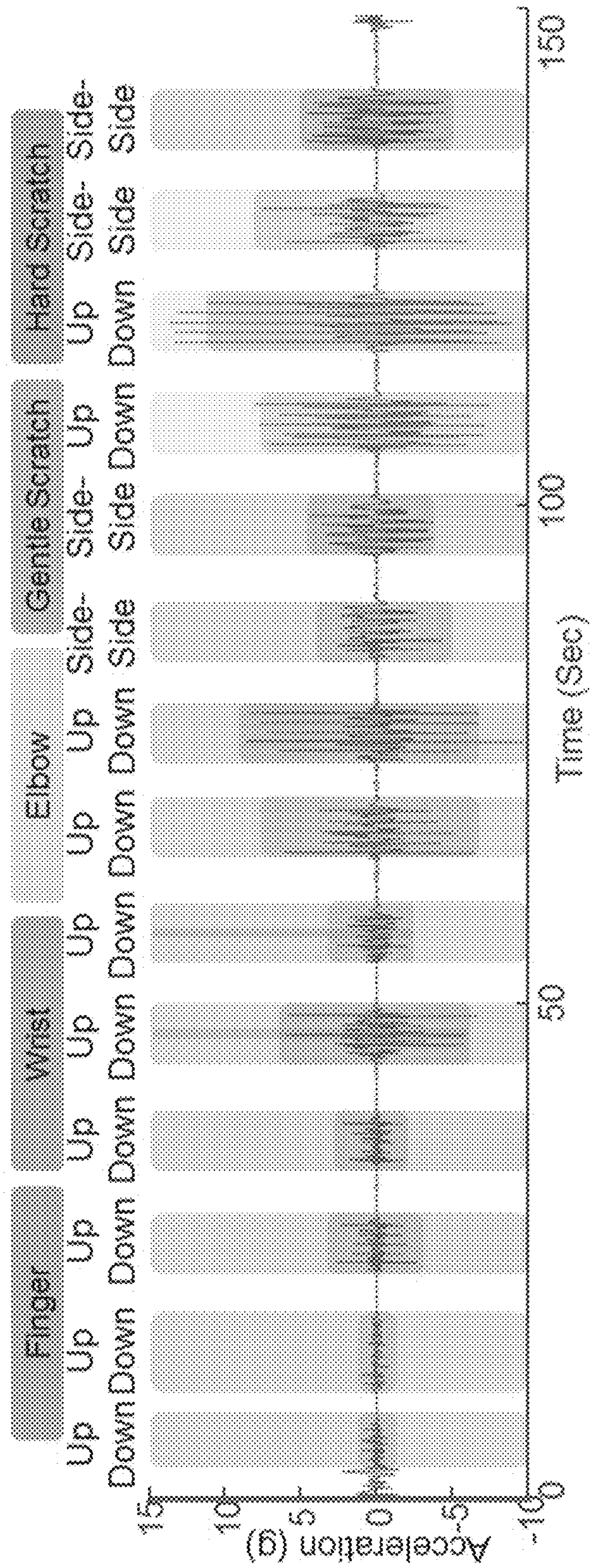
FIG. 29 provides example experimental results for measuring patient scratching using the device provided in FIG. 28.

Another key advantage is the ability to couple acoustic and mechanical signal collection in synchrony allowing for the capture of talktime specific to a wearer in both noisy and quiet ambient conditions. We demonstrate the minimal performance differences of our sensor in quiet and noisy conditions in comparison to a smartphone microphone (iPhone 6, Apple, Cupertino). This overcomes a fundamental limitation of other technologies that struggle to capture true user talk time in noisy ambient conditions. Also, the unique IDs applied to each sensor allows us to discern the number of conversation partners Beyond acoustic signals, the sensor has the capability of leveraging additional analytics to measure other parameters relevant to social interaction through its intimate skin connection. As reported previously from studies employing signal processing strategies from electrocardiograms and acoustic signals derived from stethoscopes, we employ Shannon energy calculations to induce higher contrast to the pronounced mechano-acoustic signature in the time domain from signal noise. Savitzky-Golay smoothing functions are then applied to form an envelope over the transient energy data. Examples of the advantage of this system includes measurement of respiration rate transmitted through the neck and the pulsation of arterial blood through the external carotid arteries—measures such as a heart rate, heart rate variability and respiratory rate are relevant in assessing sleep quality (FIGS. 26-27). The sensor also has the capability to measure simpler sleep quality metrics such as duration, restlessness, and sleep onset. Furthermore, our system has demonstrated an ability to calculate swallowing count, which provides direct insight into meal-time behaviors and can provide surrogate markers of hyperphagia or hypophagia (FIG. 10) as well as meal duration. Finally, the sensor can determine daily physical steps as a measure of physical activity comparable to existing commercial systems Form Factor—Reducing Caregiver and Wearer Burden and Stigma: The sensor's flexible platform maximizes user comfort with neck movement, talking, and swallowing. Highly visible neck-based sensors (necklaces and circumferential neck sensors) are another limitation for other published solutions. 79% of respondents expressed significant reluctance and concern in regards to wearing a neck-based sensor daily. Thus, a highly wearable sensor capable of capturing the necessary parameters must minimize potential stigma for the person with AD and their interlocutors. Prior qualitative studies of user acceptance of wearables in AD highlight the importance of low device maintenance, data security, and discreteness in wear. The deployment of the sensor on the suprasternal notch with a medical-grade adhesive is a key advantage in user acceptability in that it enables capture of the relevant signals transmitted from the speech production system, while being largely covered by a collared shirt. The sensor is also encapsulated with silicone that can be matched to the user's skin tone. Finally, the sensor accommodates full wireless charging and waterproof use enabling bathing with the device in place. In regards to adhesive choice to maximize wearer comfort, we have extensive experience identifying the optimal adhesive that can be adjusted based on the desired length of use (1 day to 2 weeks). Given the heightened fragility of mature skin, we currently employ a gentle acrylic polymer matrix adhesive (STRATGEL®, Nitto Dento) that operates without causing significant skin irritation or redness with prolonged daily use (>2 weeks) in healthy adults. In summary, the key advantages of the wearable acousto-mechanic sensor for social interaction compared to existing systems and prior reported research include:

Multimodal Functionality: the sensors already have demonstrated the ability to collect the largest number of parameters of value to assess social interaction in one technology platform enabled through intimate skin coupling. Parameters include: talktime, # of conversation partners, swallow count, respiration rate, heart rate, sleep quality and physical activity. Additional parameters are compatible with the devices and methods provided herein.

Real-World Continuous Sensing: the sensor can measure sound only when mechanical vibrations are sensed on the user's throat enabling highly specific recording of true user talktime regardless of noisy or quiet ambient environments. This enables real-world deployment outside of controlled clinical settings.

Low Burden, Unobtrusive Form Factor: the sensor passively collects data without the need for user adjustment. Wireless charging limits user burden facilitating adherence. Deployment on the suprasternal notch enables high fidelity signal capture without the stigma of a highly visible neck-deployed system.

Advanced Signal Analytics: various signal processing techniques may be employed to derive additional metrics meaningful to social interaction.

Hardware may be employed within flexible wearable platforms. Currently, the central microprocessor has up to 8-analog channel inputs with 2.4 GHz 32 bit CPU with 64 kB RAM. Off-the-shelf microphones may be used to determine ideal specifications. Specifically, the MP23AB01DH (STMicroelectronics) series offers a thin profile microphone MEMS system (3.6 mm×2.5 mm×1 mm) that will not add any additional bulk to the wearable form factor. Furthermore, the system is low-power (250 μA) and exhibits a high signal-to-noise ratio (65 dB) with a sensitivity as low as 38 dB. The microphone can operate in synchrony with the 3-axis accelerometer to collect external audio signals. The current lithium-ion battery has 12 mAh capacity. Thus, we do not expect the additional of an external microphone to significantly affect battery life. To determine success the microphone's performance and auditory clarity is tested with a standardized block of audio text (60 s) of increasing levels of decibels (10) from 38 dB (whisper) to 128 dB (concert).

Software and Signal Analysis Augmentation—Bluetooth® may be used to connect to any standard smartphone, tablet or laptop. The user interface may display the raw signal, and data storage. The sensor may also be used as an observational tool for social interaction, including by use of a secure, researcher-focused user interface. This includes software protocol that enables HIPAA compliant data transfer and cloud storage—we have previously used Box® as a HIPAA compliant storage platform for our wireless sensors. While signal processing (Savitzky Golay filtering, Butterworth filtering, and Shannon Energy Envelop techniques) has enabled the derivation of numerous important metrics of social interaction, additional signal processing functionality will derive additional more advanced metrics. For instance, paralinguistic features such as a user's pitch, tone, and verbal response time in a conversation have all been correlated to depression including within the dementia population. Turn-taking and overtalk are additional metrics of interest. We propose a multi-pronged approach that includes employing hidden Markov model approach, open access speech processing algorithms (e.g. COVAREP), 58 and wavelet analysis. Specifically, we believe wavelet analysis is the most promising strategy given the well-established theory of prior work—a mother wavelet for any specific metric of interest will be classified from the raw input acousto-mechanic signals. The user interface allows researchers considerable freedom to manipulate the raw data various and deploy various signal processing strategies and toolboxes of interest. Further signal analysis would enable classification of other relevant behaviors for individuals with AD such as personal hygiene (brushing teeth), chores, or driving.

While the wearable global medical device is >$3 billion USDs with 20% growth over the next decade, the elderly population is highly underserved despite greater needs. The platform provided herein is applicable to a wide range of dementia indications, and additional sensing applications (e.g. sleep or dysphagia sensor). Dementia, including AD is a devastating condition. Increasing meaningful social interaction represents an immediate strategy to reduce cognitive decline and morbidity for AD while simultaneously providing a potential prophylactic strategy in the elderly. The wearable medical sensors provided herein have the opportunity to become a critical clinical outcomes tool for AD researchers by providing the first technology capable of comprehensively assessing social interaction in naturalistic environments. Furthermore, this sensor can directly help individuals and their caregivers—in days when a person with AD has not been spoken to or engaged with meaningfully, the sensors provided herein can notify the appropriate person and reduce loneliness for that day.

Example 1: Exemplary Epidermal Devices Employing Mechano-Acoustic Sensing and Actuation Exemplary devices employing mechano-acoustic sensing and actuation were fabricated and tested with respect to overall functionality and mechanical properties.

Figure 43A:
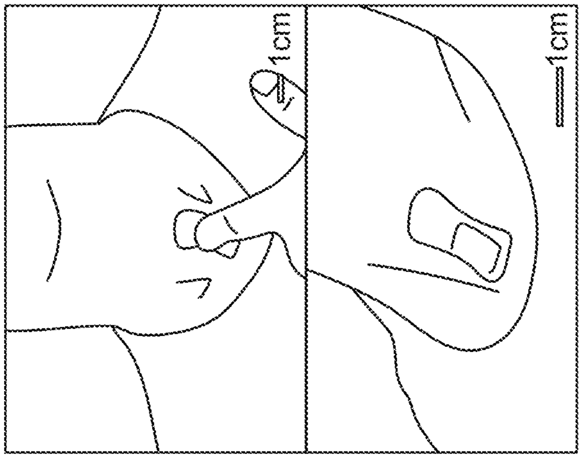
FIGS. 43A-43E. Mechano-acoustic device.
Figure 43B:
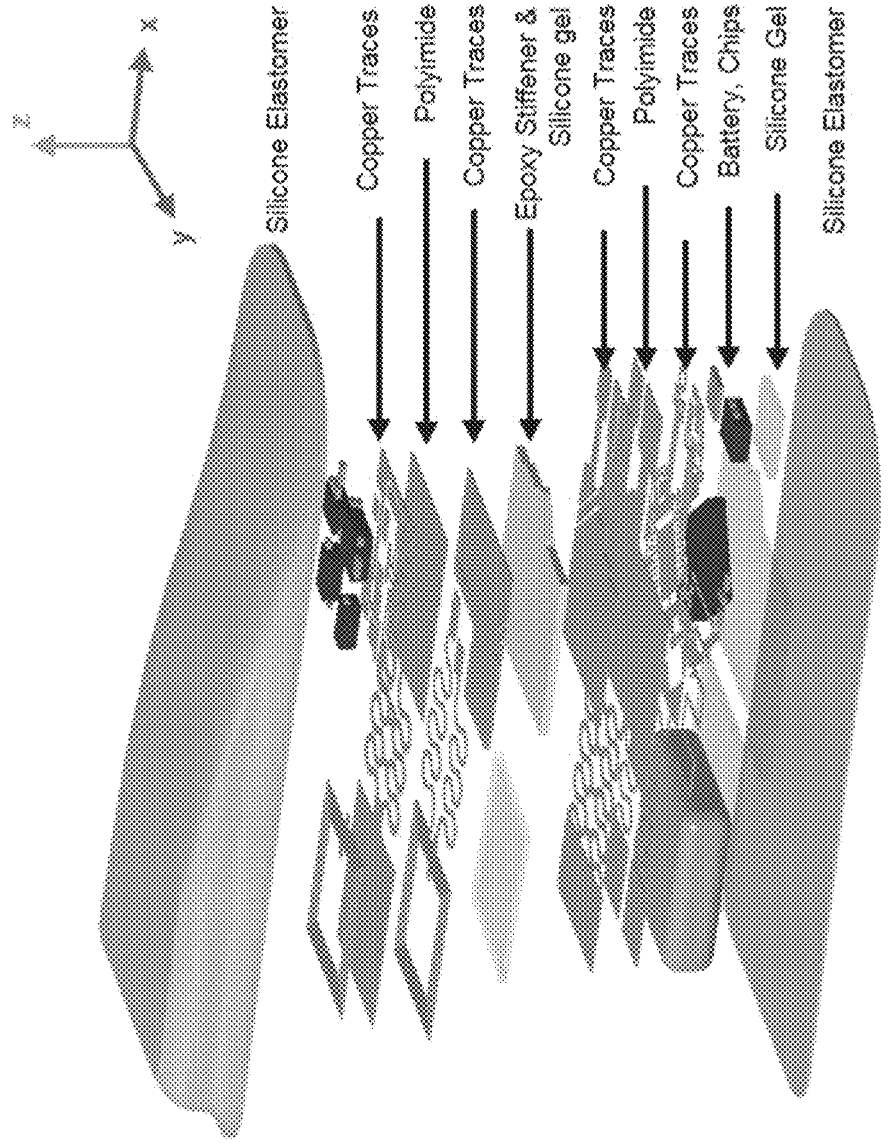
Figure 43C:
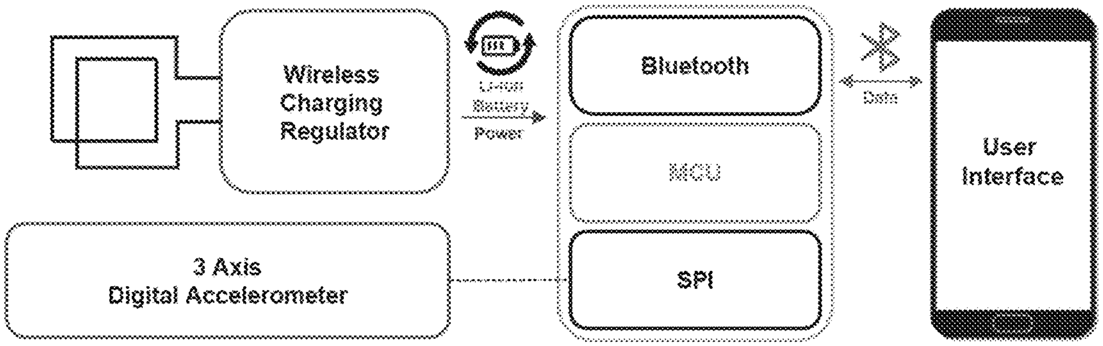
Figure 43D:
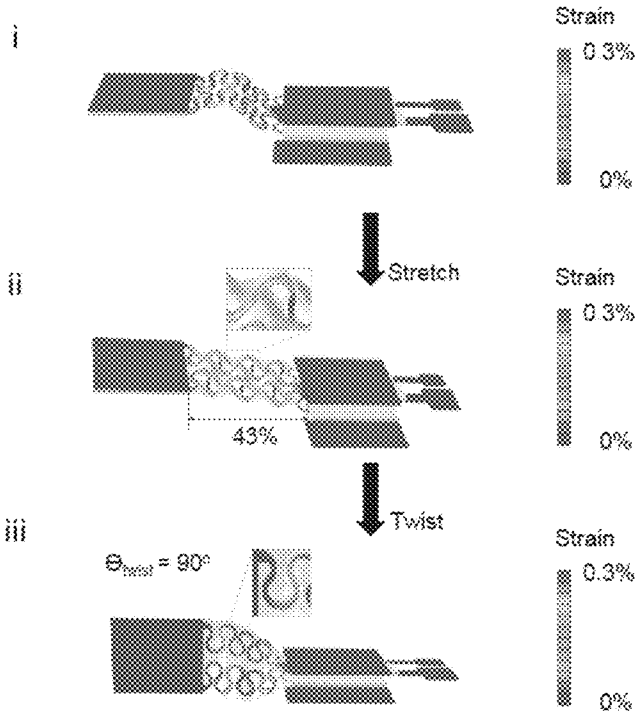
Figure 43E:
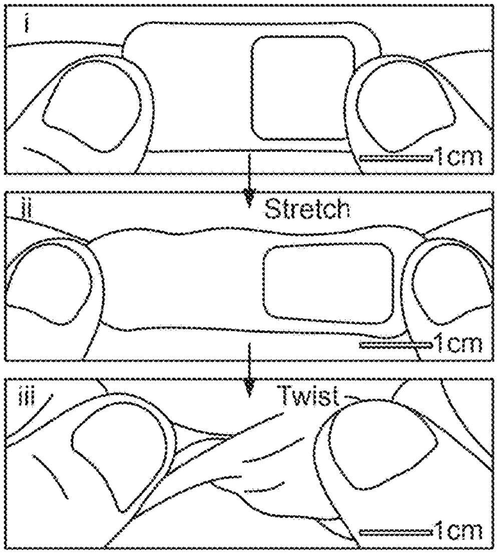

FIG. 43B provides an exploded view of a mechano-acoustic device of the invention for epidermal sensing and actuation. As shown in the figure, a mechano-acoustic sensor is encapsulated in silicone elastomer substrate and superstrate (e.g. overlayer) components and include silicone gel layers to provide an overall multilayer floating device architecture. As shown the multilayer device comprises IC components, power sources (e.g, battery), traces including contact and interconnect components (e.g., flexible serpentine interconnects and contact pads), and interlayers (e.g., polyimide layers). The multilayer architecture and device components are arranged to allow for effective integration with the tissue (e.g., epidermis) of a subject and the ability to undergo deformation without delamination and/or failure. FIG. 43A shows deployment of the device on a subject proximate to the lateral neck, for example, for speech and/or swallow monitoring applications. FIG. 43E provides images demonstrating the capability of the device to deform without failure, for example, via stretch and twist deformation. FIG. 43D provides a series of schematics illustrating the capability of the device incorporating serpentine interconnects to accommodate stretch and twist deformations without inducing levels of strain high enough to result in significant device degradation or failure. FIG. 43C provides a schematic showing an embodiment of bidirectional wireless communication, for example, for sending an output signal from the sensor to an external device and receiving commands from an external controller to the electronic device. The schematic also shows an embodiment of power provided by wireless charging of a battery, such as a Li ion battery, for example, for providing power to a 2.4 GHz Bluetooth wireless communication component.

Figure 30A:
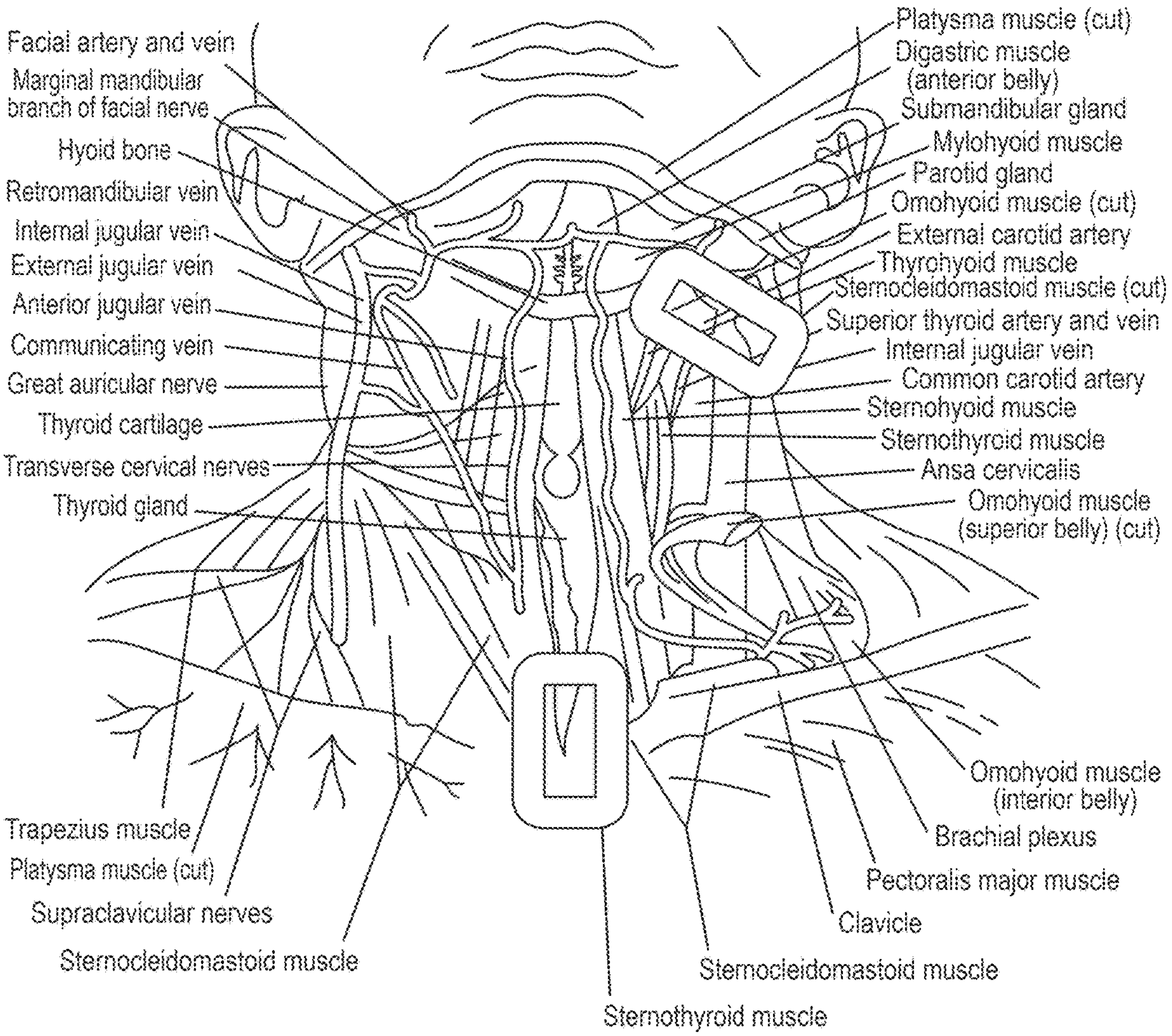
FIGS. 30A-30D.
Figure 30B:
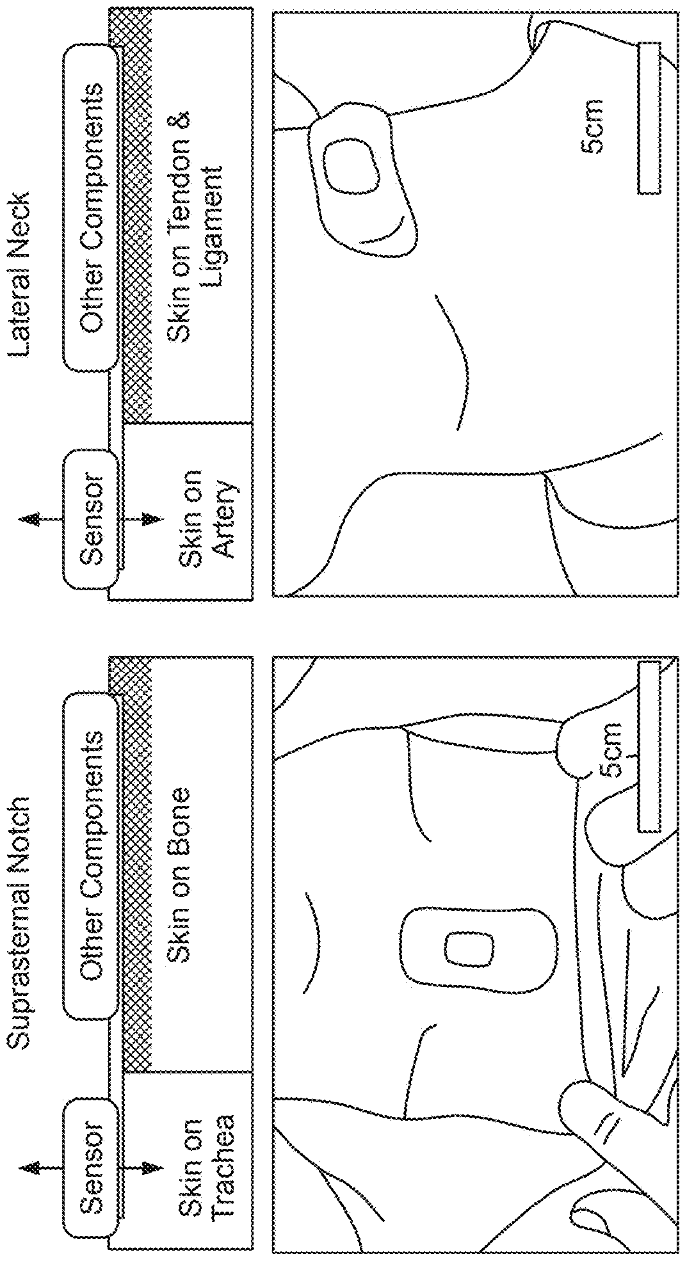
Figure 30C:
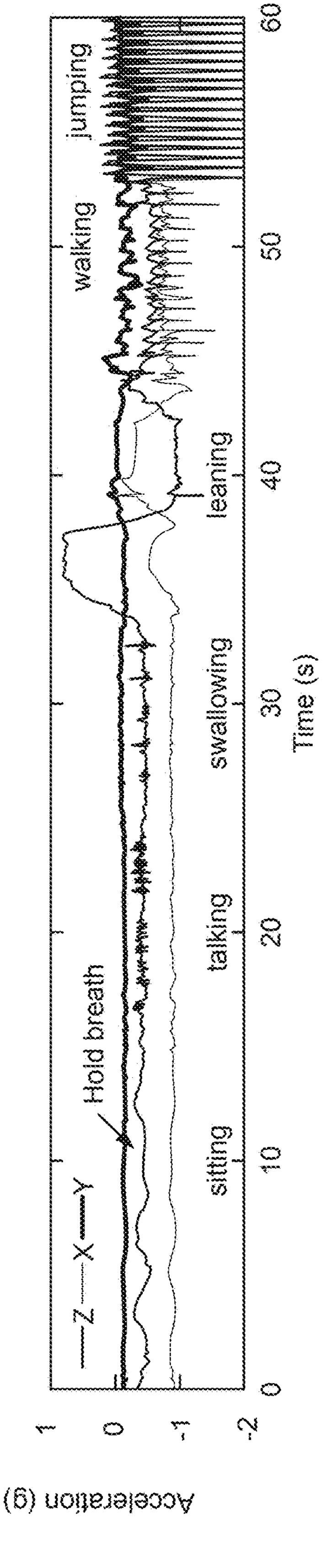
Figure 30D:
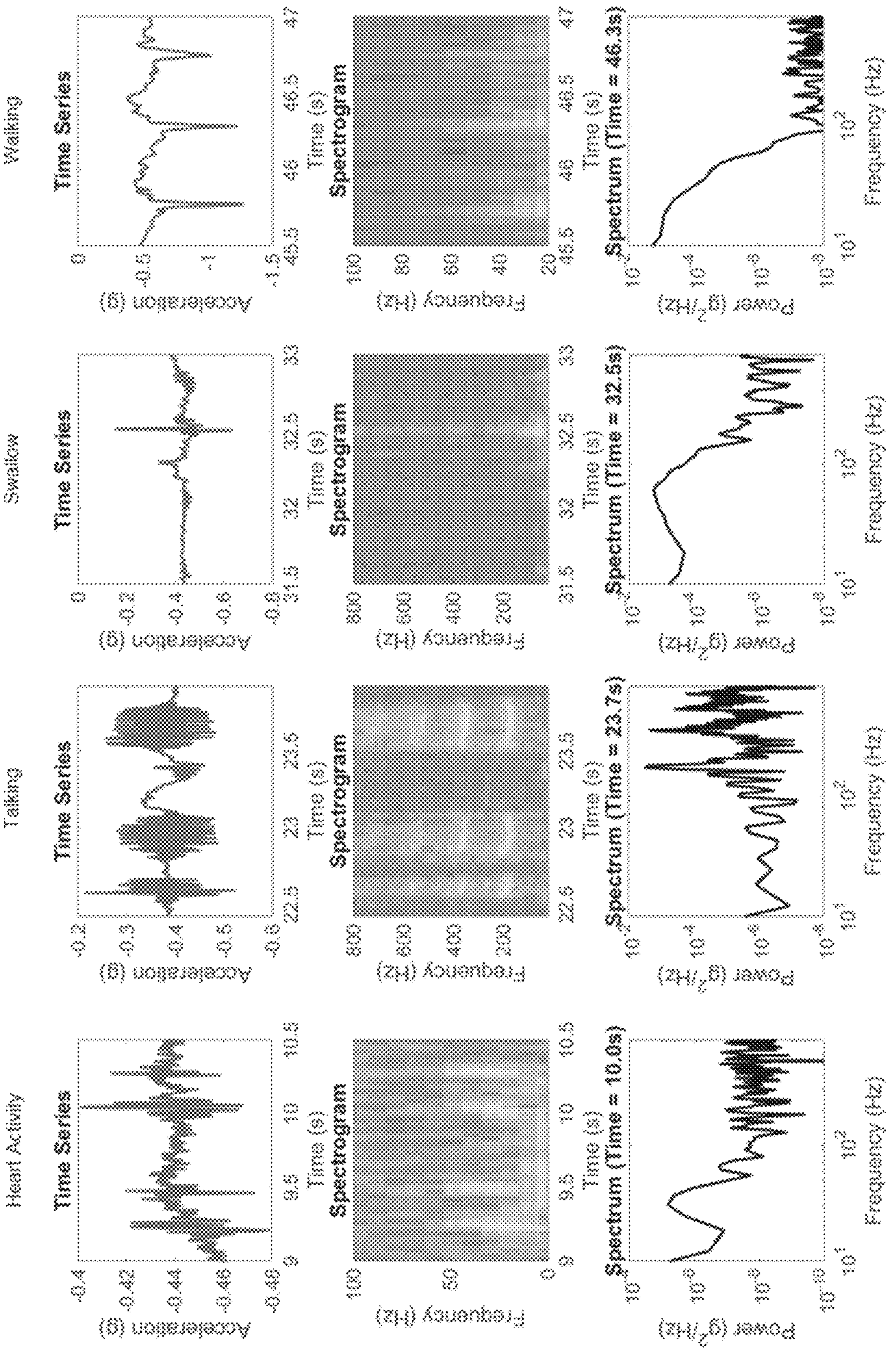

FIG. 30A provides a schematic illustrating potential mounting locations (schematically shown by superimposed boxes) on a subject. FIG. 30B provides photographs and schematics illustrating device placements on a subject including proximate to the lateral neck and proximate to the suprasternal notch. FIGS. 30C and 30D provide exemplary signals for X, Y and Z dimensions corresponding to the activity of a subject including holding breath, sitting talking, leaning, walking and jumping.

Figure 31A:
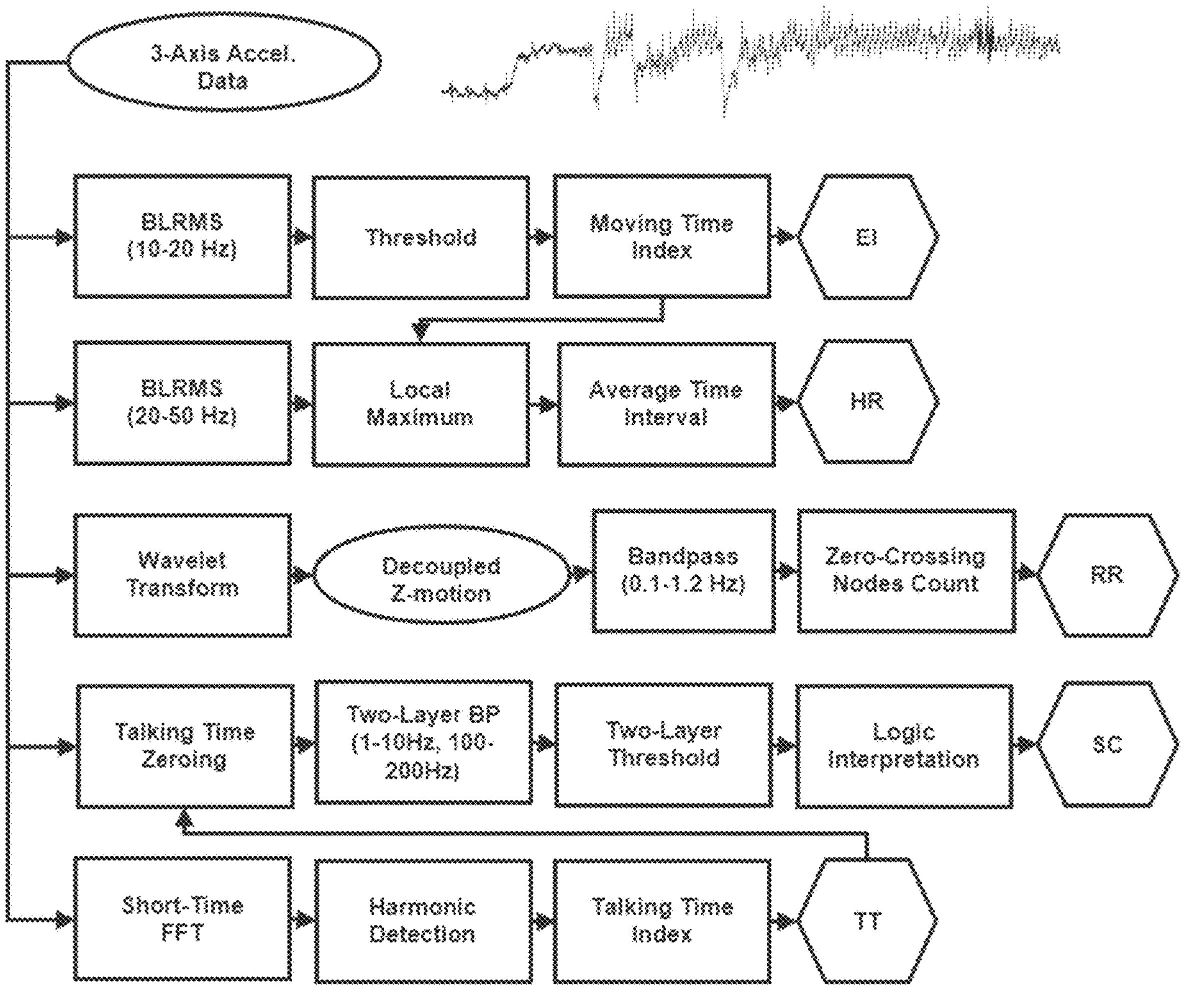
FIGS. 31A-31B.
Figure 31B:
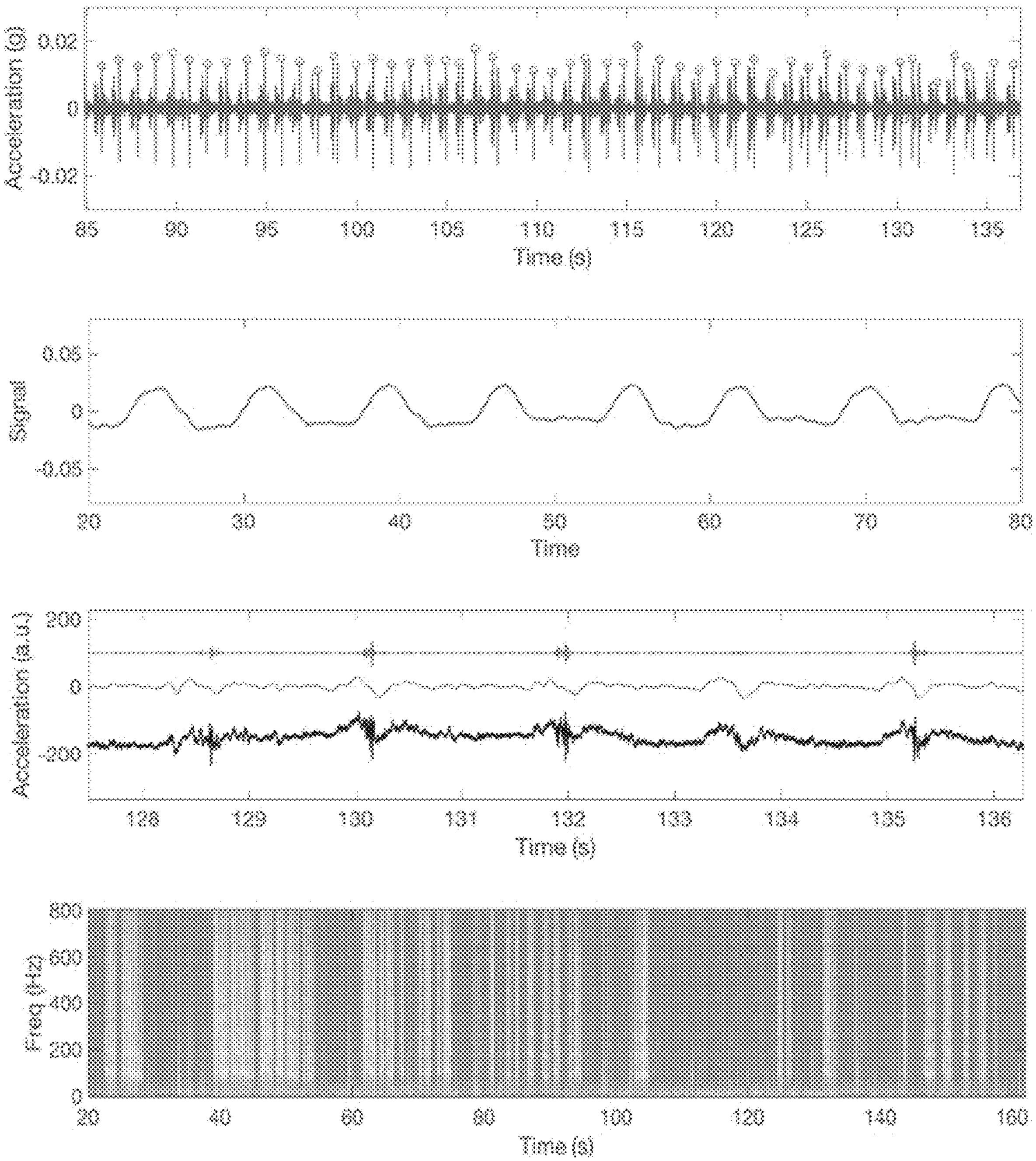

FIG. 31A provides a flow diagram corresponding to signal processing approach for the analysis of 3-axis accelerometer output. FIG. 31B provides exemplary signals corresponding to the activity of a subject.

Figure 32A:
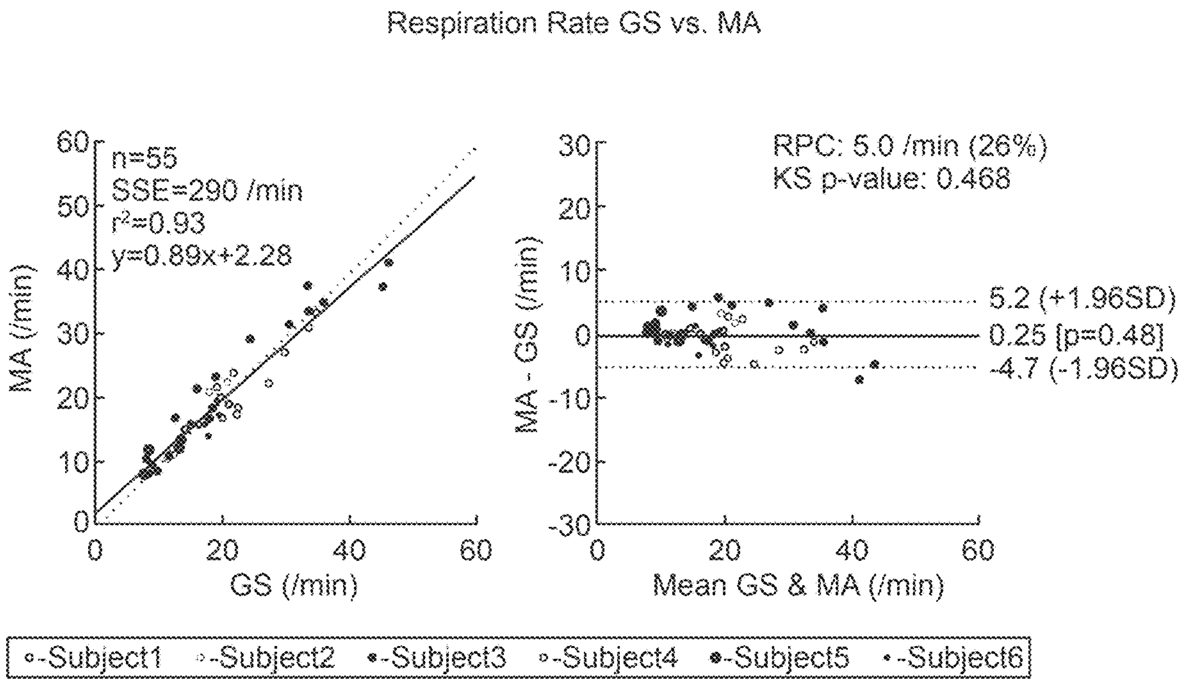
FIGS. 32A-32D.
Figure 32B:
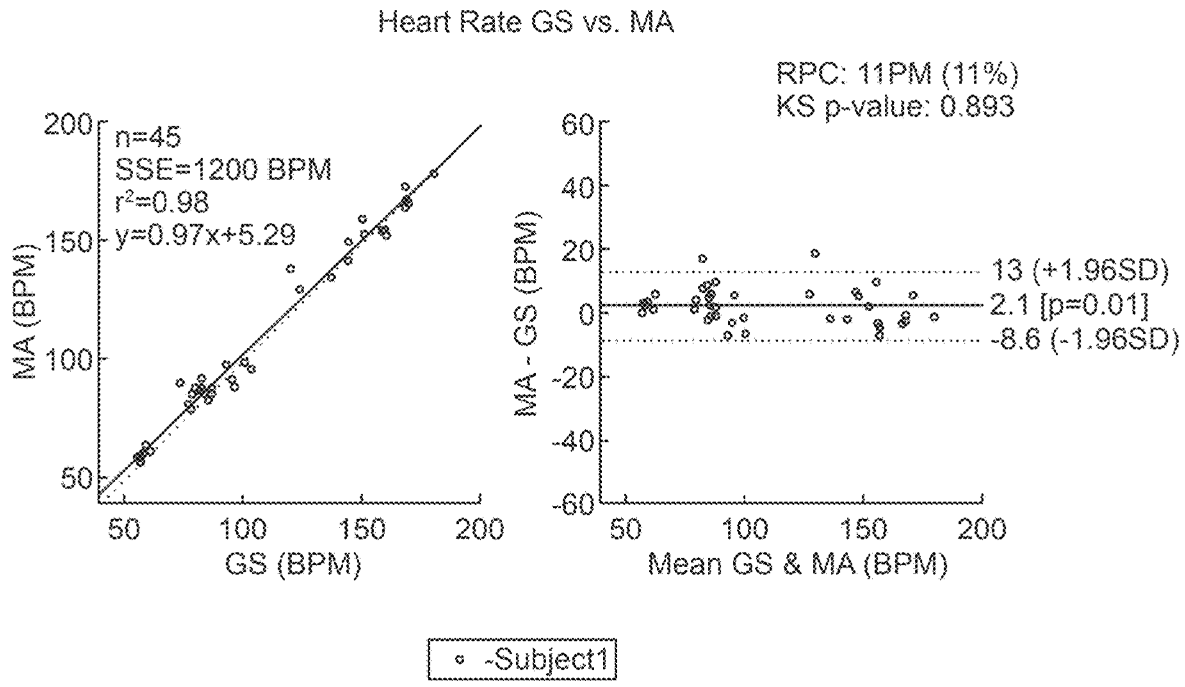
Figure 32C:
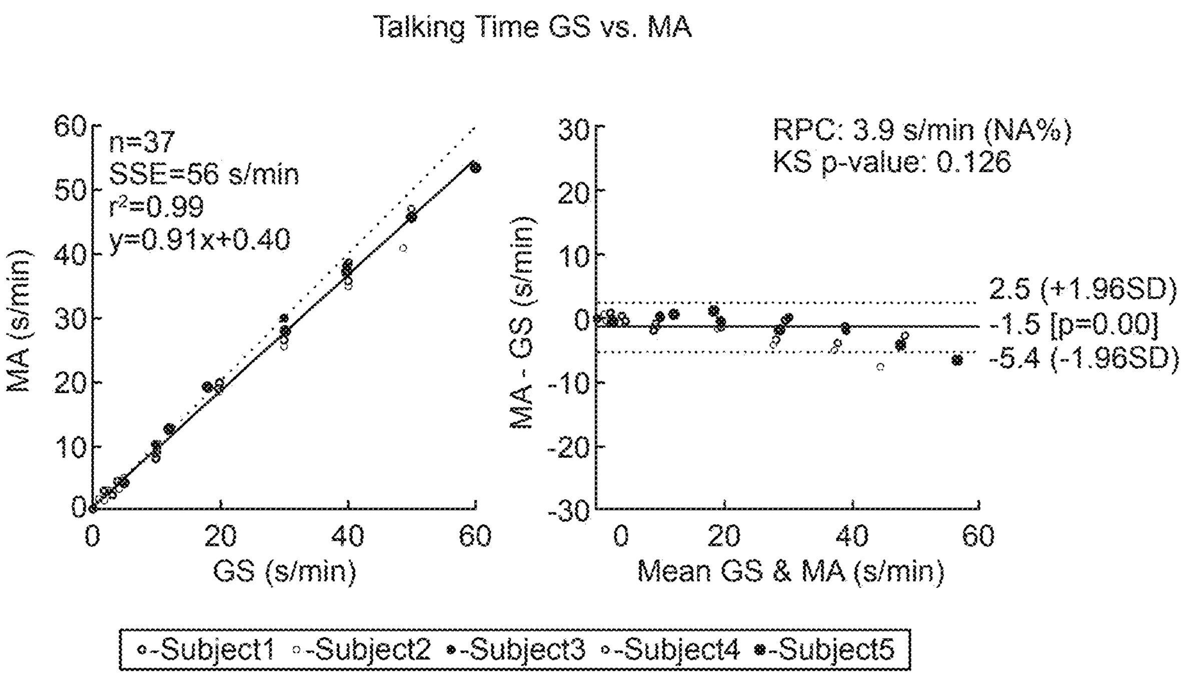
Figure 32D:
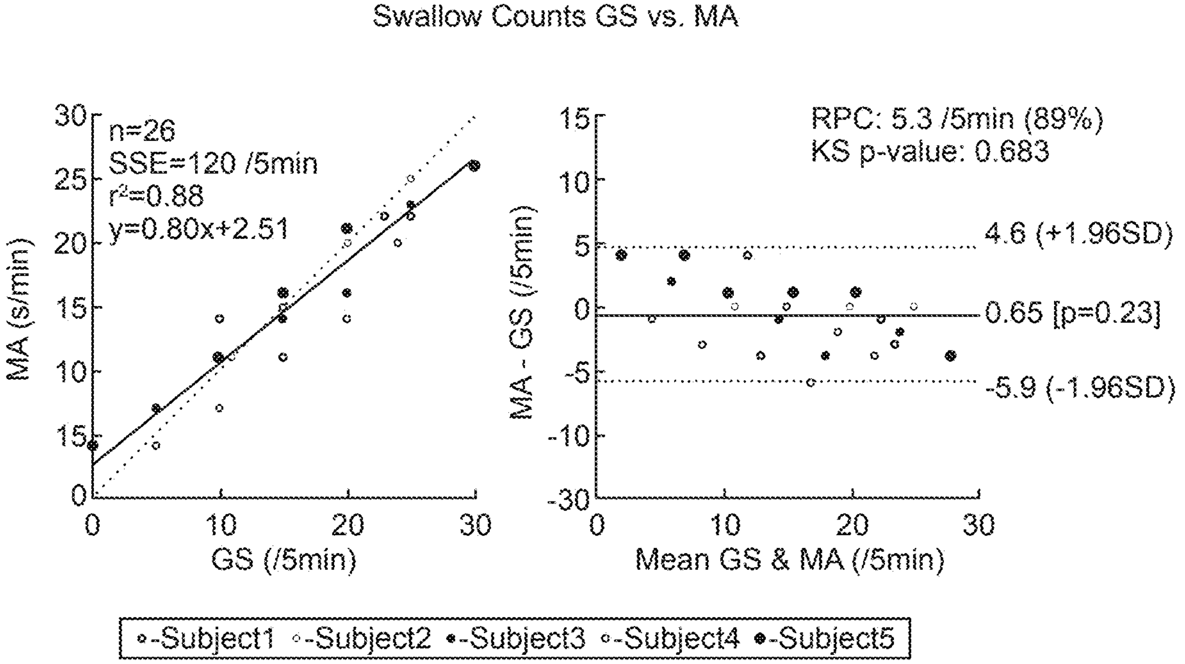

FIG. 32A provides exemplary data for respiration rate GS vs. MA corresponding to a range of subjects. FIG. 32B provides exemplary data for heart rate GS vs. MA corresponding to a subject. FIG. 32C provides exemplary data for talking time GS vs. MA corresponding to a range of subjects. FIG. 32D provides exemplary data for swallow counts GS vs. MA corresponding to a range of subjects.

Figure 33C:
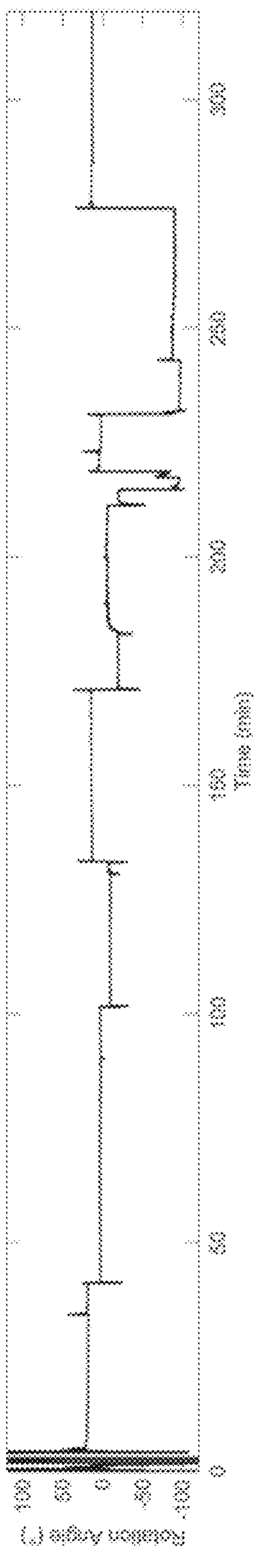
Figure 33D:
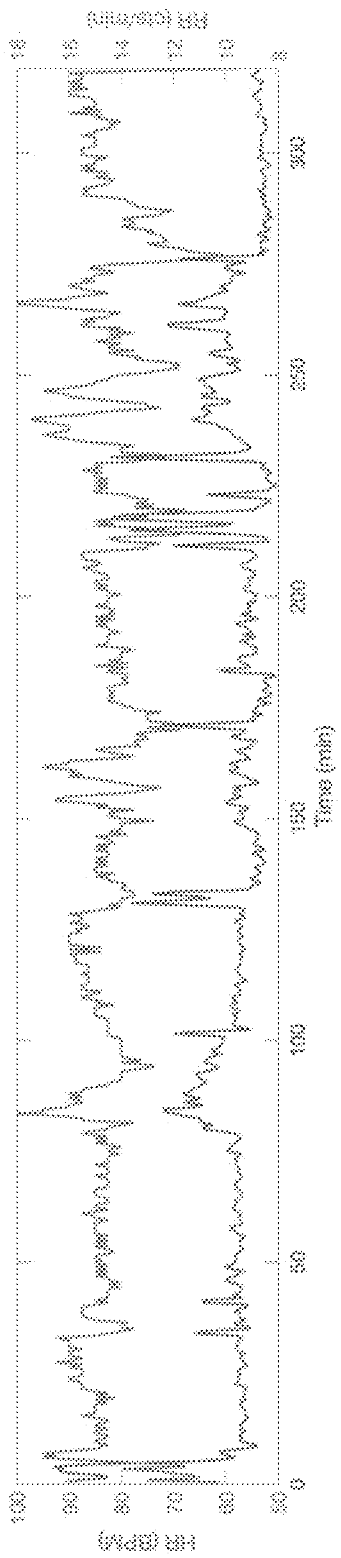

FIG. 33A and FIG. 33B provide exemplary signals corresponding to the activity of a subject including various configurations of face and head up and down movements. FIG. 33C provides a plot of rotation angle vs. time (min). FIG. 33D provides a plot of heart rate (BPM) vs. time (min).

Example 2: Wearable Sensors for Early Triage of High-Risk Neonates for CP

The present example demonstrates usefulness of flexible wearable sensor devices of the invention for diagnostic applications including early triage of high-risk neonate subjects for cerebral palsy (CP). Predicting for eventual neurological function in at-risk neonates is challenging and research demonstrates that the absence of fidgety movements are predictive of the development of CP (see, e.g., BMJ 2018:360:K207). Assessment of CP in neonate subjects is performed typically by the General Movement Assessment (GMA), for example, corresponding to a 5 min video assessment of a supine infant with a standardized rubric.

In some embodiments, networked sensors provide additional value. The ability to assess—in time synchrony through a network of on body sensors—limb movement would allow for deeper insights on abnormal movements. Analogous to sleep—this would allow for visual reproduction of movements that could provide GMA-like video data for future analysis. The advantages here include reduced data storage requirements, anonymization of the subject, and the ability to operate in low light conditions (e.g. night time or sleep).

While GMA is the current gold standard with best available evidence of positive and negative predictive value, conducting GMA requires specialized training that is not always feasible for broader screening. 3-D computer vision and motion trackers are also potentially useful for GMA, but have drawbacks of being highly expensive, requiring enormous computational power and requiring large training sets.

The present sensors provide an alternative approach capable of accurately monitoring and analyzing the movement of neonate subjects in real time and, therefore, support applications to provide clinically relevant predictive information for diagnosis of CP.

Figure 34C:
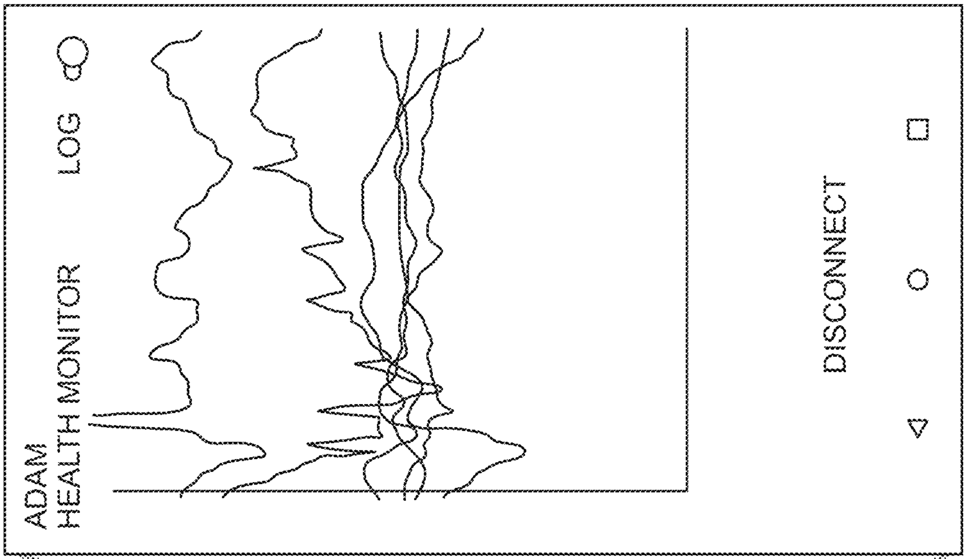
FIGS. 34A-34C.
Figure 34B:
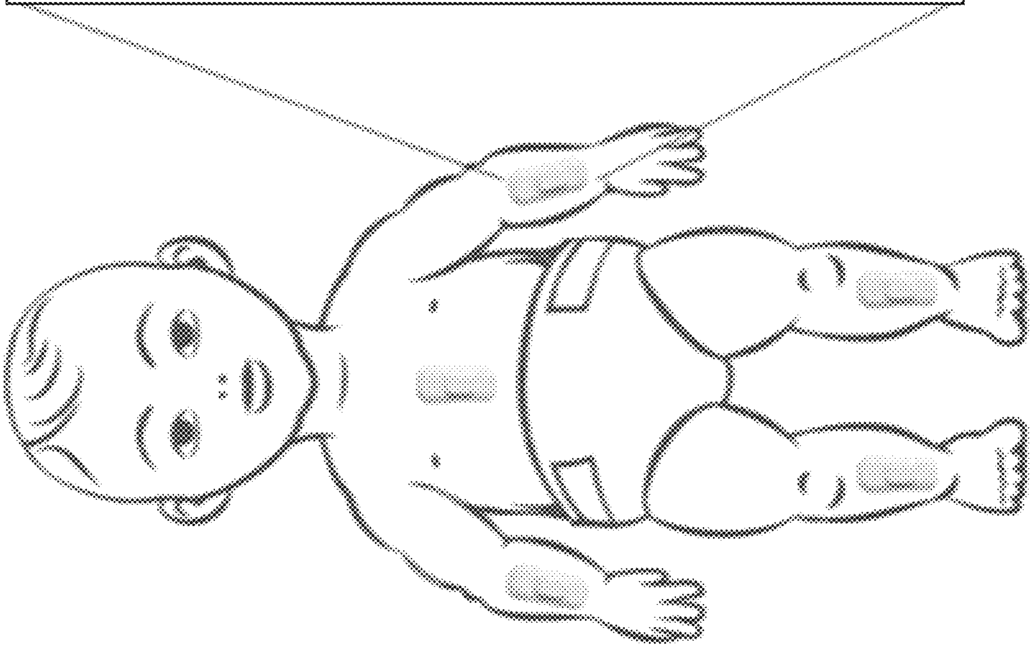
Figure 34A:
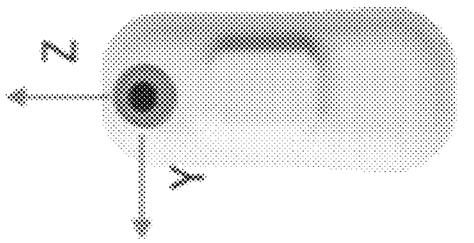

FIG. 34A provides a schematic illustrating a research-grade wearable sensor of the invention incorporating a 3-axis accelerometer, gyroscope, and EMG detector into a multilayer, flexible device format. FIG. 34B provides a schematic showing a plurality of wearable sensors (5 in total) provide on different regions for a neonate subject including the limbs and trunk. In an embodiment, the sensors are provided on the neonate subject during 1-hour clinical visits. FIG. 34C provides accelerometer and gyroscope data acquired from the sensors.

Figure 35A:
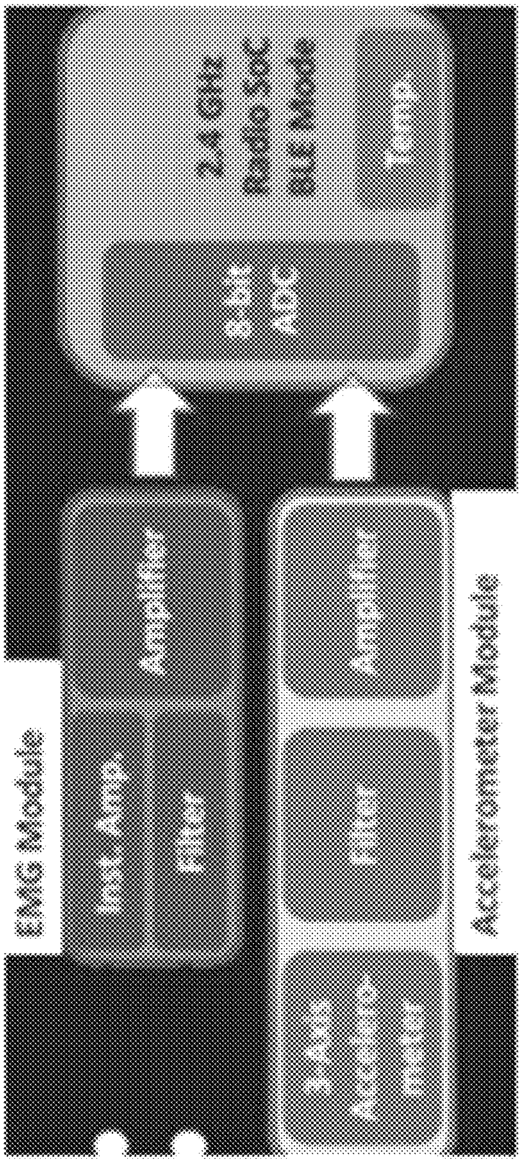
FIGS. 35A-35D.
Figure 35B:
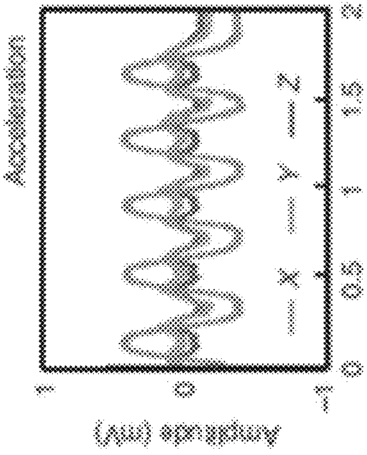
Figure 35C:
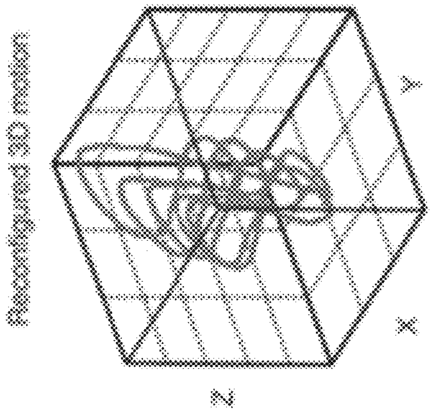
Figure 35D:
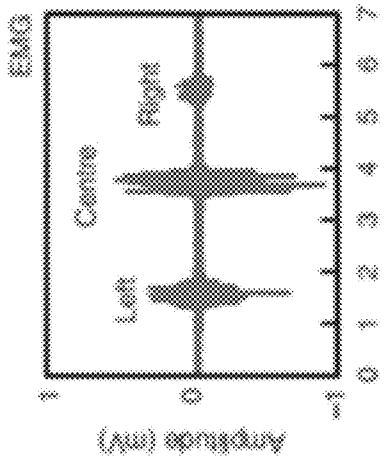

FIG. 35A provides a schematic of a sensor of this embodiment, showing EMG and accelerometer modules and Bluetooth communication module. FIG. 35B, FIG. 35C and FIG. 35D provide examples of data acquired from a sensor including acceleration, reconfigured 3D motion and EMG.

Figure 36:
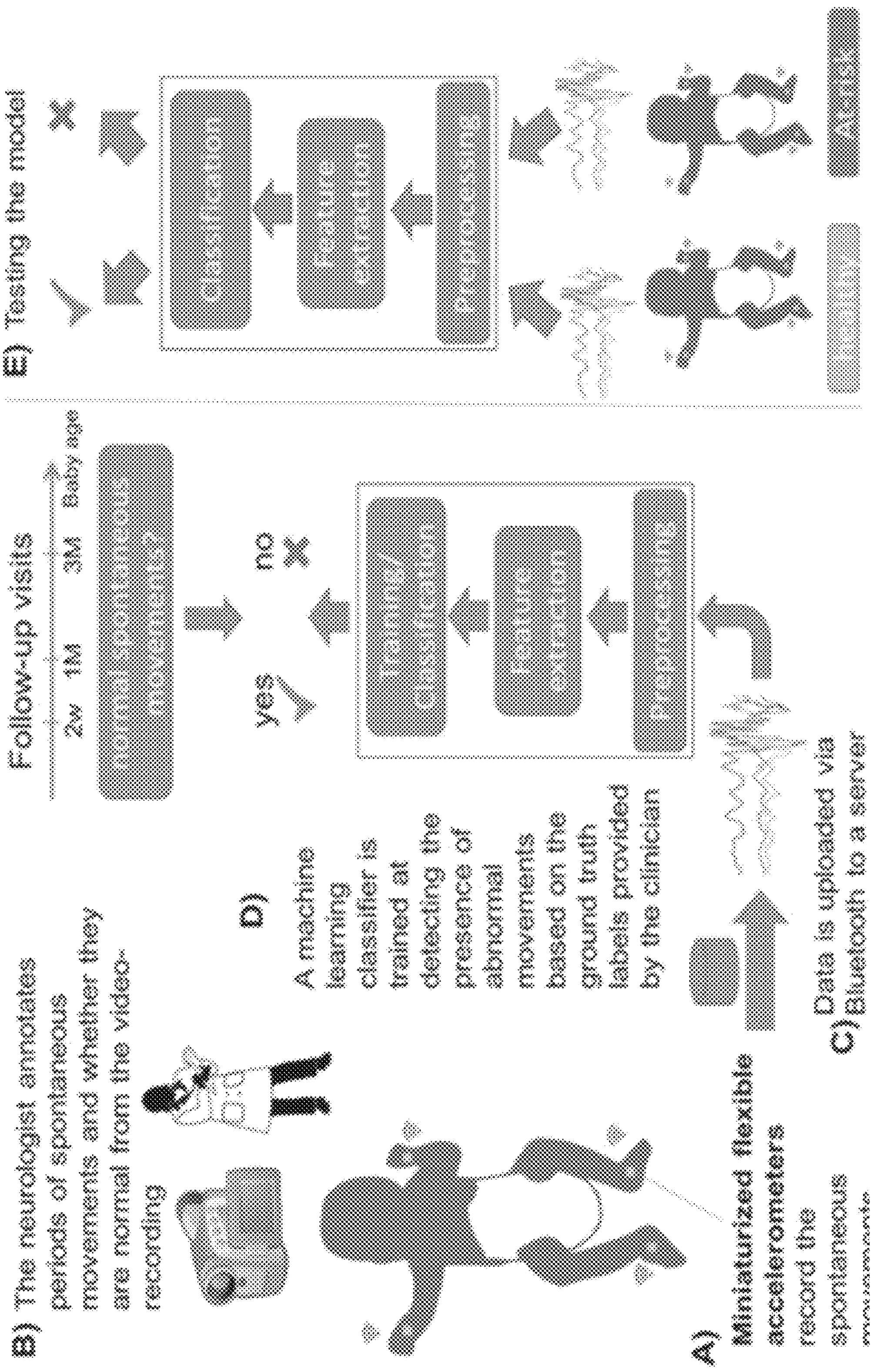
FIG. 36 provides a schematic flow diagram of methods of using sensors described herein for identifying neonate subject at risk for CP.

FIG. 36 provides a schematic flow diagram of methods of using sensors described herein for identifying neonate subject at risk for CP. As show in in the figure, the miniaturized flexible accelerometers record the spontaneous movement. The neurologist annotates periods of spontaneous movements and whether they are normal from a video recording. Data is uploaded via Bluetooth to a server and a machine learning classifier is trained at detecting the presence of abnormal movements based on the ground truth labels provided by the clinician. The model is periodically tested and updated/refined.

Figure 37:
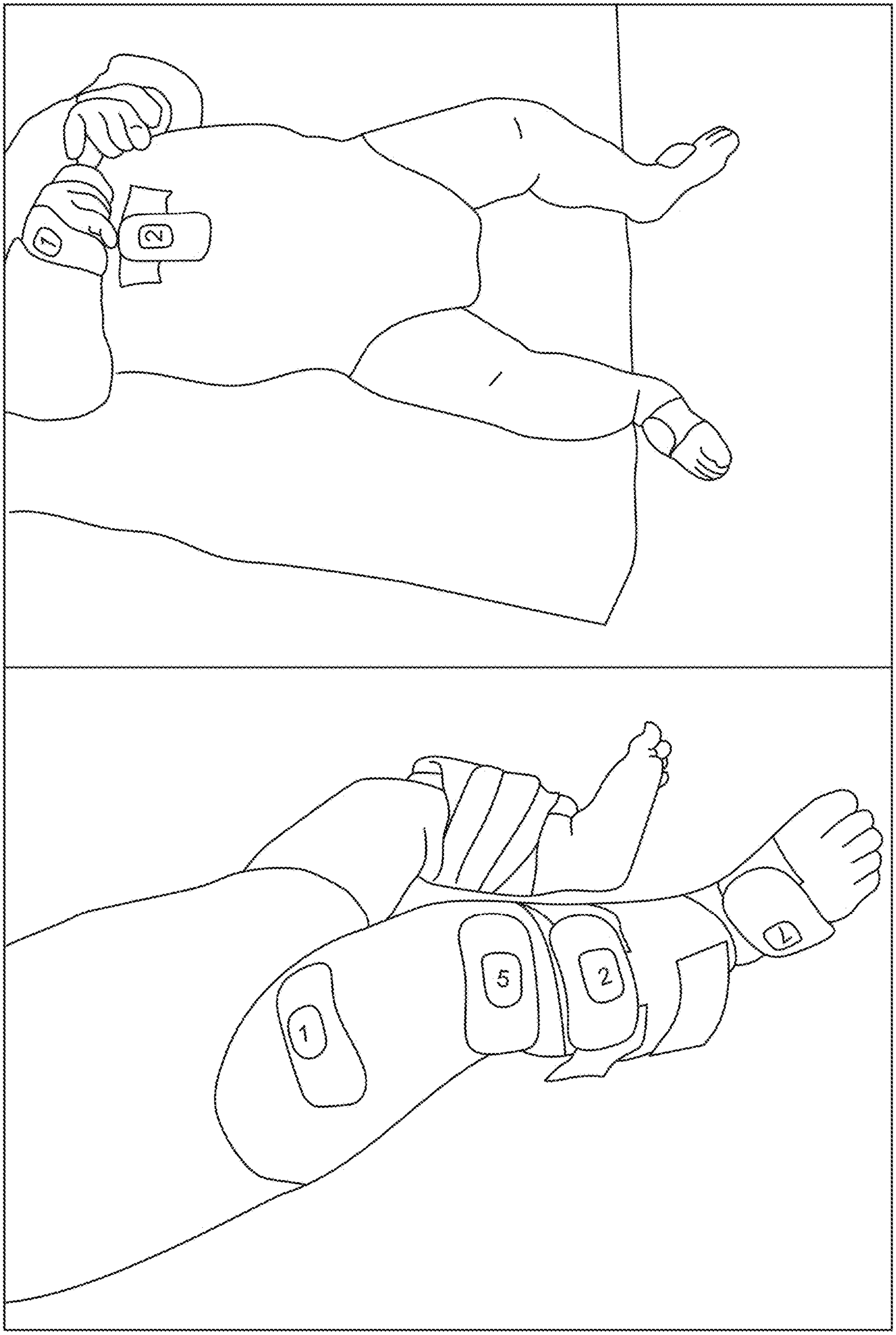
FIG. 37 provides images of miniaturized flexible accelerometers on the limbs and trunk of a neonate subject.

FIG. 37 provides images of miniaturized flexible accelerometers on the limbs and trunk of a neonate subject.

FIG. 38 provides examples of data analytics useful for analyzing the output of sensors of the present example, for example, for clinical diagnostic applications.

Figure 39:
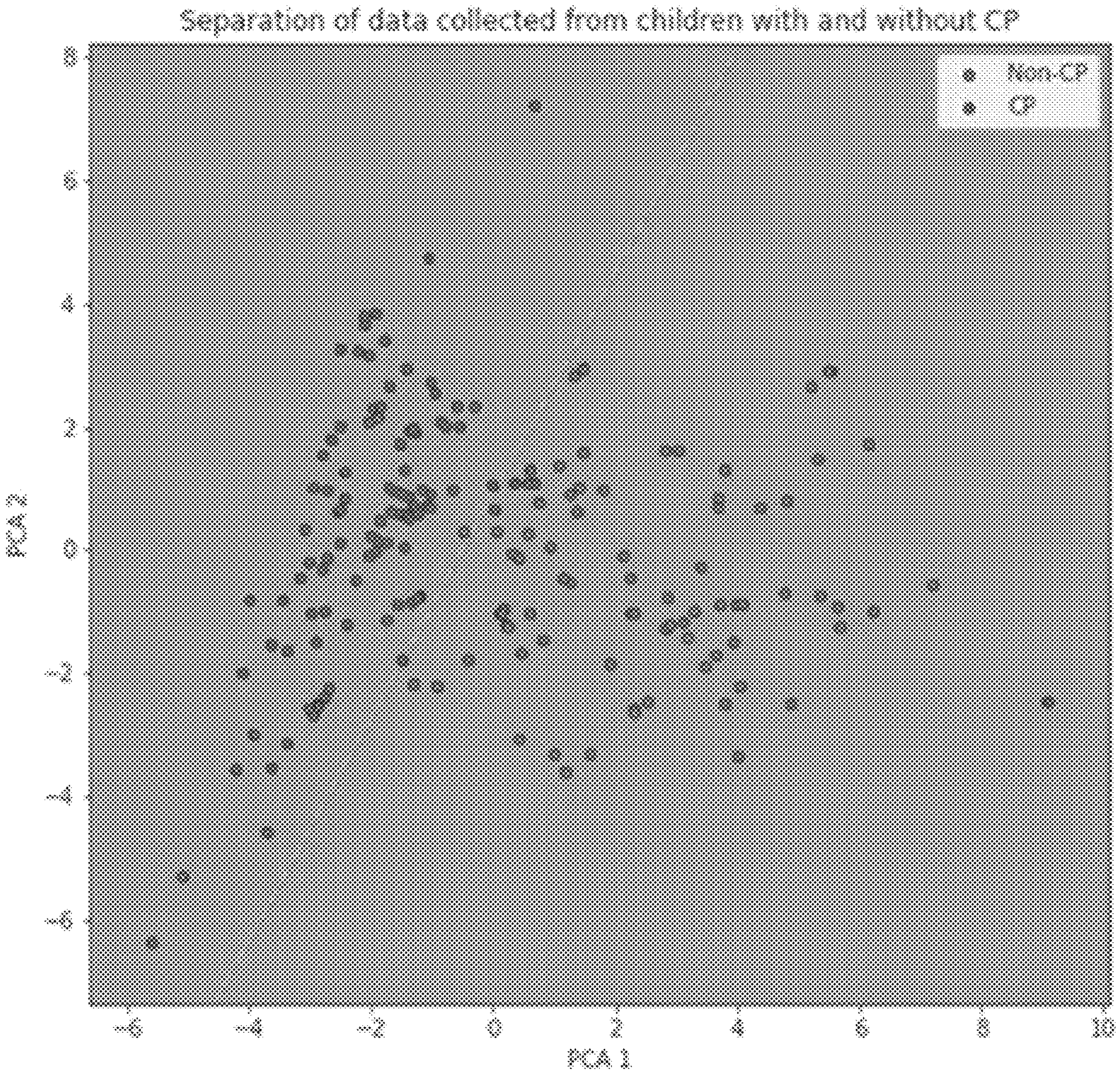
FIG. 39 provides a plot indicating differences in movement data between an infant at high risk of CP and an infant with typical development, using 20 different features extracted from movement data at 12 weeks of age.

FIG. 39 provides a plot indicating differences in movement data between an infant at high risk of CP and an infant with typical development, using 20 different features extracted from movement data at 12 weeks of age.

FIG. 40 provide results for a study of wearable sensors for children (24 months or younger) with cerebral palsy compared to age matched controls: development of a new early detection tool.

Example 3: Mechano-Acoustic Sensing

Abstract

Conventional multimodal bio-sensing demands multiple rigid sensors mounting on the multiple measuring sites at the designated place and during the reserved time. A soft, and conformal device utilizing MEMS accelerometer is a game changer to this tradition. It is suitable for use in a continuous, wearable mode of operation in recording mechano-acoustic signals originated from human physiological activities. The virtue of device, including the multiplex sensing capability, establishes new opportunity space that continuously records high fidelity signal on epidermis ranges from the subtle vibration of the skin on the order of ~$5\times10^{-3}$ $m\cdot s^{-2}$ to the large inertia amplitude of the body ~20 $m\cdot s^{-2}$, and from static gravity to audio band of 800 Hz. Minimal spatial and temporal constraints of the device that operates beyond the clinical environment would amplify the benefit of unusual mechanics of the electronics. Therefore, we develop system level, wireless flexible mechano-acoustic device to record multiple physiological information from a single location, suprasternal notch. From this unique location, the 3-axis accelerometer concurrently acquires locomotion, anatomic orientation, swallowing, respiration, cardiac activities, vocal fold vibration, and other mechano-acoustic signal that falls into bandwidth of the sensor capacity that are superposed to a single stream of data. The multiple streamlines of the algorithm parse this high density of information into meaningful physiological information. The recording continues for 48 hours. We also demonstrate the devices' capability in measuring essential vital signals (heart rate, respiration rate, energy intensity) as well as unconventional bio-markers (talking time, swallow counts, etc.) from the healthy normal in numerous field studies. We validate the results against gold standards and demonstrate clinical agreement and application in the clinical sleep studies.

INTRODUCTION

The human body continuously generates a multitude of mechano-acoustic (MA) signals that attenuate at the skin-air interface (1-5). These signals contain critical information about the physiological activity of the body, often with intensity and frequency that are beyond those associated with the audible range. They include but not limit to the vocal fold vibration (~100 Hz), cardiac activity (~10 Hz), gait (~1 Hz), respiration (~0.1 Hz), and anatomic orientation (~0 Hz). The conventional health monitoring tools are limited to the clinical environment, therefore, the mode of recording the continuous physiological activity is rather discrete. In addition, the physical condition in the clinic may have causal effect from the unnatural environment and output slanted physiological information that does not reflect the natural condition the subject (5). The long-term continuous recording of the physiological events in daily environment would provide more truthful information of the subjects. It is however challenging to have both continuous measurement and high fidelity signal recordings with the conventional electronics, such as stethoscope, or accelerometer sensor with a rigid embodiment (6). Good mechanical coupling of the conventional electronics to the skin usually breaks during the natural body movement and results distorted signal. Recent advances in flexible electronics (1, 7-11) enabled high fidelity measurement of the physiological data from the epidermis. Likewise, epidermal mechano-acoustic sensor, owing to its compliant mechanics with the low mass density, acquires high fidelity physiological information (1). This epidermal mechano-acoustic sensor utilizes accelerometer that is seamlessly coupled to the skin by the flexible substrate (1). This results in high sensitivity to the movement associated to the skin and body, but not to any ambient noise. With its soft and conformal form factor, the device does not burden skin from the mechanical mismatching and its induced stress, allowing continuous wearable mode. However, even still, wires that channel power and communication to the device degrade these advantages of mechanical isolation from the surroundings. Continuous, wearable mode of operation free from spatial and movement constraints is not possible in the wired configuration.

Near-field-communication (NFC) provides a solution with the wireless data and power transmission to wearable sensor through inductive coupling of the device antenna and transmitter antenna at 13.56 MHz (12, 13). The system has benefit of battery-free operation but persists the problem of having confined operation range that depends on the geometry and power of the antenna. Bluetooth is another wireless communication mode which allows meter scale range communication with battery (14). Thus, with maintaining the connection with portable hosting device, like cell phone, the device operates without limitation of the space. The Bluetooth platform however requires relatively larger electronic components compared to other IC, and passive components. As result, after the conventional solid elastomer encapsulation, the whole device becomes stiff.

Described herein is a wireless soft and stretchable mechano-acoustic sensing platform that provides solutions to these challenges and enables continuously monitoring of multimodal physiological information with high fidelity with Bluetooth Low Energy protocol, rechargeable Li-ion battery, and air pocket encapsulation which bypasses the effect of rigid and relatively large electronic components. The result is system level continuous diagnostic soft electronics with enhanced robustness and without spatial and temporal constraints, and as result, impervious to water or other foreign substances. Careful consideration of the measurement site provides single stream of data with rich physiological information. Suprasternal notch is the notch location in between the collarbones. As the neck is bridging circulatory and respiratory systems between the head and the torso, there is presence of signals with various intensity and frequency that are coupled to those physiological systems. With the consideration of specific feature of each signals and associated events, the algorithm parses out the single data into multiple physiological information.

Results

Device Design and Circuit Considerations

The ultrathin, soft form factor of the wireless mechano-acoustic sensor enables measurement of mechanical signals from suprasternal notch with high signal fidelity. FIG. 43A highlights the conformal construction of the device with ability to deform naturally with large movement of the neck. The design incorporates stretchable and flexible interconnects, strain isolation layer, and soft encapsulation to accommodate the large mechanical deformation of the circuit featuring wireless communication and powering with robustness.

FIG. 43B presents the overall structure of the system. The electronic platform is a flexible PCB (fPCB) composed of double-sided copper with polyimide as the insulation layers sandwiching the copper layer. The fPCB utilizes rolled annealed copper that has 6.5 times longer endurance limit than the conventional electrodeposited copper films (16).

We engineer the electronics around three major components for MA signal acquisition and wireless operation: three-axis digital accelerometer (BMI160, Bosch) measuring vibration at sampling frequency of 1600 Hz with a broad range (+/−2 g), high resolution (16 bit), a microcontroller (nRF52832, Nordic Semiconductor) acquiring data and communicating wirelessly with the user interface via Bluetooth Low Energy (BLE), and a wireless charging circuit replenishing a 45 mAh lithium-ion battery inductively (FIG. 43E). The BLE communication protocol operates over the distance range of ~2 m.

Figure 48:
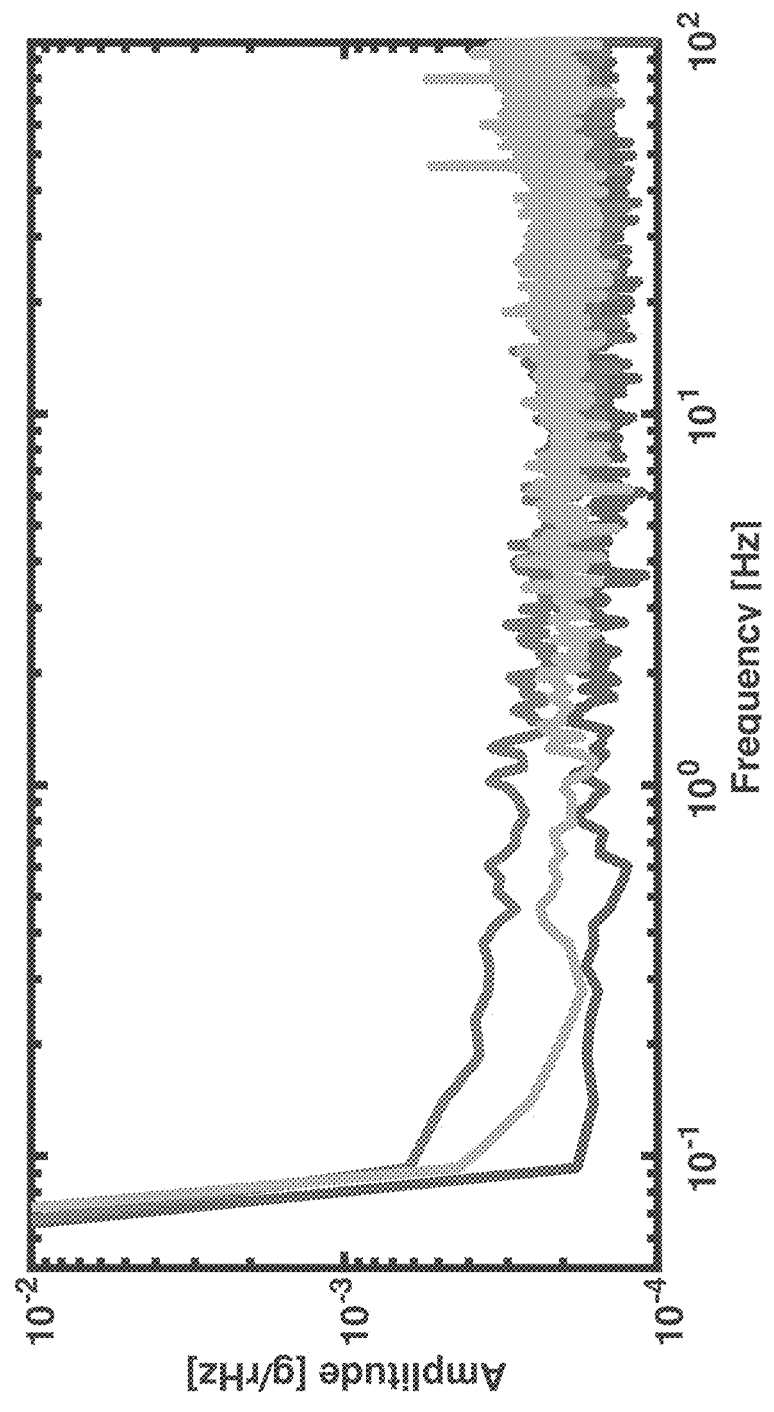
FIG. 48 provides an example wavelet cross spectrum analysis.
Figure 49A:
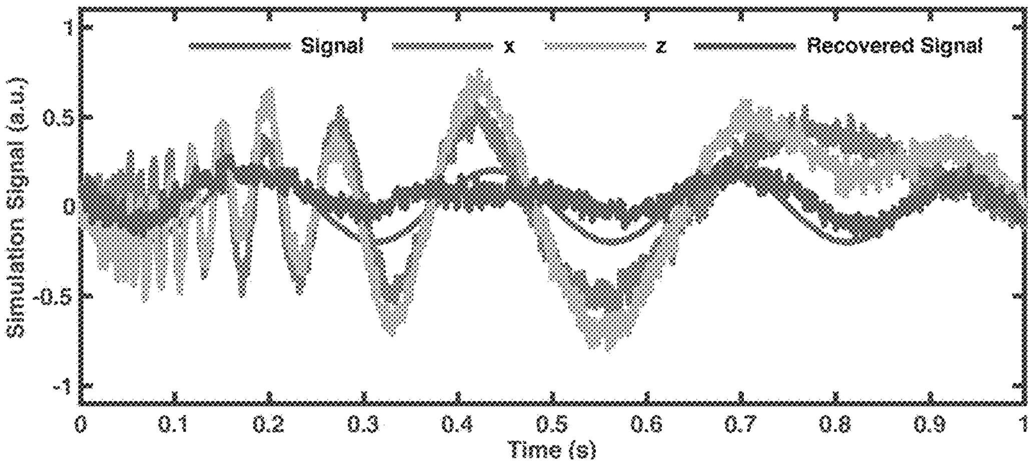
FIGS. 49A-49B.
Figure 49B:
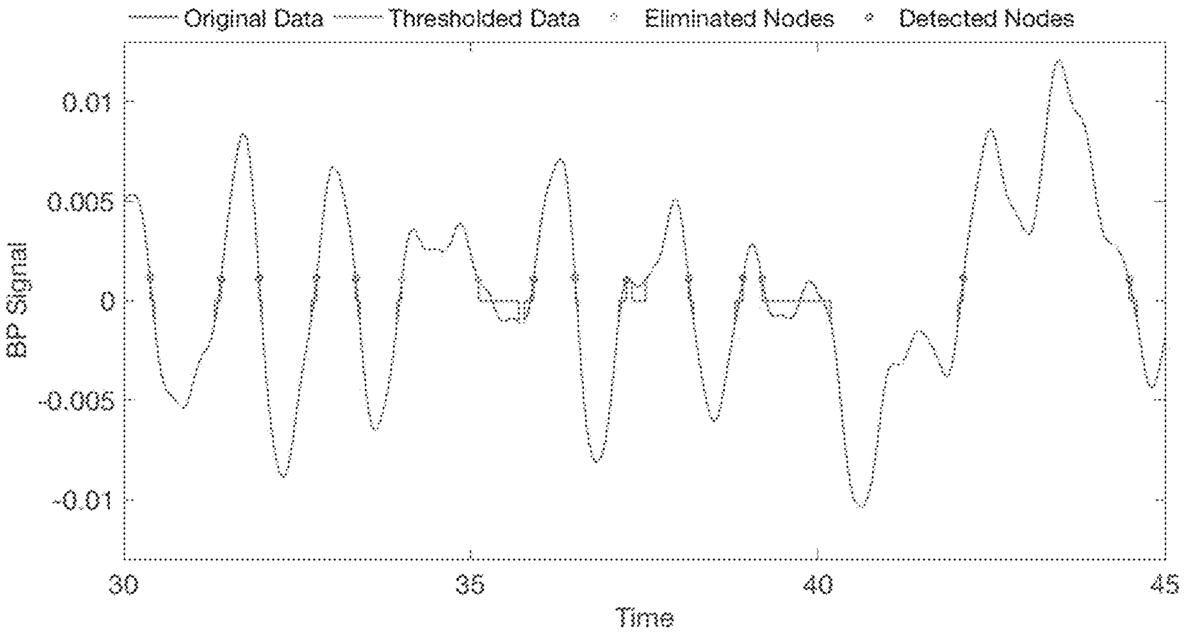
Figure 55A:
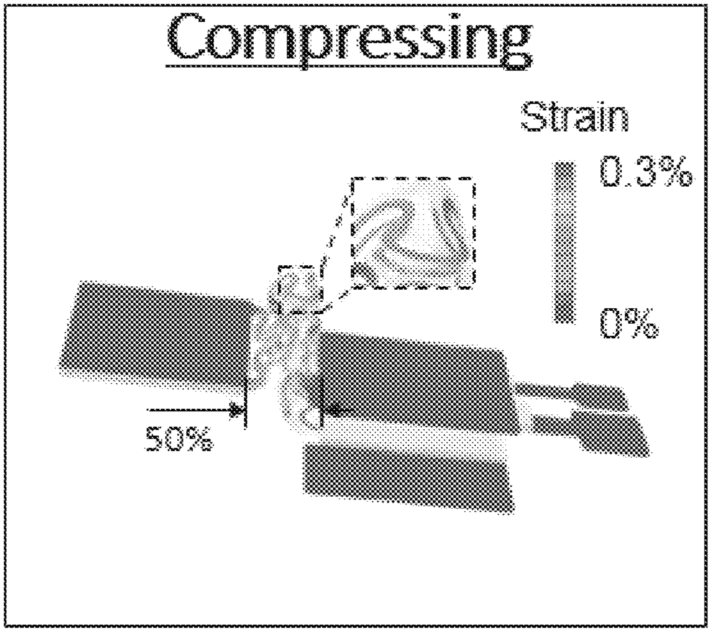
FIGS. 55A-55B. Simulation of system level device deformation.
Figure 55B:
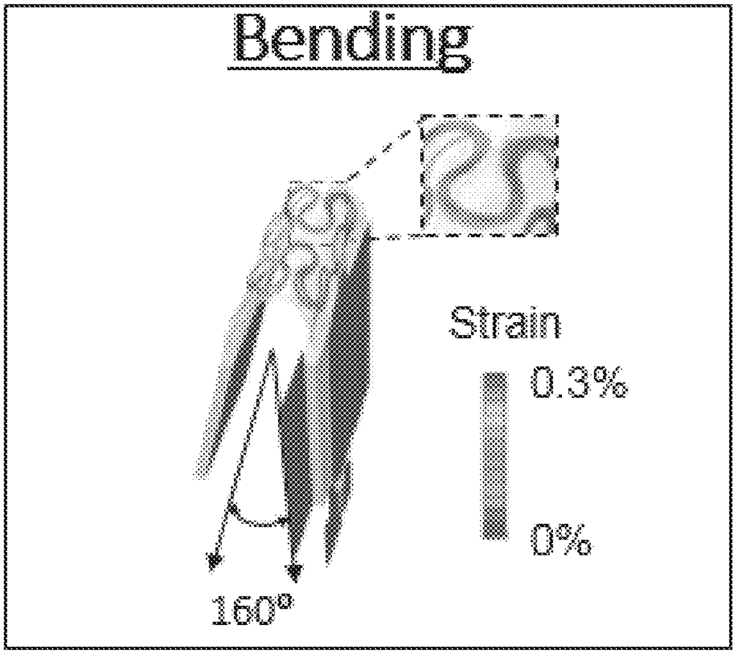

The employment of the off-the-shelf IC components and battery provides benefit of robustness and production yield, but their rigid and bulky construction can suppress overall compliance of the device. To resolve this issue, we apply serpentine shaped interconnects to mechanically decouple the small flexible PCB island (1 cm×1 cm) that is densely populated with electronic components associated with the microcontroller and charging circuit as shown in the FIG. 43B. With this dense allocation of the IC components, the sensor reserves 71% of the overall area for the flexible interconnects and edged of the device for deformation absorption. The interconnects are compressed by 10% of its original length at the inactive state (FIG. 43C). The pre-buckled structure increases the deformation capacity of the device by neutralizing the initial 10% tensile elongation (FIG. 48). The simulated results show that the pre-buckled serpentine structure with 270° arc angle recovers 42% tensile strain, which is 40% higher than the previously reported designs (12), and twist with 90° torsion angle (FIG. 43D). From simulation, the device can also undergo 40% compression, and 160° bending before yielding (FIG. 55).

Figure 56:
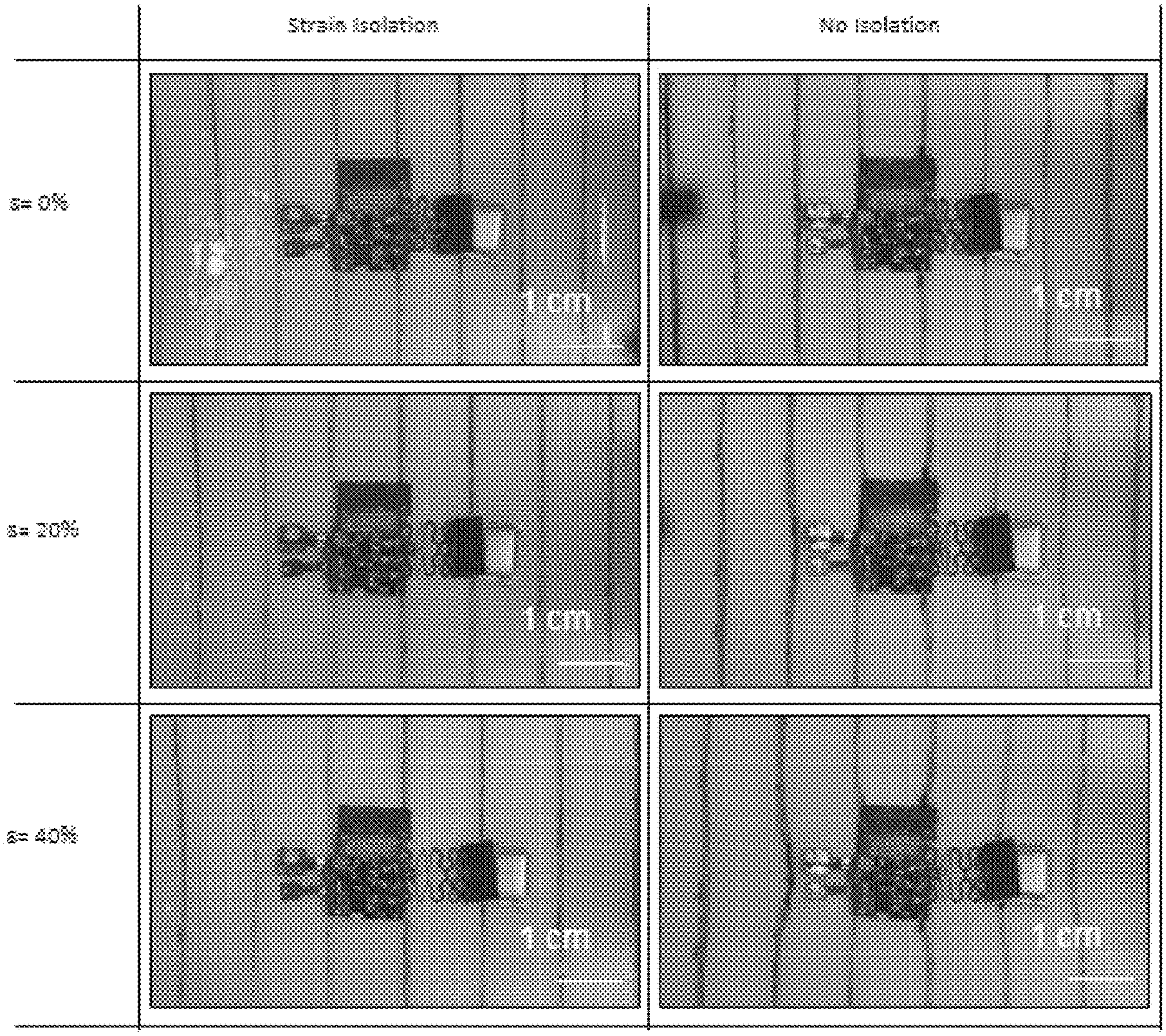

We apply a 0.4 mm thick viscoelastic silicone gel with ultralow modulus of 6 kPa underneath the flexible PCB for strain isolation. The isolation layer decouples the stiff electronics island other than the accelerometer from large in-plane deformation of the substrate up to 40% strain (FIG. 56). FIG. 56 shows relation between strain isolation with the various thickness of gel and stress on skin.

The wireless device is encapsulated by a silicone elastomeric membrane for its use in daily activity. The device, as result, is impervious to water or other foreign substances. The thin (300 mm) membrane, made of silicone (Ecoflex Smooth-on) with low modulus of 60 kPa and high resilience of 500 MPa, encapsulate the electronics without making physical contact with them (See SI for details). The design aims to minimize the stiffening effect from the encapsulation. The thin membrane encapsulation with hollow core has low moment of inertia of 68 $mm^3$ as compared to the solid silicone encapsulation of 450 $mm^3$. It offers extra robustness of the electronics from the absence of mechanical interaction between the electronic component and the encapsulation materials. The hollow core also allows serpentine interconnects to deform in a free-standing fashion, giving rise to additional stretchability as compared to serpentines restricted to in-plane deformation. The low mass density of the device and highly sensitive accelerometer also benefits from the hollow encapsulation. With the mechanics and materials engineering mentioned above, the device is mechanically robust and functioning even with the large deformation as demonstrated in the FIG. 43E.

In-Field Bio-Signal Measurements

Figure 44A:
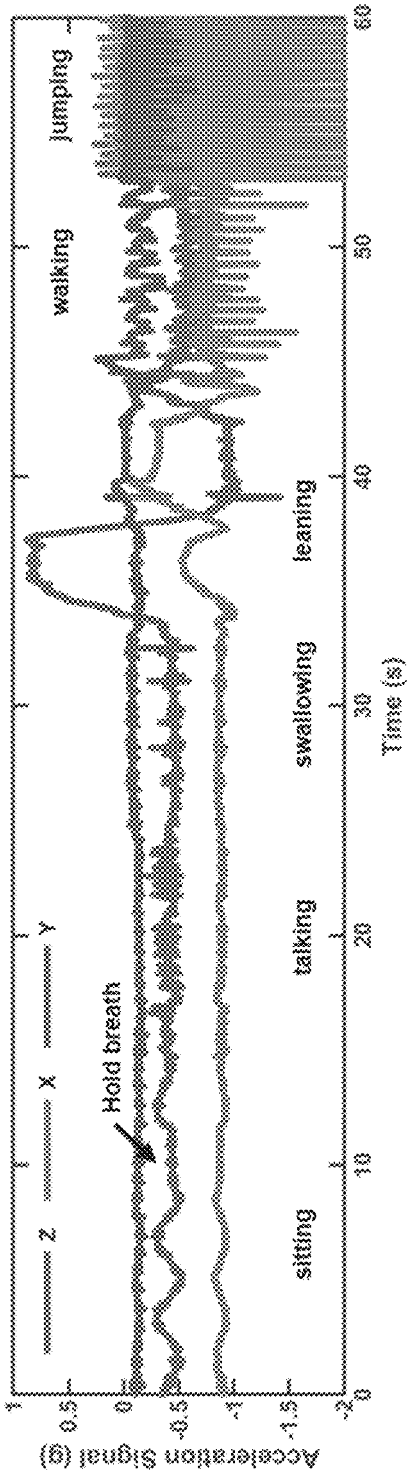
FIGS. 44A-44B. Sample three-axis accelerometer data acquired from a single MA device mounted on the neck of a healthy normal subject.

The soft, conformal and untethered contact of the device with the epidermis allows measurement from subtle vibration of the skin on the order of $\sim 5\times 10^{-4}$ $g/\sqrt{Hz}$ (FIG. 48) to the large inertia amplitude of the body ~2 g from low to high frequency (0-800 Hz), where g=9.8 $m/s^2$ is the gravitational acceleration. When mounted on the suprasternal notch which bridges the circulatory and respiratory system between the head and the torso, a single device simultaneously captures gravity as well as mechanical motions and acoustic vibrations arising from the subject's core-body motion, heart murmurs, respiration, speech, and swallowing. FIG. 44A presents sample 60-s three-axis acceleration data acquired from a healthy normal subject demonstrating a series of bioactivities including sitting, talking, drinking water, body leaning, walking, and jumping.

Figure 44B:
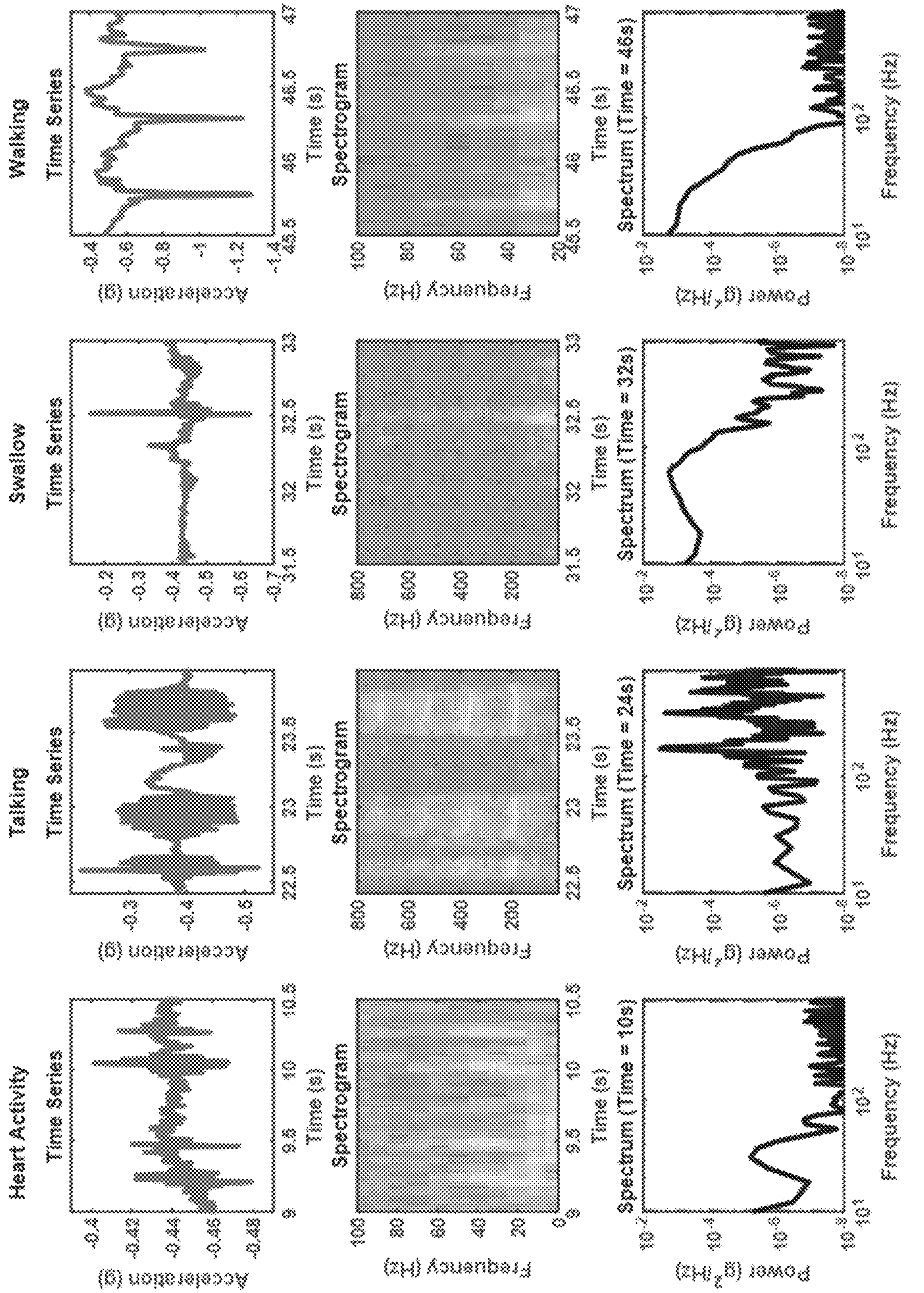

The acceleration signals originated from different physiology exhibit distinct features in both time and frequency domain and convey rich set of information about the associated bioactivities. We focus on z-axis acceleration data which emphasizes motions and vibrations normal to the surface of the skin. Breathing activities, manifested as low-frequency chest wall motion, induce changes in the magnitude of gravity projection on the all axes. The subject held breathing at about 10 second mark, yielding a plateau in the acceleration signal. The quasistatic 3-dimensional accelerations provide gravity vector measurement that indicates body orientation. FIG. 44B shows detailed characteristics of the individual physiological events. The top row, middle row, and bottom row each presents zoomed-in time series, time-frequency spectrogram, and a sample spectrum of representative high-frequency (>10 Hz) events. The frequency analysis applies Hanning window of 0.1 s with 0.98-s overlap. Cardiac activities—the systolic and diastolic (6)—give rise to paired pulse with peak amplitudes of ~0.05 g, and a power concentrated in band 20-50 Hz. The speech signals feature high-quality harmonics of fundamental frequencies in the range from 85 to 255 Hz for typical adults. Swallow events initiate with slow (~0.1 s) vocal folds and larynx mechanics during pharyngeal phase and end with high-frequency ring-down of water during esophageal stage [ref.]. The walking or jumping motions induce large amplitude (~1 g) impact force that spans broad frequency range up to ~100 Hz.

Figure 45A:
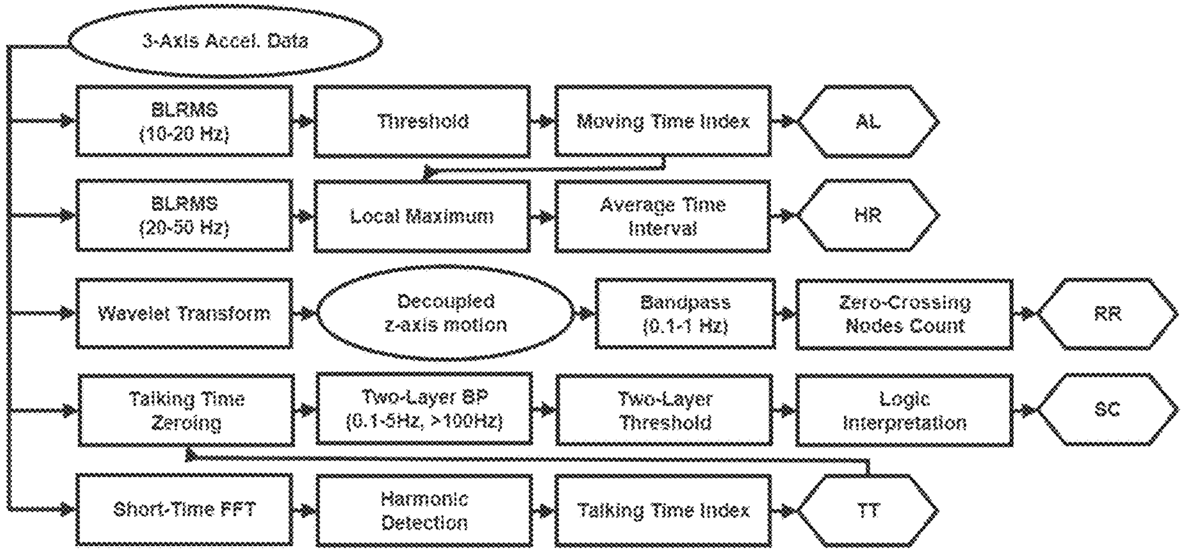
FIGS. 45A-45E. Signal processing of MA data acquired from healthy normal field study.

The single-device MA measurements stream superposed information from multiple signal sources. We set up an offline data processing flow utilizing the characteristic features as demonstrated in FIG. 44 to extract biomarkers that can play crucial roles in clinical and healthcare applications, i.e. energy expenditure (EE), heart rate (HR), respiration rate (RR), swallow counts (SC), and talking time (TT) (FIG. 45A).

For all filtering process, we use the 4th order Butterworth infinite impulse response (IIR) discrete-time filter followed by a non-causal, zero phase filtering approach. We estimate EE in 2-s, 50% overlapping time window as a sum of all-axis low-frequency (1-10 Hz) band-limited root-mean square (BLRMS) [Liu2011]. We classify routinely active versus in-active states using a threshold of 0.05 $g^2=\bar{s}+5\delta s$, where $\bar{s}$~0.012 g, δs~0.008 g are characteristic mean and standard deviation of the EE measurements for the subject.

Figure 45B:
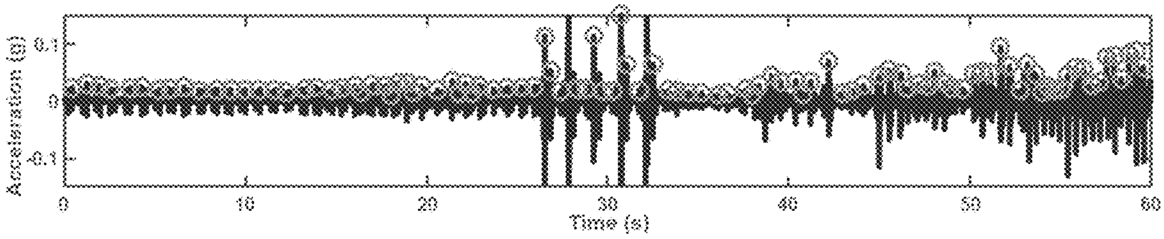

Heart rate analysis starts with passing the z-axis acceleration data through a bandpass filter ($f_1$=20 Hz, $f_2$=50 Hz) to suppress noise outside the frequency range of interest. We zero signals in time windows with excessive motions detected (EE>0.05 $g^2$) and identify cardiac pulses as local maxima in the time series of band-passed signal, given a minimum peak height of 0.005 g and a minimum peak distance of 0.33 s (~180 BPM) (FIG. 45B). The algorithm rules out peak intervals that are longer than 1.2 s (~50 BPM). Applying with 5-s time window averages on peak-to-peak intervals gives the running HR estimation.

Figure 45C:
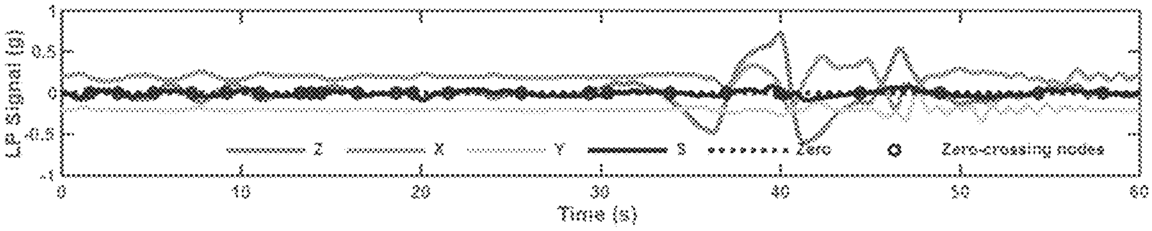

Respiration measurement is sensitive to the motion artifact owing to the overlap in their frequency domain (0.1-1 Hz). We develop a noise subtraction algorithm utilizing the time-synchronized three-axis acceleration measurements—given the unique device mounting location and orientation (FIGS. 43A-43B), z-axis and x-axis measurements are both sensitive to chest-wall motion, while y-axis acceleration is associated mainly to core-body motions. We apply the continuous wavelet transform and cross-wavelet transform to extract common mode $s_{xz}$ between z- and x-axis measurements and then differential mode $s_{(xz)y}$, between $s_{xz}$ and y-axis measurements (Note S1). The number of zero-crossing nodes of band-passed ($f_1$=0.1 Hz, $f_2$=1 Hz) signal, N, counts the number of inspiration and expiration in 1 min and estimates RR as N/2 breathe per minute (BPM) (FIG. 45C, See SI for details).

Figure 45D:
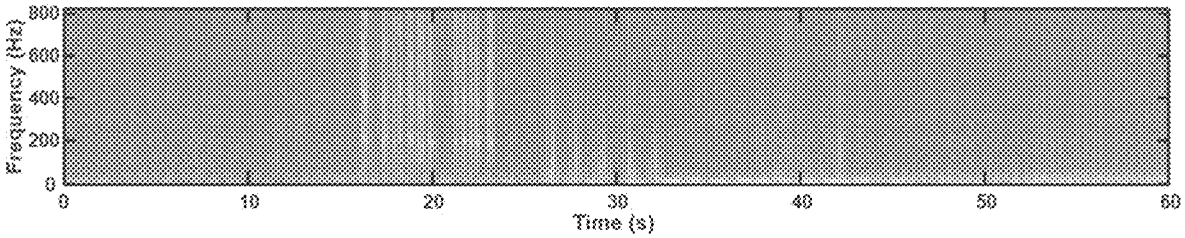
Figure 45E:
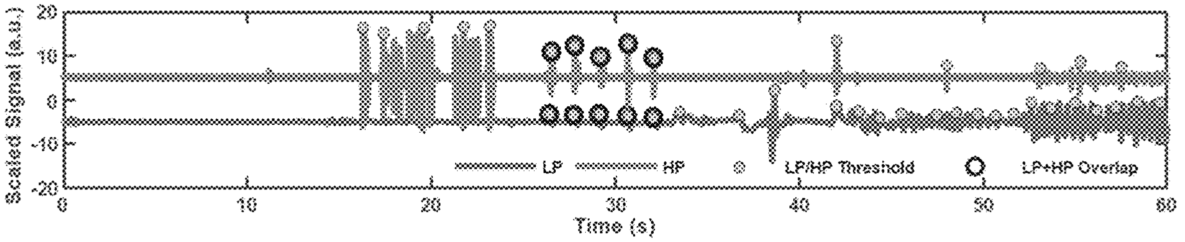
Figure 46A:
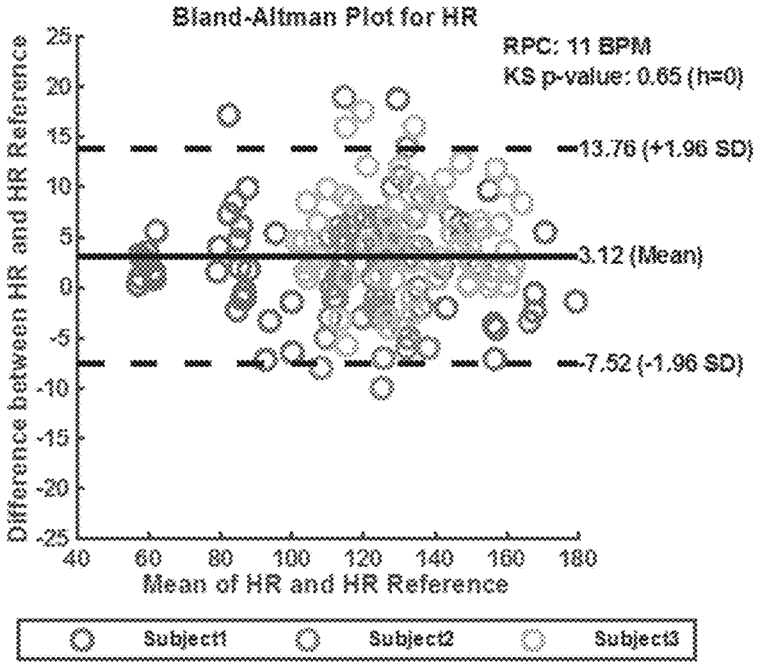
FIGS. 46A-46D. Bland Altman analysis for (FIG. 46A) HR, (FIG. 46B) RR, (FIG. 46C) TT and (FIG. 46D) SC. The solid and dashed lines represent mean difference and standard deviation×1.96, respectively. HR has a mean difference of −3.12 bpm and a standard deviation of 5.43 bpm. RR has a mean difference of 0.25 breathes per minute and standard deviation of 2.53. TT has a mean difference of −2.00 s/min and a standard deviation of 2.17 s/min. SC has a mean difference of −0.65 counts per 10 counts and a standard deviation of 2.68 counts per 10 counts. Different colors represent different healthy normal subjects.
Figure 46B:
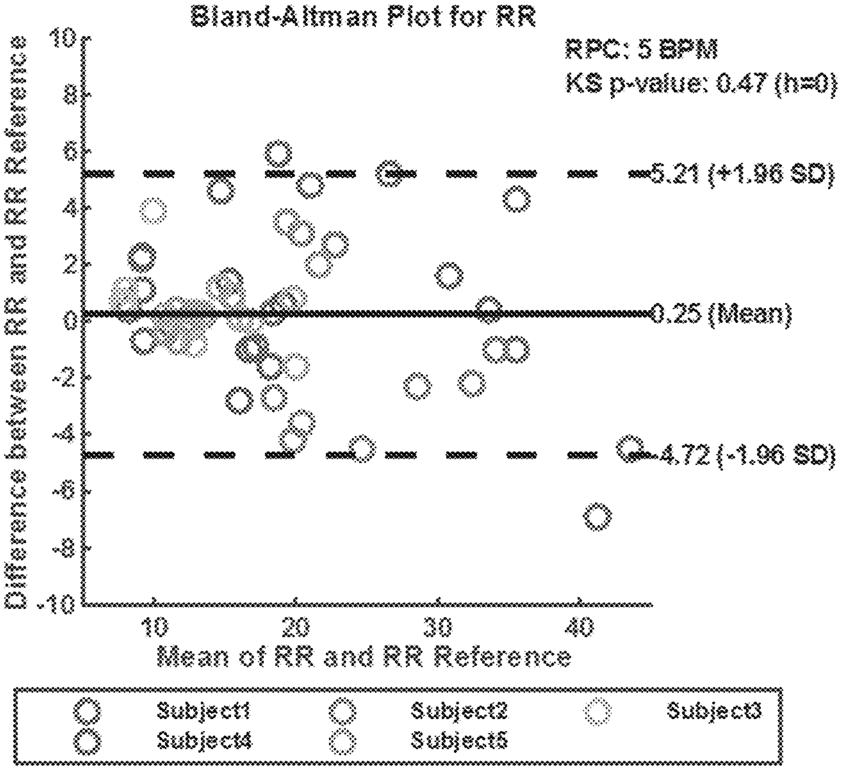
Figure 46C:
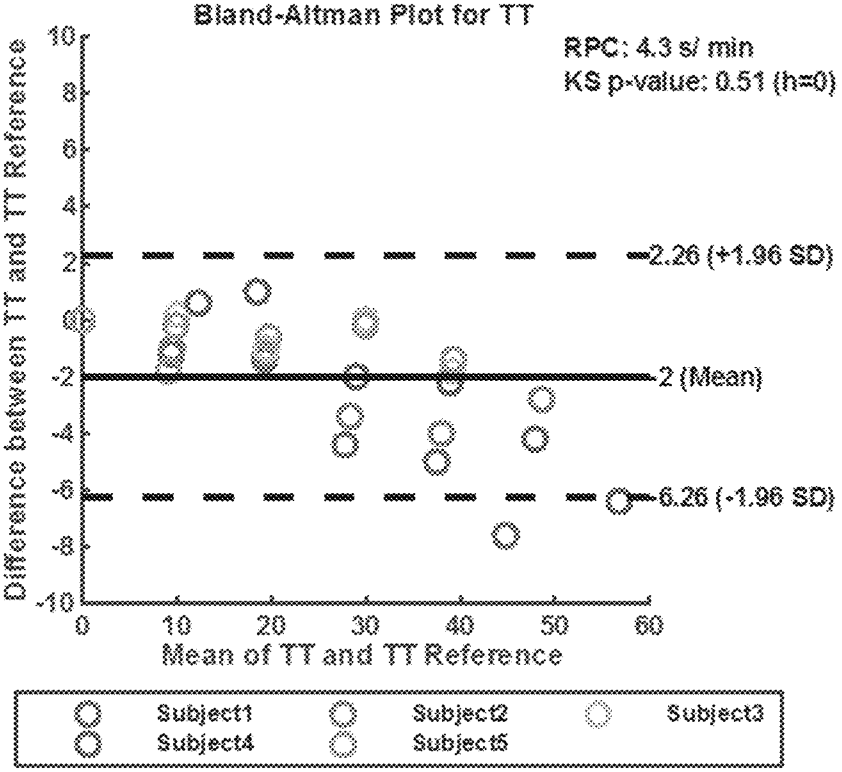
Figure 46D:
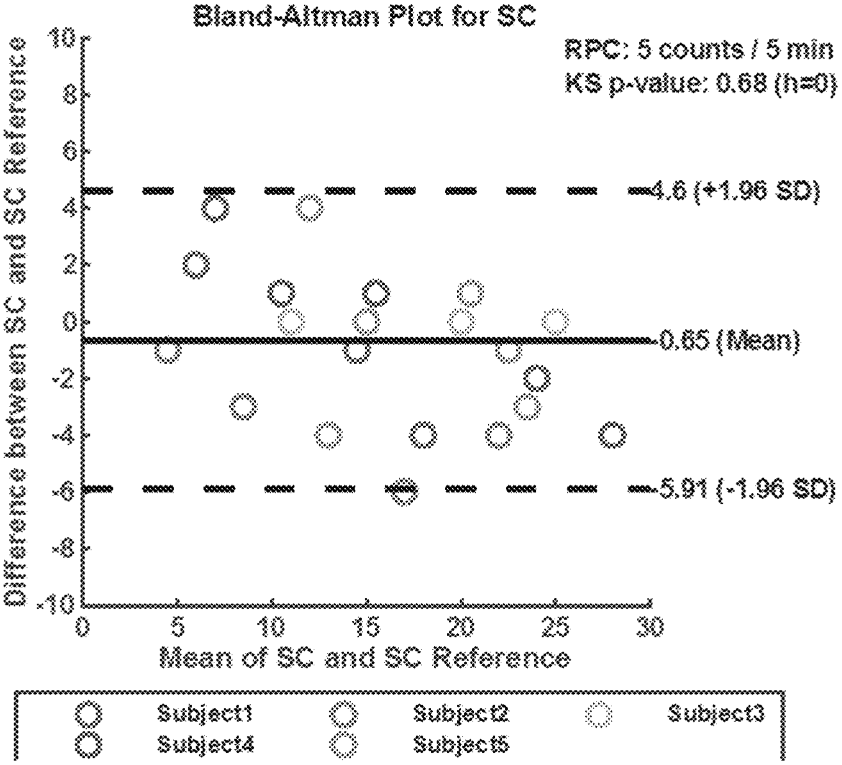

Talking signals are distinguishable by the presence of a second harmonics of the fundamental frequency $F_0$ as a local maxima of power spectral density in the range of human voice (FIG. 45D). Swallow events, on the other hand, features both low-frequency mechanical motion (0.1-5 Hz) and high-frequency (>100 Hz) acoustic ring-down. After zeroing talking and large motion signals, algorithm detects high-frequency and low-frequency signals simultaneously exceeding their quiet-time threshold as the swallowing event (FIG. 45E GMMHMM model).

Figure 50A:
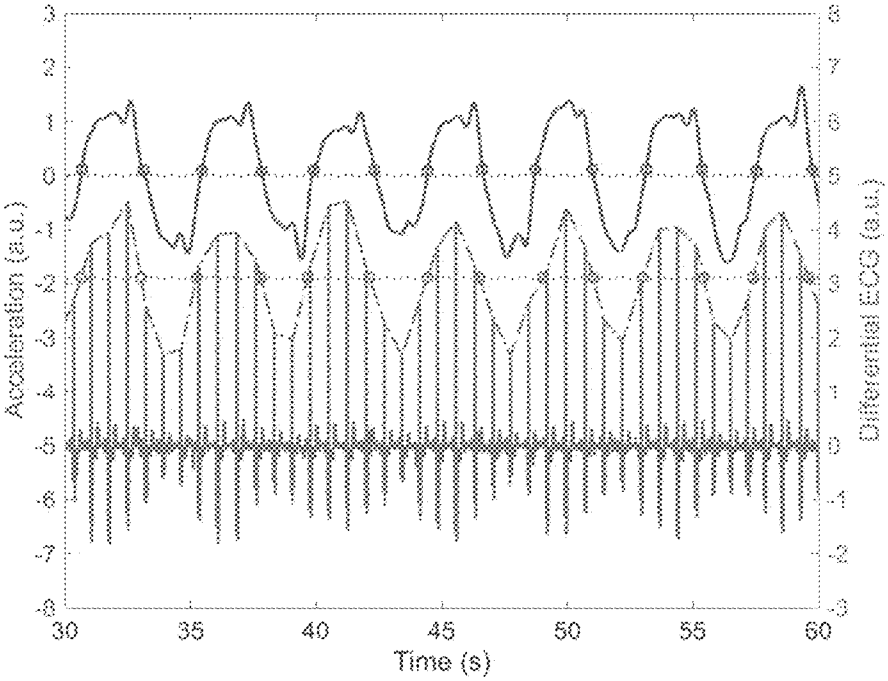
FIGS. 50A-50B.
Figure 50B:
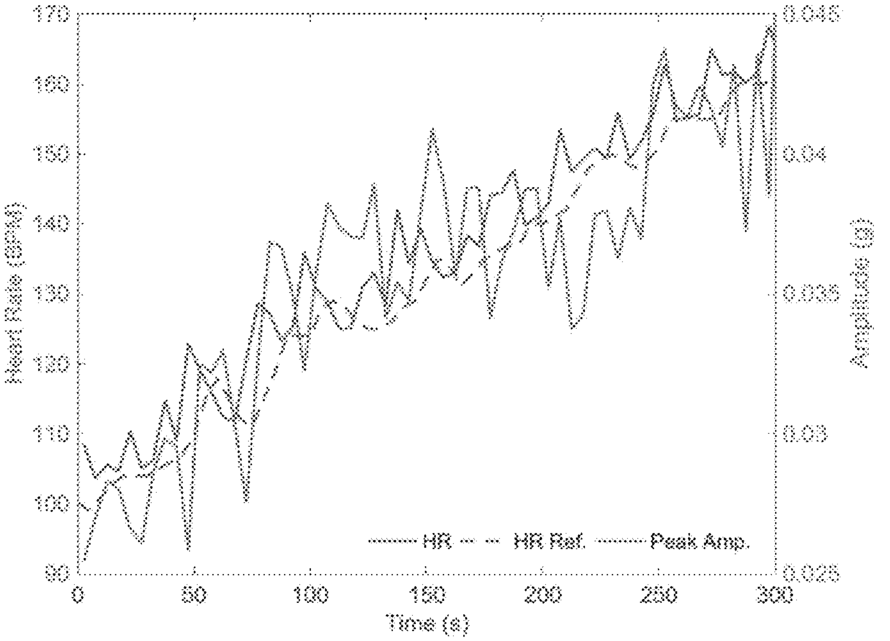

We test the processing flow in two field-study schemes: exercising and dinning. In the exercising scheme, each subject cycles or rests on the elliptical trainer, aiming to span a range of heart rate, from 50 BPM to 180 BPM. The algorithm outputs heart rate to be compared with the polar monitor recordings every five seconds (FIG. 50). The subject manually counts the number of breathing cycles per minute during activities. In the dining scheme, each subject talks and swallows periodically throughout five minutes according to prescribed talking time and swallow counts. In this scheme, each subject conducts five 5-min tests. In each minute of the $n^{th}$ test, the subject talks for n×10 s, then swallow at (n+k)×10 s, k=1, . . . , 6−n.

FIG. 46 shows the Bland-Altman analysis for HR, RR, TT, and SC. The solid and dashed lines mark the mean and 1.96 times standard deviation of the difference between mechano-acoustic measurement and reference standards, respectively. HR has a mean difference of −3.12 BPM and a standard deviation of 5.43 BPM. RR has a mean difference of 0.25 BPM and standard deviation of 2.53 BPM. TT has mean difference of −2.00 s/min and standard deviation of 2.17 s/min. SC has mean difference of −0.65 counts/5 min and standard deviation of 2.68 counts/5 min. The one-sample Kolmogorov-Smirnov test fails to reject the null hypothesis that the difference data comes from a standard normal distribution, against the alternative that it does not come from such a distribution at the 5% significance level for all testing parameters.

Sleep Study

Figure 47A:
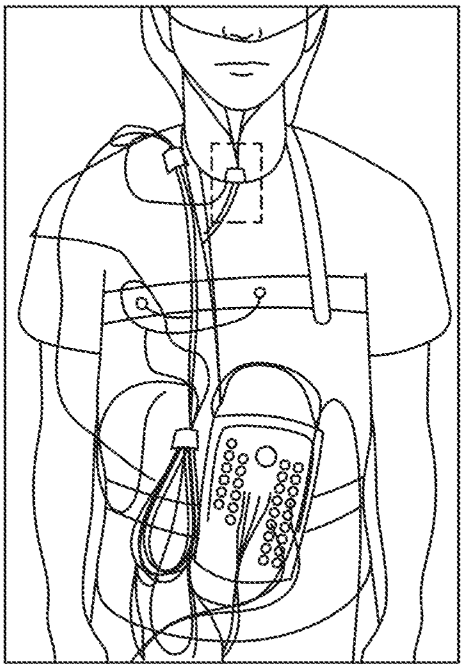
FIGS. 47A-47H. Application of mechano-acoustic sensing in the sleep study.
Figure 47B:
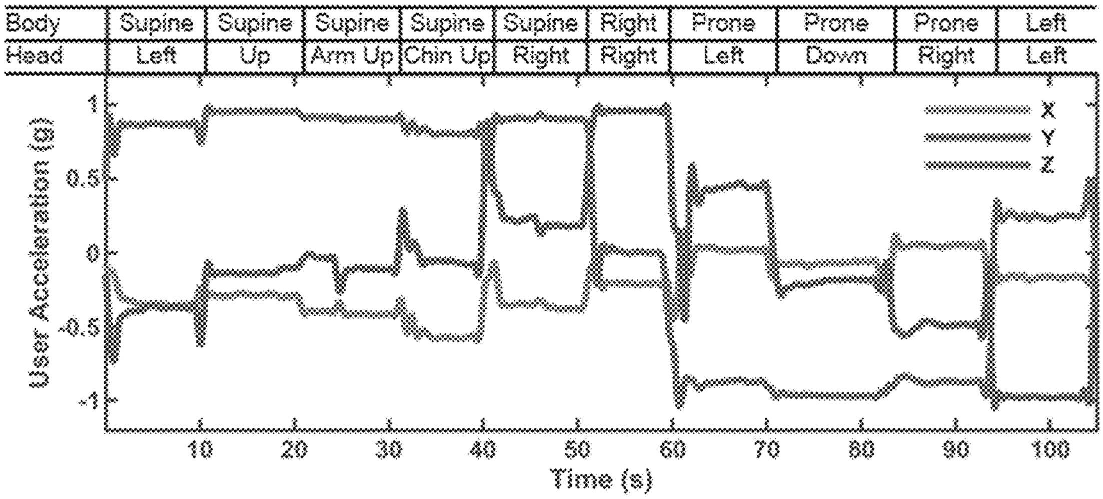
Figure 52:
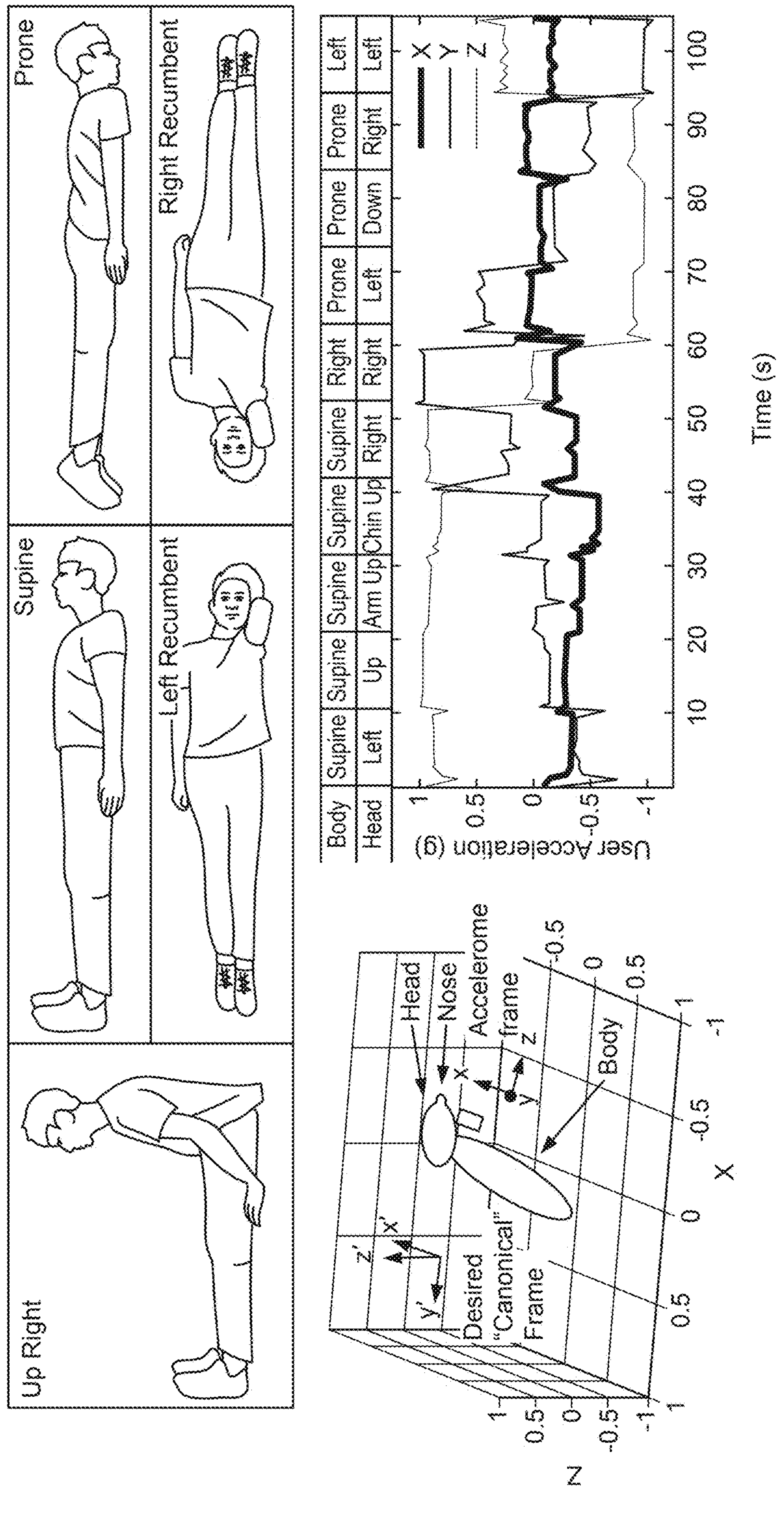
FIG. 52 provides an example of three dimensional body orientation detection using a device as described herein.
Figure 53A:
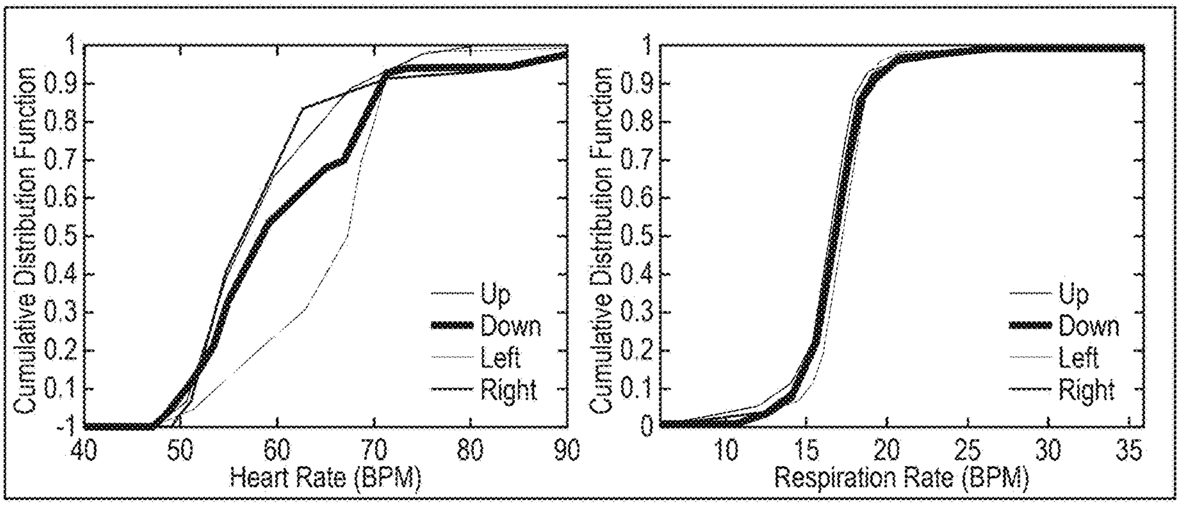
FIGS. 53A-53B provides example heart rate and respiration rate data correlated with body orientation measurement for two different subjects.
Figure 53B:
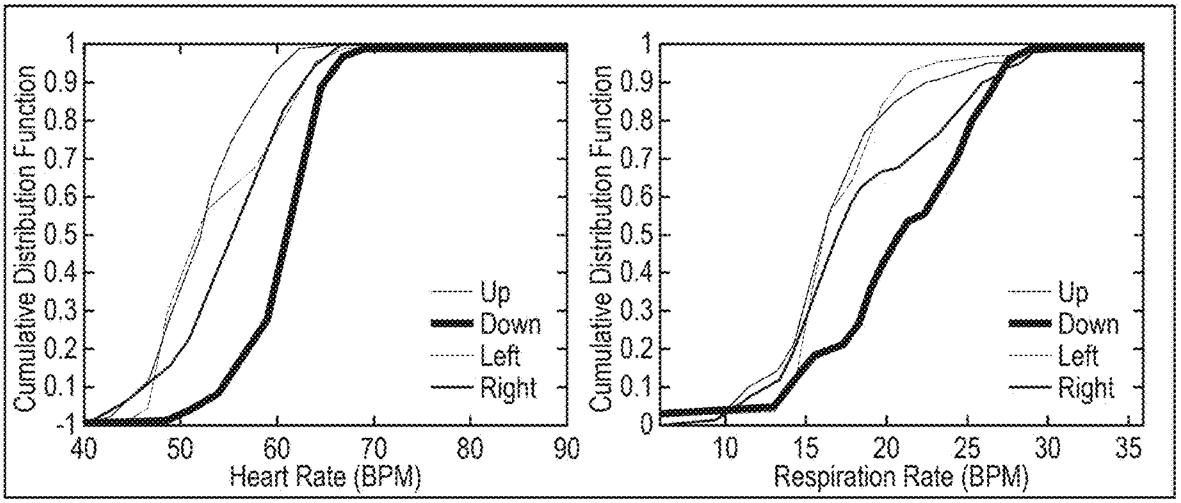
Figure 54A:
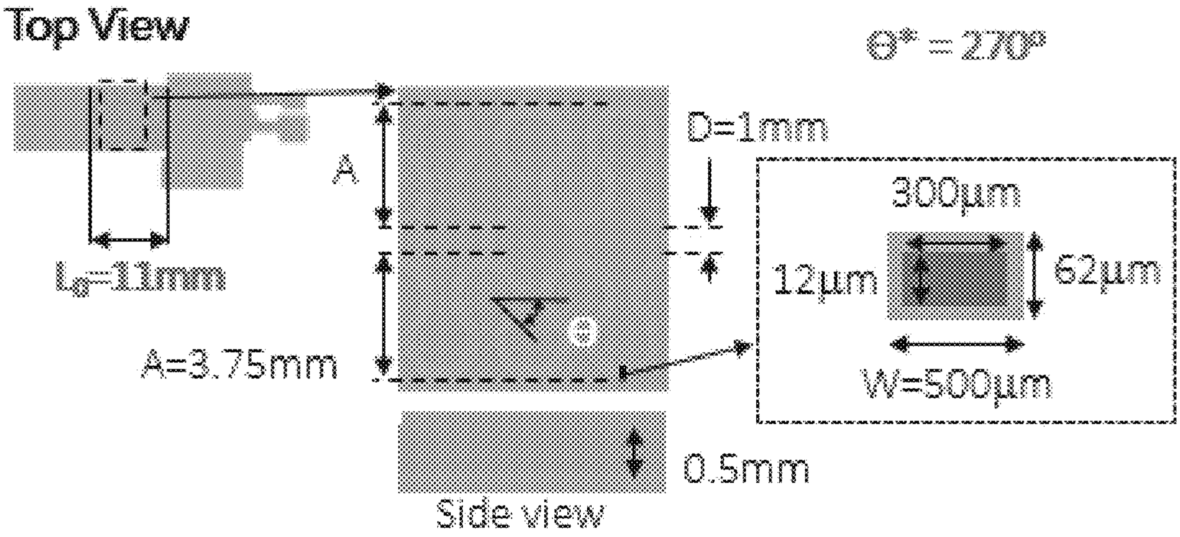
FIGS. 54A-54B. Optimized mechanical design of the interconnects.
Figure 54B:
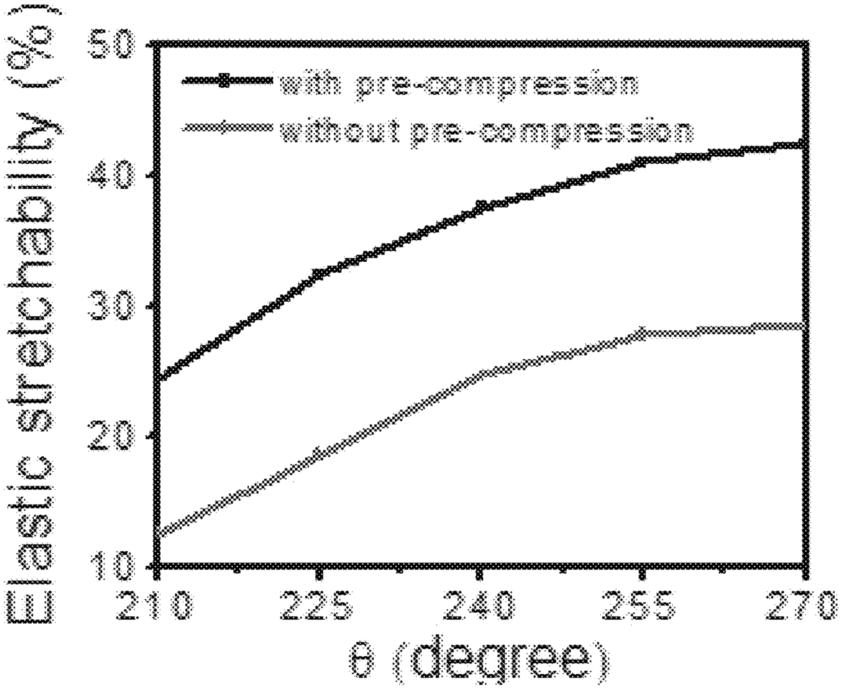

An application to sleep study demonstrates the utility of the device and adapted algorithm in advanced clinical diagnostics. FIG. 47A shows the subject equipped with one mechano-acoustic device on suprasternal notch along with the gold standard polysomnography sensor ensemble, including electrocardiogram (EKG), Pressure Transducer Airflow (PTAF), Abdomen Strain Gauge, Thorax Strain Gauge, Thermistor, Electroencephalography (EEG), and Electrooculography (EOG). In addition to HR, RR detection, taking advantages of the absence of excessive motions during sleep, mechano-acoustic sensor monitors body orientation by measuring solely gravity during quiet time. We demonstrate the detection of body orientation using three-axis acceleration data as shown in FIG. 52.

Figure 47C:
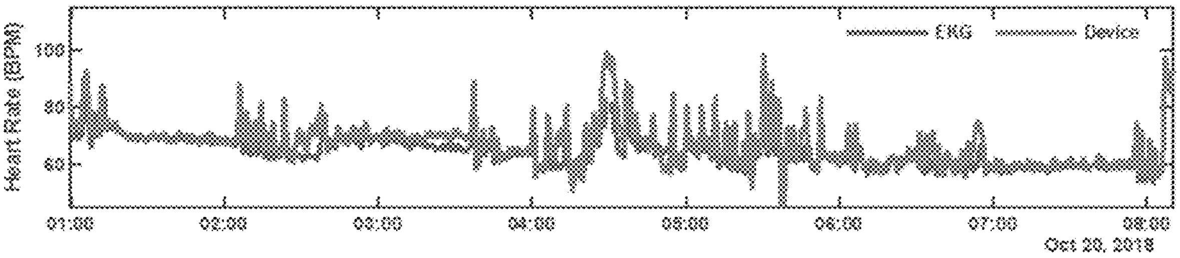
Figure 47D:
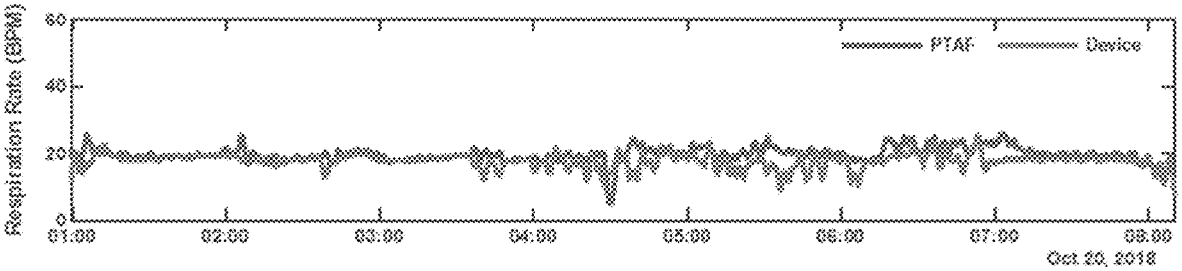
Figure 47E:
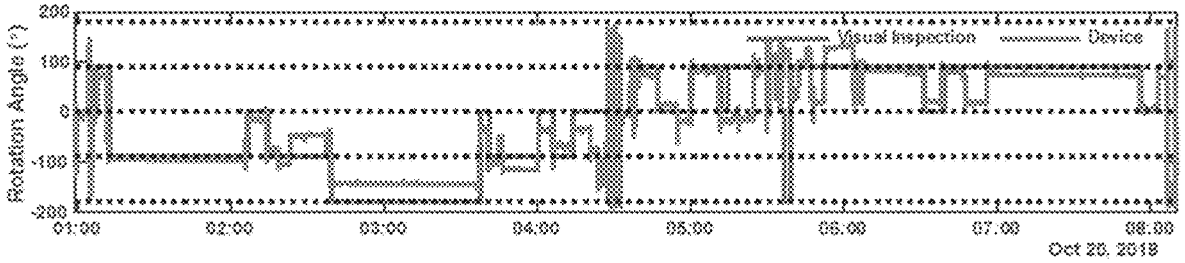
Figure 47F:
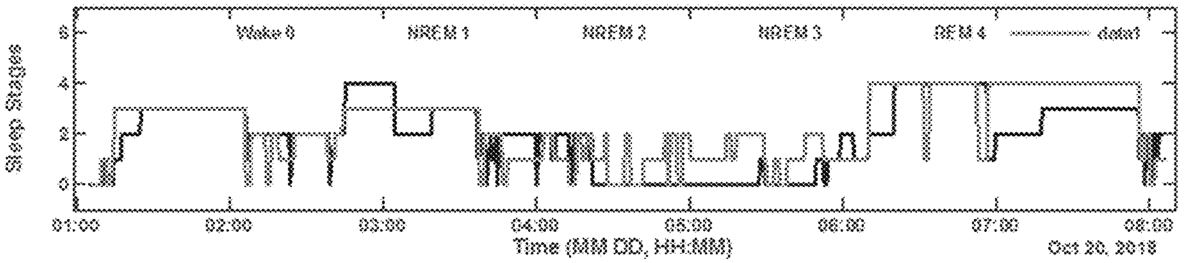

FIGS. 47C-47E compares the HR, RR and body orientation measurements from gold standard and mechano-acoustic devices throughout a sample ~7 hrs sleep study on a male subject. FIG. 47C compares the HR analyzed from 60-s, 50% overlapped time windowed band-passed (1-50 Hz) EKG signals versus band-passed (20-50 Hz) mechano-acoustic z-axis signals. FIG. 47D shows the RR analyzed from 120-s, 50% overlapped time windowed PTAF signal and device z-axis signals, applied with the bandpass filter ($f_1$=0.1 Hz, $f_2$=0.8 Hz). Golden standard body orientation is investigated by visual inspection. The device captures body orientation by measuring quasistatic gravity projection in device frame, which is associated to the core-body frame (See SI for details). FIG. 47E shows that the device captures the general trend of body orientation as the rotation angle around the longitudinal axis, where we define zero degree as supine and the positive sense as turning right. In addition to supine, prone, left recumbent, right recumbent positions, MA signal reconstructs additional details associated with the relative rotation of head against the core body. FIG. 47F shows the inference of the sleep stages from machine learning the accelerometer data in comparison with the clinical-inspected sleep stages. We apply Gaussian Mixture Hidden Markov Model (GMMHMM) for Mel-Frequency- Ceptrum Coefficients (MFCCs) feature clustering the five sleep stages from Wake to Rapid Eye Movement (REM).

Figure 47G:
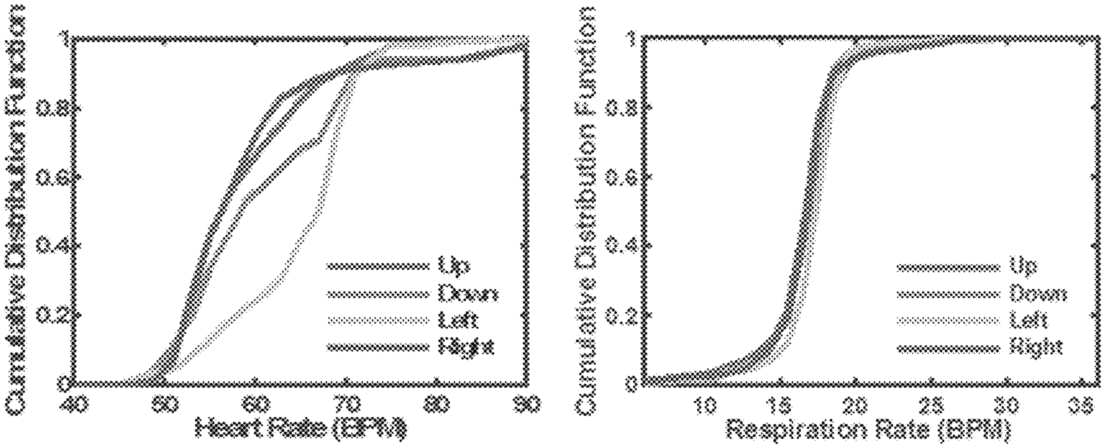
Figure 47H:
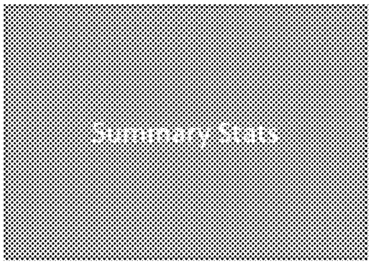
Figure 51A:
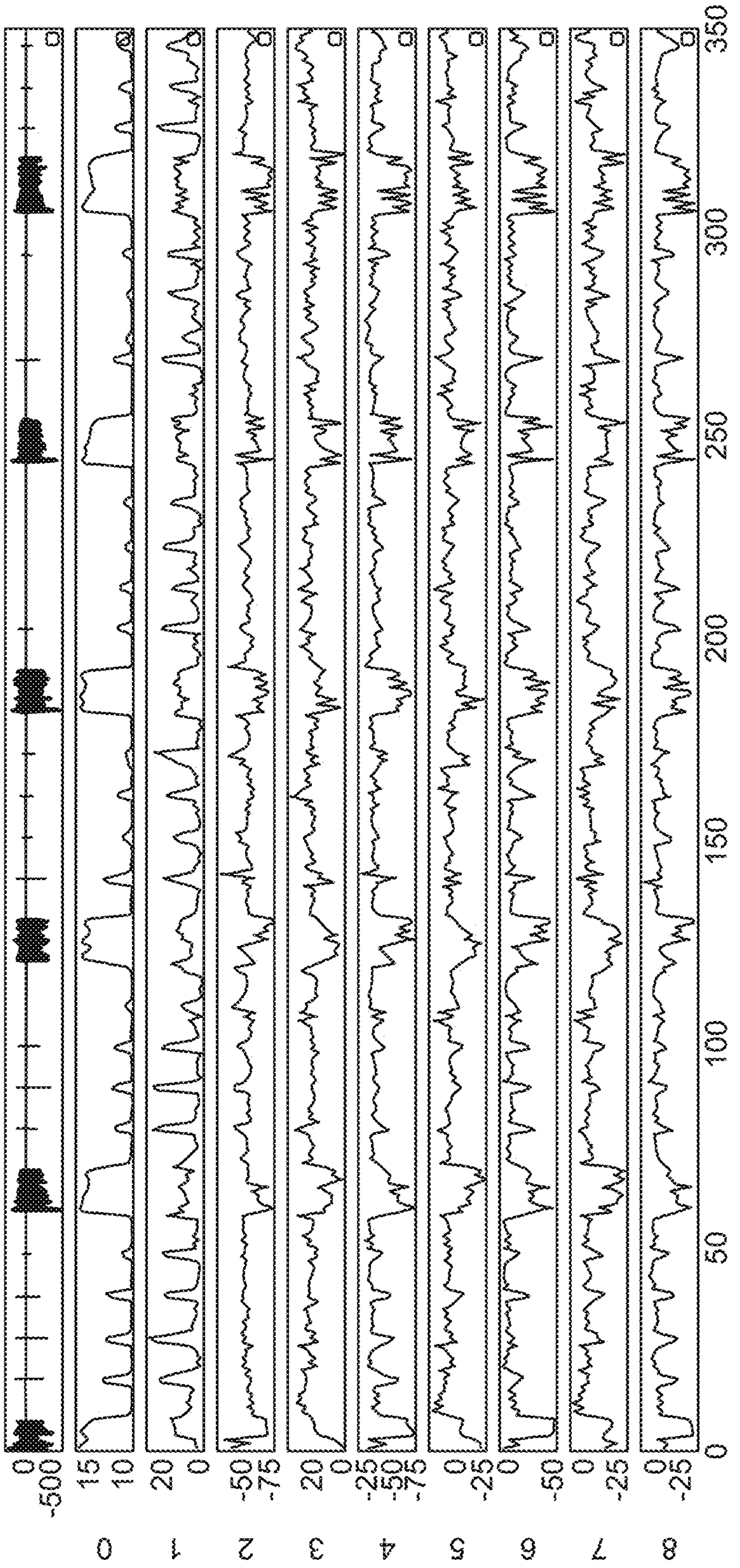
FIGS. 51A-51B provides example experimental data from a group of ten test subjects.
Figure 51B:
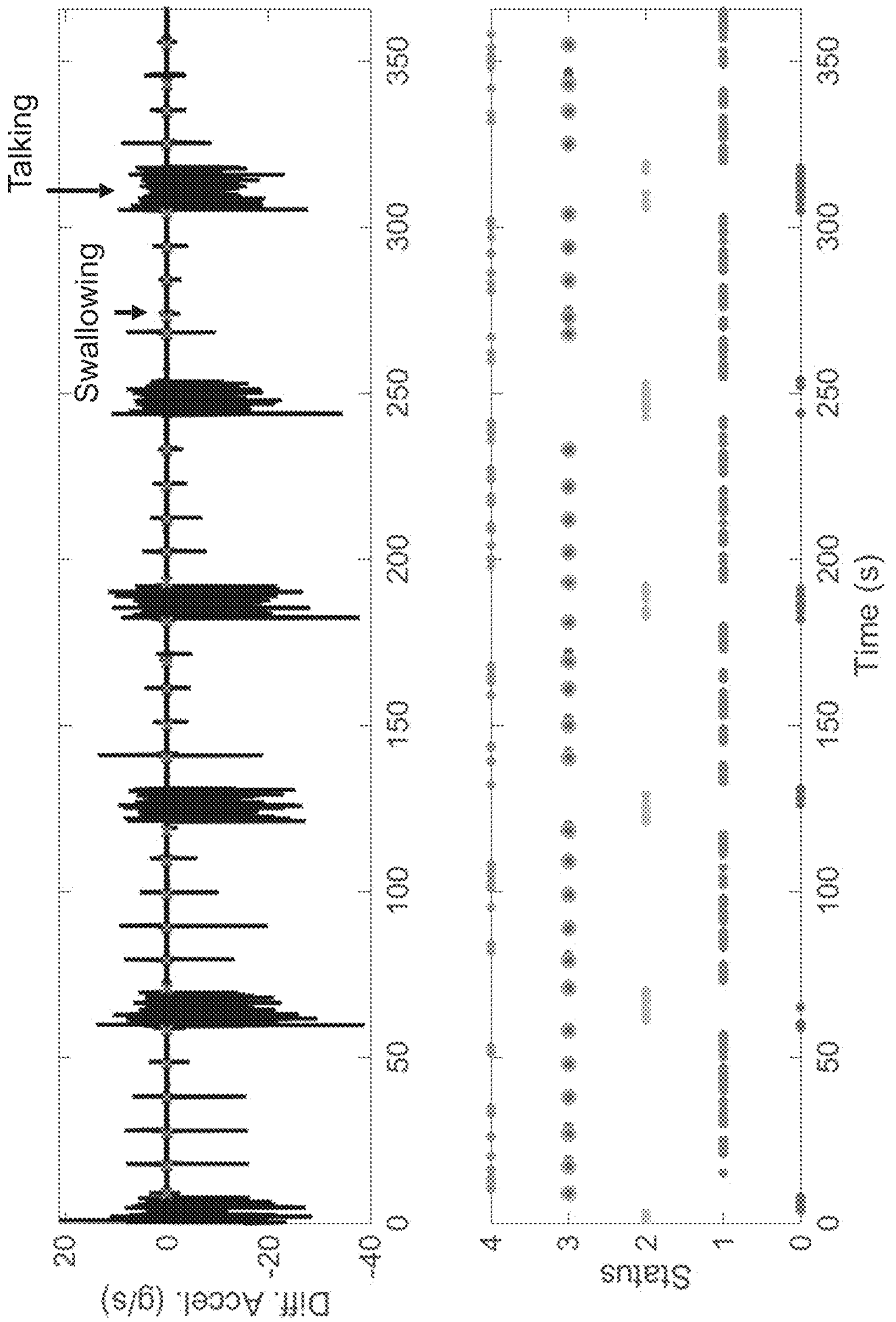

In addition to the conventional sleep study, we analyze the correlation between HR, RR and body orientation. FIG. 47G shows the cumulative distributive function of HR and RR statistics in four classes of body orientation (supine: $-45°<\phi<45°$, left: $-135°<\phi<-45°$, right: $45°<\phi<135°$, prone: $\phi>135°$ or $\phi<-135°$). The data is acquired from seven nights of MA measurement on one male subject. We take advantage of the in-house use case for large statistics on ten subjects (FIG. 51). The results indicate a significantly higher HR and RR when the subjects sleep in Prone-approximate positions.

DISCUSSION

Material and Method

Flexible Electronic Platform: The UV laser cutter (LPKF U4) cuts the board outline and circuit design along with the serpentine shaped interconnects. The cut circuit board is from double-sided copper sheet that has thin copper-clad laminate (12 μm) and copper film (12 μm) bonded to polyimide (PI) film (25 μm) (FLP 7421).

The $CO_2$ laser cutter (VLS3.50) cut FR-4 (0.381 mm, McMaster Carr 1331T37) board with the shape of two islands (FIG. 43B) as stiffening material for the robustness. The board adheres to the back of the circuit board and the circuit boards bend along the designated bending line and adheres to the other side of the FR4 board using the adhesive (Loctite Tak Pak 444). This creates double layered component island with small area. Solder paste (Chip Quik TS391LT) fastens the components onto the circuit board.

Strain Isolation: The $CO_2$ laser cutter (VLS3.50) cut FR-4 board shadow mask and screen-print the silicone gel (Silbione RT Gel 4717 A/B, Bluestar Silicone, E=5 kPa) layer on the bottom encapsulating elastomeric layer. The gel cures on the hotplate at 100° C. for 5 minutes.

Encapsulation: The 3-axis milling machine (Roland MDX 540) cuts the aluminum molds according to the 3D encapsulation mold design from CAD software (ProE Creo 3.0). Two pairs of aluminum molds cast the substrate silicone elastomeric membrane and capping silicone elastomeric membrane (Ecoflex, 00-30, Smooth-on), separately. Each pair of molds have recessed mold design and protruded mold design to create the hollow space within the encapsulation. The Ecoflex poured in the mold cures in the oven at 70° C. for 7 minutes. After depositing silicone gel (strain isolation layer) onto the casted bottom elastomer, the electronics bonds with the substrate by the silicone gel, the strain isolation layer. The capping membrane then bonds to the substrate, using uncured Ecoflex as the bonding agent.

Supplemental Information

Motion artifact suppression in respiration analysis based on wavelet coherence: The wavelet cross spectrum of two time series, $x_n$ and $y_n$, where n=1, 2, . . . , N is:

$$C_{xy}(s,n)=C_x^*(s,n)C_y(s,n), \tag{S.1}$$

where $C_y$(s, n) and $C_y$(s, n) denotes the continuous wavelet transform (CWT) of x and y at scales s and positions n. The superscript denotes the complex conjugate.

$$C_{y'}(a,\ b)=\frac{C_{xy}^*(a,b)}{C_{xx}(a,b)}\cdot C_z(a,b). \tag{S. 2}$$

For the specific application in suppressing motion artifacts occurring in the frequency range of respiration cycles, the computation uses Morlet wavelets. We chose sampling period $\Delta t$=20 s to cover all time scale of interest. The smallest scale for the Morlet wavelets is $s_0=2\Delta t$. The CWT discretizes scales with 16 voices per octave. The number of octaves the nearest integer less than or equal to $\log_2$ N−1, which in this case is 10. We perform moving average filter to smoothing CWT coefficients over 16 scales. We perform the continuous wavelet transforms as well as smoothing operation using the built-in MATLAB™ function "cwt" and "smoothCFS".

Gaussian Mixture Hidden Markov Model (HMM): For robust and flexible classification problems on time-series signals, an effective way is to utilize stochastic approaches that can infer random patterns with probabilities. In this study of mechano-acoustic bio-signals, we introduced the Gaussian Mixture Hidden Markov Model. The model is constructed to describe unobserved states associated to events of interest with discrete probabilities linked by Markov chains. We apply this algorithm to swallowing detection and sleep stage identification.

For the consideration of hyperparameters for the stochastic models, we manually select the number of states to be n=5. For feature extraction approach, we use mel-frequency-cepstrum coefficients (MFCC). MFCC integrates the low-frequency power spectrum density with narrow bands whereas the high-frequency components with wide bands (need to specify, bandwidth ~f). MFCC coefficients take the form of the powers of each band. We choose to work with a total number of fifteen bands, which has been shown to give good balance between system complexity and the feature representation capabilities for the signals sampled at frequency around 1-2 kHz. In swallow detection, the significant features contributed from swallowing activities appear in low order MFCCs and decay with increasing orders. In contrast, speech consists of harmonic components, which exhibit patterns that remain distinctive in high order MFCCs.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, are disclosed separately. When a Markush group or other grouping is used herein, all individual members of the group and all combinations and subcombinations possible of the group are intended to be individually included in the disclosure.

Every formulation or combination of components described or exemplified herein can be used to practice the invention, unless otherwise stated.

Whenever a range is given in the specification, for example, a thickness, a size, a modulus, a mass, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A medical sensing device, comprising:

an electronic device for operable mounting proximate to a suprasternal notch of a user to sense mechano-acoustic signals therefrom, the electronic device further comprising:

an accelerometer to sense one or more mechano-acoustic signals originating from physiological activities in the suprasternal notch region of the user; and a haptic stimulator to provide a haptic stimulus to the user based on a threshold and responsive to the one or more mechano-acoustic signals;

a bidirectional wireless communication system electronically connected to the electronic device for sending an output signal from the electronic device to an external device and receiving commands from an external controller to the electronic device; and a flexible epidermal mounted encapsulation including a mass density and elastic modulus to provide strain isolation and epidermal matching mechano-acoustic impedance to skin at the suprasternal notch, wherein the flexible encapsulation comprises further includes:

a bottom encapsulating layer;

a top encapsulating layer; and a strain isolation layer, wherein the strain isolation layer is supported by the bottom encapsulating layer, and the electronic device is disposed above and supported by the strain isolation layer such that no air pocket exists between the electronic device and the bottom encapsulating layer, wherein the bottom encapsulating layer and the top encapsulating layer are bonded to package the electronic device therein; and wherein the threshold is used to provide a trigger for a corrective, stimulatory, biofeedback, or reinforcing signal back to the user, and is personalized for the user.

2. The medical sensing device of claim 1, wherein the medical sensing device is configured to be wearable, tissue mounted or implantable or in mechanical communication or direct mechanical communication with tissue of a subject.

3. The medical sensing device of claim 1, further comprising a wireless power system for powering the electronic device.

4. The medical sensing device of claim 1, further comprising a processor to provide a real-time metric.

5. The medical sensing device of claim 4, wherein the processor is on-board with the electronic device or is positioned in the external device that is located at a distance from the medical sensing device and in wireless communication with the wireless communication system.

6. The medical sensing device of claim 5, wherein the processor is part of the external device.

7. The medical sensing device of claim 1, wherein the medical sensing device is configured to continuously monitor and generate a real-time metric.

8. The medical sensing device of claim 1, further comprising a processor configured to analyze the output signal.

9. The medical sensing device of claim 8, wherein the processor utilizes machine learning to recognize one or more user-to-user variables between a plurality of users and customize the analysis to an individual user of the medical sensing device.

10. The medical sensing device of claim 9, wherein the machine learning comprises one or more supervised learning algorithms and/or unsupervised learning algorithms customizable to the user.

11. The medical sensing device of claim 9, wherein the machine learning improves a sensor performance parameter used for diagnostic sensing or a therapeutic application and/or a personalized user performance parameter.

12. The medical sensing device of claim 8, wherein the processor is configured to filter and analyze a measured output from the electronic device to improve a sensor performance parameter.

13. The medical sensing device of claim 1, wherein the electronic device further comprises a stretchable electrical interconnect, and a microprocessor.

14. The medical sensing device of claim 1, wherein the medical sensing device is configured to sense single or multiple physiological signals from the user.

15. The medical sensing device of claim 14, wherein the electronic device further comprises a network comprising a plurality of sensors.

16. The medical sensing device of claim 15, wherein at least one of said plurality of sensors is for sensing said single or multiple physiological signals from the user and at least one of said plurality of sensors is for providing a feedback signal to the user.

17. The medical sensing device of claim 1, wherein the stimulator comprises one or more of a vibratory motor, an electrode, a light emitter, a thermal actuator and an audio notification.

18. The medical sensing device of claim 1, wherein the medical sensing device is configured to be worn by a user for a therapeutic swallow application; a social interaction meter; a stroke rehabilitation device; or a respiratory therapeutic device.

19. The medical sensing device of claim 18, wherein the medical sensing device is configured for use in the therapeutic swallow application, wherein the output signal is for one or more swallow parameters selected from the group consisting of swallow frequency, swallow count, and swallow energy.

20. The medical sensing device of claim 19, further comprising a stimulator that provides a haptic signal to the user to engage in a safe swallow.

21. The medical sensing device of claim 20, wherein the safe swallow is determined by sensing onset of inspiration and expiration of a respiratory cycle of the user.

22. The medical sensing device of claim 20, wherein one or more machine learning algorithms are used in a feedback loop for optimization of timing of the haptic signal.

23. The medical sensing device of claim 18, wherein the medical sensing device is configured for use as the social interaction meter, wherein the output signal is for one or more social parameters selected from the group consisting of a talking time, a number of words (fluency rate), a phonatory parameter, a linguistic discourse parameter and a conversation parameter.

24. The medical sensing device of claim 23, further comprising a stimulator that provides a haptic signal to the user to engage in a social interaction event.

25. The medical sensing device of claim 18, wherein the medical sensing device is configured for use in the stroke rehabilitation device, wherein the output signal is for a social parameter and/or a swallow parameter.

26. The medical sensing device of claim 25, wherein the output signal is for use with one or more additional stroke rehabilitation parameters selected from the group consisting of gait, falls and a physical activity.

27. The medical sensing device of claim 25, further comprising a stimulator that provides a haptic signal to the user to engage in a safe swallowing event.

28. The medical sensing device of claim 1, further comprising an external sensor operably connected to the electronic device.

29. The medical sensing device of claim 1, wherein the bottom encapsulating layer and the top encapsulating layer are bonded to package the electronic device with an air pocket between the electronic device and the top encapsulating layer.

30. A medical sensing device, comprising:

an electronic device for operable mounting proximate to a suprasternal notch of a user to sense mechano-acoustic signals therefrom, the electronic device further comprising an accelerometer and a haptic stimulator, wherein the accelerometer provides sensing of vibration or motion originating from physiological activities in the suprasternal notch region of the user, and wherein the stimulator is in electronic communication to provide a haptic stimulus to a user of the medical sensing device;

a wireless communication system electronically connected to the electronic device; and a flexible encapsulation that surrounds the electronic device, wherein the flexible encapsulation comprises a bottom encapsulating layer, a top encapsulating layer, and a strain isolation layer, wherein the strain isolation layer is supported by the bottom encapsulating layer, and the electronic device is disposed above and supported by the strain isolation layer, and wherein the flexible encapsulation includes a mass density and elastic modulus to provide strain isolation and 0 to skin at the suprasternal notch; wherein a threshold is used to provide a trigger for a corrective, stimulatory, biofeedback, or reinforcing signal back to the user, and is personalized for the user.

31. The medical sensing device of claim 30, wherein said wireless communication system is a bidirectional wireless communication system.

32. The medical sensing device of claim 30, wherein said wireless communication system is for sending an output signal from the electronic device to an external device.

33. The medical sensing device of claim 30, wherein said wireless communication system is for receiving commands from an external controller to the electronic device.

34. The medical sensing device of claim 30, wherein the medical sensing device is configured to be wearable or implantable.

35. The medical sensing device of claim 30, further comprising a wireless power system for powering the electronic device.

36. The medical sensing device of claim 30, further comprising a processor to provide a real-time metric.

37. The medical sensing device of claim 30, wherein the medical sensing device is configured to continuously monitor and generate a real-time metric.

38. The medical sensing device of claim 37, wherein the real-time metric is a social metric or a clinical metric.

39. The medical sensing device of claim 32, further comprising a processor configured to analyze the output signal.

40. The medical sensing device of claim 39, wherein the processor utilizes machine learning to recognize one or more user-to-user variables between a plurality of user and customize the analysis to a user of the medical sensing device.

41. The medical sensing device of claim 40, wherein the machine learning comprises one or more supervised learning algorithms and/or unsupervised learning algorithms customizable to a user of the medical sensing device.

42. The medical sensing device of claim 39, wherein the machine learning improves a sensor performance parameter used for diagnostic sensing or a therapeutic application and/or a personalized user performance parameter.

43. The medical sensing device of claim 30, wherein the medical sensing device is configured to be provided on or proximate to a mastoid process of a user.

44. The medical sensing device of claim 30, wherein the medical sensing device is configured to be provided under the chin of a user.

45. The medical sensing device of claim 30, wherein the medical sensing device is configured to be provided on or proximate to the jaw line of a user.

46. The medical sensing device of claim 30, wherein the medical sensing device is configured to be provided on or proximate to the clavicle of a user.

47. The medical sensing device of claim 30, wherein the medical sensing device is configured to be provided on or proximate to a bony prominence of a user.

48. The medical sensing device of claim 30, wherein the medical sensing device is configured to be provided behind the ear of a user.

49. The medical sensing device of claim 30, wherein the electronic device is a flexible device.

50. The medical sensing device of claim 30, wherein the electronic device is a stretchable device.

51. The medical sensing device of claim 30, wherein the electronic device comprises a multilayer floating device architecture.

52. The medical sensing device of claim 30, wherein the electronic device is at least partially supported by an elastomer substrate, superstrate or both.

53. The medical sensing device of claim 30, wherein the electronic device is at least partially supported by a silicone elastomer providing for strain isolation.

54. The medical sensing device of claim 30, wherein the electronic device is at least partially encapsulated by a moisture resistant enclosure.

55. The medical sensing device of claim 31, wherein the bidirectional wireless communication system is powered by a wireless re-chargeable system.

56. The medical sensing device of claim 55, wherein the wireless re-chargeable system comprises one or more of a rechargeable battery, an inductive coil, a full wave rectifier, a regulator, a charging IC and PNP transistor.

57. The medical sensing device of claim 30, further comprising a gyroscope.

58. The medical sensing device of claim 57, wherein the gyroscope is a 3-axis gyroscope.

59. The medical sensing device of claim 30, further comprising a magnetometer.

60. The medical sensing device of claim 30, wherein the medical sensing device is operably mounted proximate to a suprasternal notch of a user.

* * * * *